(12) United States Patent
Jackson et al.

(10) Patent No.: US 12,137,944 B2
(45) Date of Patent: Nov. 12, 2024

(54) BONE ANCHOR ASSEMBLY HAVING A TOOL DEPLOYABLE INSERT IN COMPRESSIVE OVERLAPPING ENGAGEMENT WITH A RETAINER

(71) Applicant: Roger P. Jackson, Prairie Village, KS (US)

(72) Inventors: Roger P. Jackson, Prairie Village, KS (US); James L. Surber, Kansas City, KS (US); Nathaniel D. Ginzton, Boise, ID (US)

( * ) Notice: Subject to any disclaimer, the term of this patent is extended or adjusted under 35 U.S.C. 154(b) by 0 days.

(21) Appl. No.: 18/055,399

(22) Filed: Nov. 14, 2022

(65) Prior Publication Data

US 2023/0074087 A1    Mar. 9, 2023

Related U.S. Application Data

(63) Continuation of application No. 17/564,784, filed on Dec. 29, 2021, now Pat. No. 11,497,533, which is a
(Continued)

(51) Int. Cl.
*A61B 17/70* (2006.01)
*A61B 17/86* (2006.01)

(52) U.S. Cl.
CPC ...... *A61B 17/7037* (2013.01); *A61B 17/7076* (2013.01); *A61B 17/8605* (2013.01); *A61B 17/864* (2013.01)

(58) Field of Classification Search
CPC ............ A61B 17/7032; A61B 17/7035; A61B 17/7037
See application file for complete search history.

(56) References Cited

U.S. PATENT DOCUMENTS 5,669,911 A    9/1997  Errico et al.
5,690,630 A    11/1997 Errico et al.
(Continued)

FOREIGN PATENT DOCUMENTS

EP         1857064         11/2007
WO    WO 2020/056385       3/2020
WO    WO 2021/127251       6/2021

*Primary Examiner* — Eduardo C Robert
*Assistant Examiner* — Michelle C Eckman
(74) *Attorney, Agent, or Firm* — Polsinelli PC

(57) ABSTRACT

A bone anchor assembly includes a shank having a head and an anchor portion, and a receiver having a first channel to receive a rod and an axial bore with an upper internal thread, interference abutment surfaces below the upper internal thread, and a bottom opening. The assembly also includes an insert having a second channel to receive the rod and opposite lateral protrusions positioned above the interference abutment surfaces upon loading into a first position within the axial bore. The assembly further includes a resiliently expandable retainer positionable within the axial bore adjacent the bottom opening to capture and hold the head in the receiver. After the head is uploaded into the axial bore, the insert is downwardly deployable by tooling into a second position with the opposite lateral protrusions being forced below the interference abutment surfaces and with lower portions of the insert entering into compressive overlapping engagement with the retainer to hold down the retainer within the axial bore.

18 Claims, 25 Drawing Sheets

Related U.S. Application Data continuation of application No. 16/686,122, filed on Nov. 16, 2019, now Pat. No. 11,234,738.

(60) Provisional application No. 62/811,250, filed on Feb. 27, 2019, provisional application No. 62/768,732, filed on Nov. 16, 2018.

(56) References Cited

U.S. PATENT DOCUMENTS

| | | | |
|---|---|---|---|
| 6,010,503 | A | 1/2000 | Richelsoph et al. |
| 6,090,111 | A | 7/2000 | Nichols |
| 6,254,602 | B1 | 7/2001 | Justis |
| 6,355,040 | B1 | 3/2002 | Richelsoph et al. |
| 6,565,565 | B1 | 5/2003 | Yuan et al. |
| 6,626,908 | B2 | 9/2003 | Cooper et al. |
| 6,740,086 | B2 | 5/2004 | Richelsoph |
| 7,087,057 | B2 | 8/2006 | Konieczynski et al. |
| 7,163,539 | B2 | 1/2007 | Abdelgany et al. |
| 7,264,621 | B2 | 9/2007 | Coates et al. |
| 7,311,712 | B2 | 12/2007 | Dalton |
| 7,377,923 | B2 | 5/2008 | Purcell et al. |
| 7,445,627 | B2 | 11/2008 | Hawkes et al. |
| 7,604,655 | B2 | 10/2009 | Warnick |
| 7,686,834 | B2 | 3/2010 | Saint Martin |
| 7,686,835 | B2 | 3/2010 | Warnick |
| 7,766,915 | B2 | 8/2010 | Jackson |
| 7,766,945 | B2 | 8/2010 | Nilsson et al. |
| 7,776,067 | B2 | 8/2010 | Jackson |
| 7,842,073 | B2 | 11/2010 | Richelsoph et al. |
| 7,909,830 | B2 | 3/2011 | Frigg et al. |
| 7,914,536 | B2 | 3/2011 | MacDonald et al. |
| 7,988,694 | B2 | 8/2011 | Barrus et al. |
| 8,021,397 | B2 | 9/2011 | Farris et al. |
| 8,048,112 | B2 | 11/2011 | Suzuki et al. |
| 8,066,744 | B2 | 11/2011 | Justis et al. |
| 8,083,776 | B2 | 12/2011 | Alvarez |
| 8,197,517 | B1 | 6/2012 | Lab et al. |
| 8,211,472 | B2 | 7/2012 | Peterson et al. |
| 8,398,683 | B2 | 3/2013 | Berrevoets et al. |
| 8,444,681 | B2 | 5/2013 | Jackson et al. |
| 8,449,578 | B2 | 5/2013 | Keiser et al. |
| 8,556,938 | B2 | 10/2013 | Jackson et al. |
| 8,628,558 | B2 | 1/2014 | Harvey et al. |
| 8,663,298 | B2 | 3/2014 | Keyer et al. |
| 8,696,712 | B2 | 4/2014 | Biedermann et al. |
| 8,888,827 | B2 | 11/2014 | Harper et al. |
| 8,926,671 | B2 | 1/2015 | Biedermann et al. |
| 8,951,290 | B2 | 2/2015 | Hammer et al. |
| 8,986,349 | B1 | 3/2015 | German et al. |
| 8,998,959 | B2 | 4/2015 | Jackson et al. |
| 9,044,272 | B2 | 6/2015 | Shaffrey et al. |
| 9,078,705 | B2 | 7/2015 | Matthis et al. |
| 9,119,674 | B2 | 9/2015 | Matthis et al. |
| 9,155,567 | B2 | 10/2015 | Auerbach et al. |
| 9,168,069 | B2 | 10/2015 | Jackson et al. |
| 9,198,695 | B2 | 12/2015 | Shluzas et al. |
| 9,259,247 | B2 | 2/2016 | Chandanson et al. |
| 9,358,047 | B2 | 6/2016 | Mishra et al. |
| 9,393,047 | B2 | 7/2016 | Jackson et al. |
| 9,480,517 | B2 | 11/2016 | Jackson et al. |
| 9,492,204 | B2 | 11/2016 | Biedermann et al. |
| 9,615,858 | B2 | 4/2017 | Doubler et al. |
| 9,649,134 | B2 | 5/2017 | Hannen |
| 9,655,652 | B2 | 5/2017 | Biedermann et al. |
| 9,707,013 | B2 | 7/2017 | Rezach et al. |
| 9,763,702 | B2 | 9/2017 | Schlaepfer et al. |
| 9,907,574 | B2 | 3/2018 | Jackson et al. |
| 9,918,745 | B2 | 3/2018 | Jackson et al. |
| 9,924,975 | B2 | 3/2018 | Jackson et al. |
| 9,980,753 | B2 | 5/2018 | Jackson et al. |
| 10,039,572 | B2 | 8/2018 | Harris et al. |
| 10,052,136 | B2 | 8/2018 | Nelson |
| 10,064,658 | B2 | 9/2018 | Jackson et al. |
| 10,154,859 | B2 | 12/2018 | Keyer et al. |
| 10,172,647 | B2 | 1/2019 | Elsbury |
| 10,188,432 | B2 | 1/2019 | Jackson et al. |
| 10,285,738 | B1 | 5/2019 | Doubler et al. |
| 10,463,402 | B2 | 11/2019 | Biester et al. |
| 10,485,594 | B2 | 11/2019 | Toon et al. |
| 10,507,043 | B1 | 12/2019 | Gladieux |
| 10,517,645 | B2 * | 12/2019 | van der Pol ......... A61B 17/864 |
| 10,695,100 | B2 | 6/2020 | May et al. |
| 11,234,738 | B2 | 2/2022 | Jackson et al. |
| 2003/0149431 | A1 | 8/2003 | Varieur |
| 2003/0153911 | A1 | 8/2003 | Shluzas |
| 2004/0122425 | A1 * | 6/2004 | Suzuki ............... A61B 17/7062 606/267 |
| 2005/0203516 | A1 | 9/2005 | Biedermann et al. |
| 2006/0058788 | A1 | 3/2006 | Hammer et al. |
| 2006/0161152 | A1 | 7/2006 | Ensign et al. |
| 2006/0217716 | A1 | 9/2006 | Baker et al. |
| 2007/0118123 | A1 | 5/2007 | Strausbaugh et al. |
| 2007/0270813 | A1 | 11/2007 | Garamszegi |
| 2009/0182336 | A1 * | 7/2009 | Brenzel ............... A61B 17/869 606/62 |
| 2010/0234902 | A1 * | 9/2010 | Biedermann ...... A61B 17/7037 606/305 |
| 2011/0046683 | A1 | 2/2011 | Biedermann et al. |
| 2012/0143266 | A1 * | 6/2012 | Jackson ............. A61B 17/7032 606/328 |
| 2013/0103098 | A1 | 4/2013 | Jackson et al. |
| 2013/0150852 | A1 * | 6/2013 | Shluzas ............... A61B 17/7001 606/65 |
| 2013/0218213 | A1 | 8/2013 | Lemoine |
| 2014/0025119 | A1 | 1/2014 | Biedermann et al. |
| 2014/0121703 | A1 * | 5/2014 | Jackson ............. A61B 17/7032 606/246 |
| 2014/0142634 | A1 * | 5/2014 | Schlaepfer ........... A61B 17/704 29/428 |
| 2016/0361096 | A1 * | 12/2016 | van der Pol ....... A61B 17/7076 |
| 2017/0258606 | A1 * | 9/2017 | Afzal ................... A61F 2/4465 |

\* cited by examiner

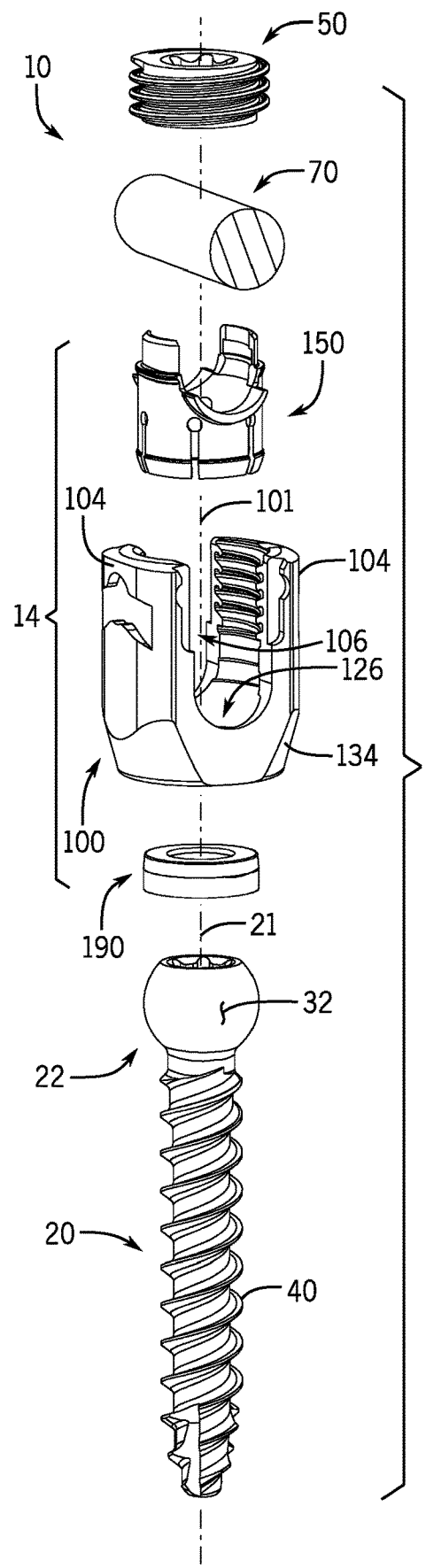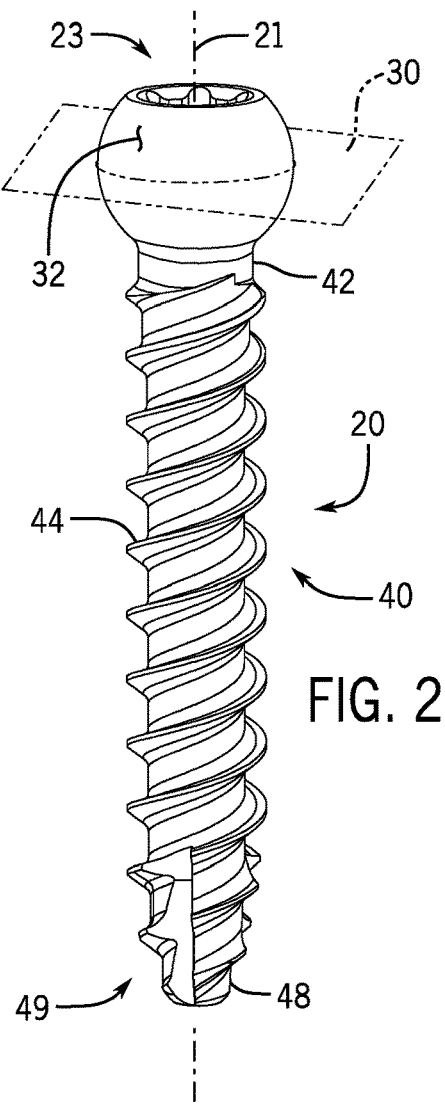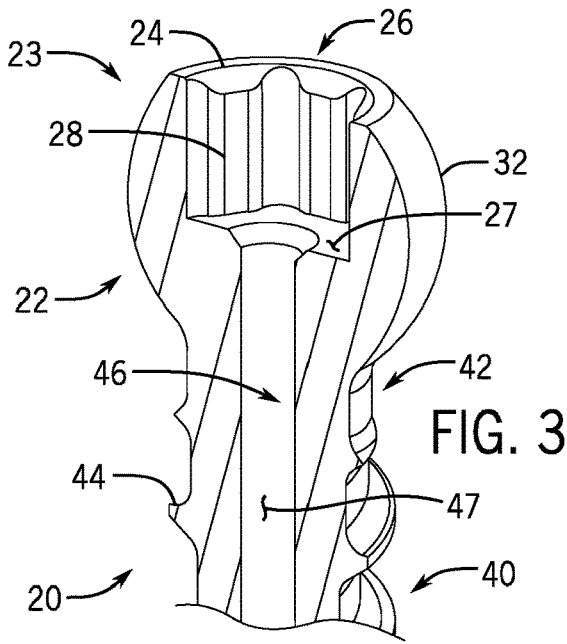

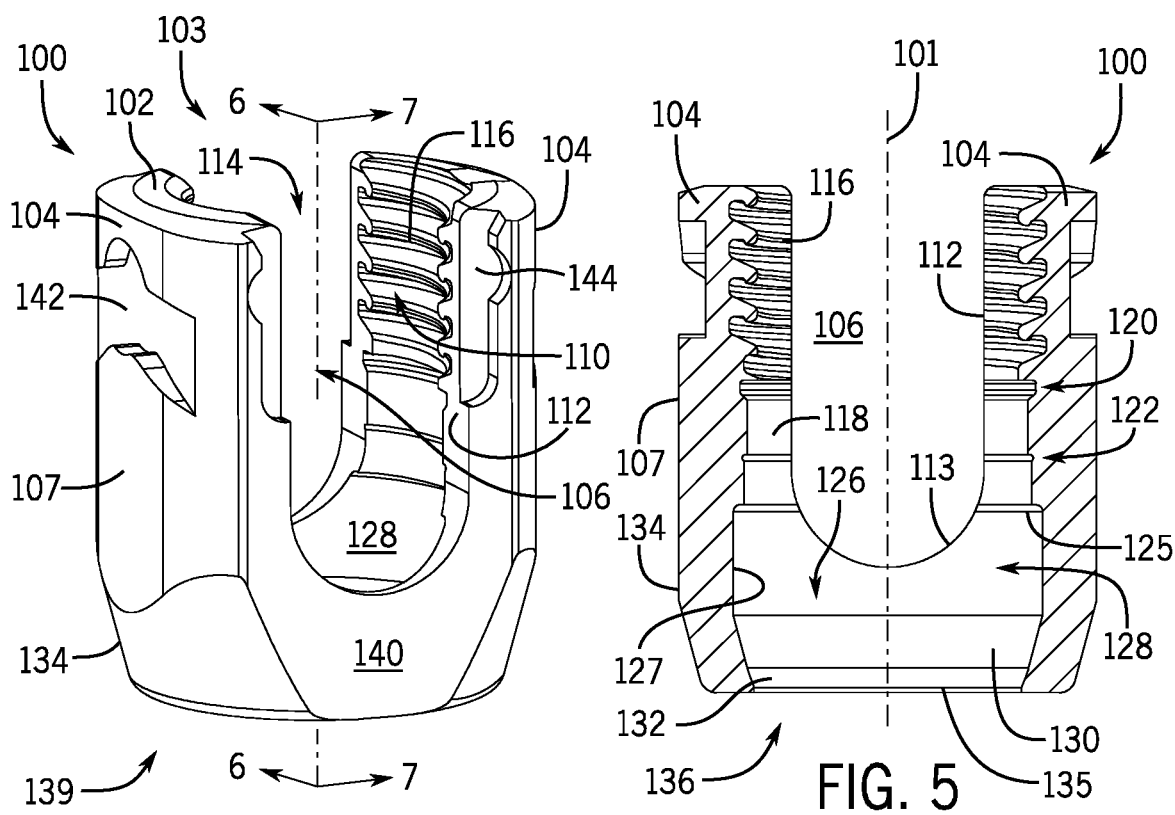
FIG. 4
FIG. 5
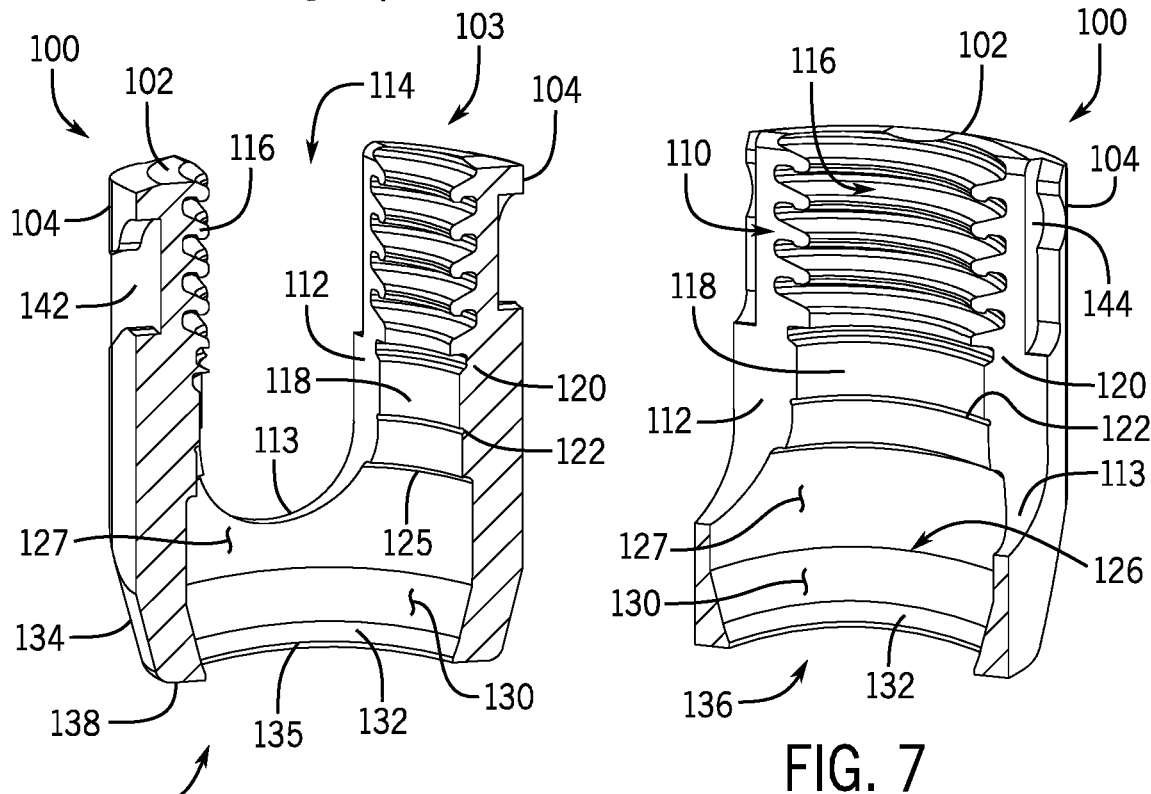
FIG. 6
FIG. 7

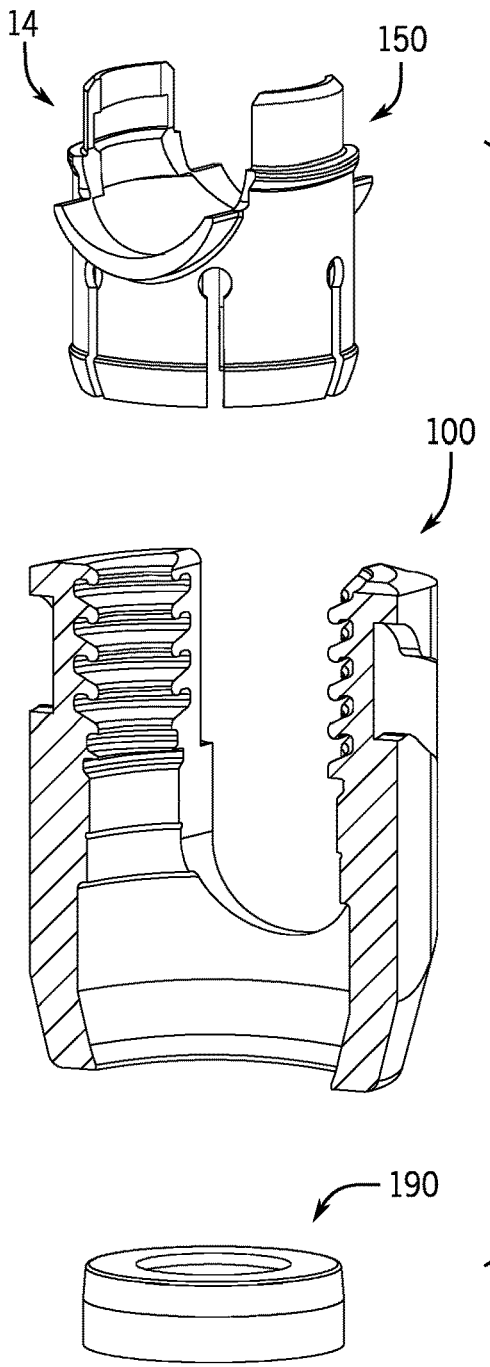
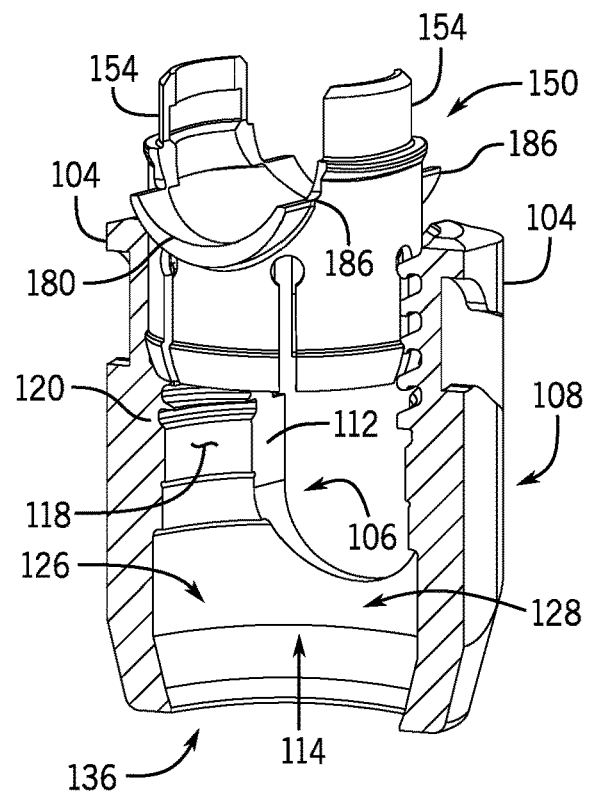
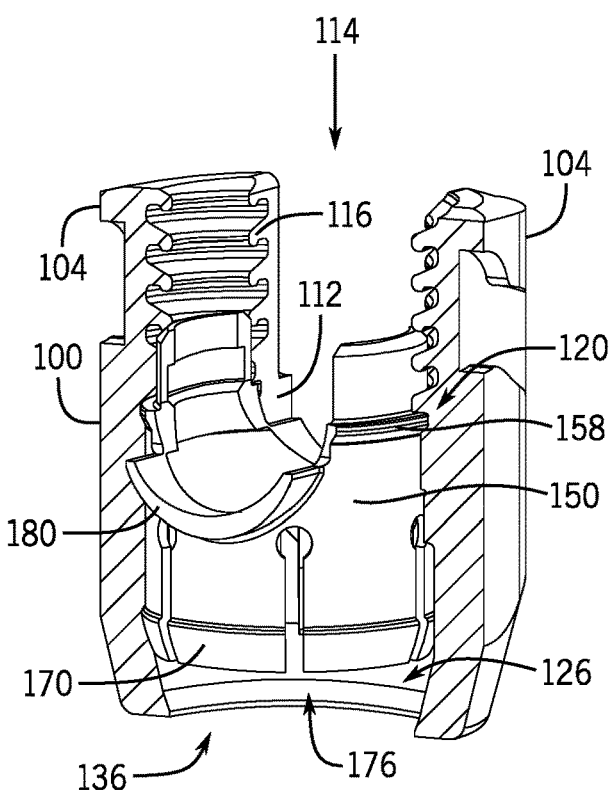
FIG. 19
FIG. 20
FIG. 21

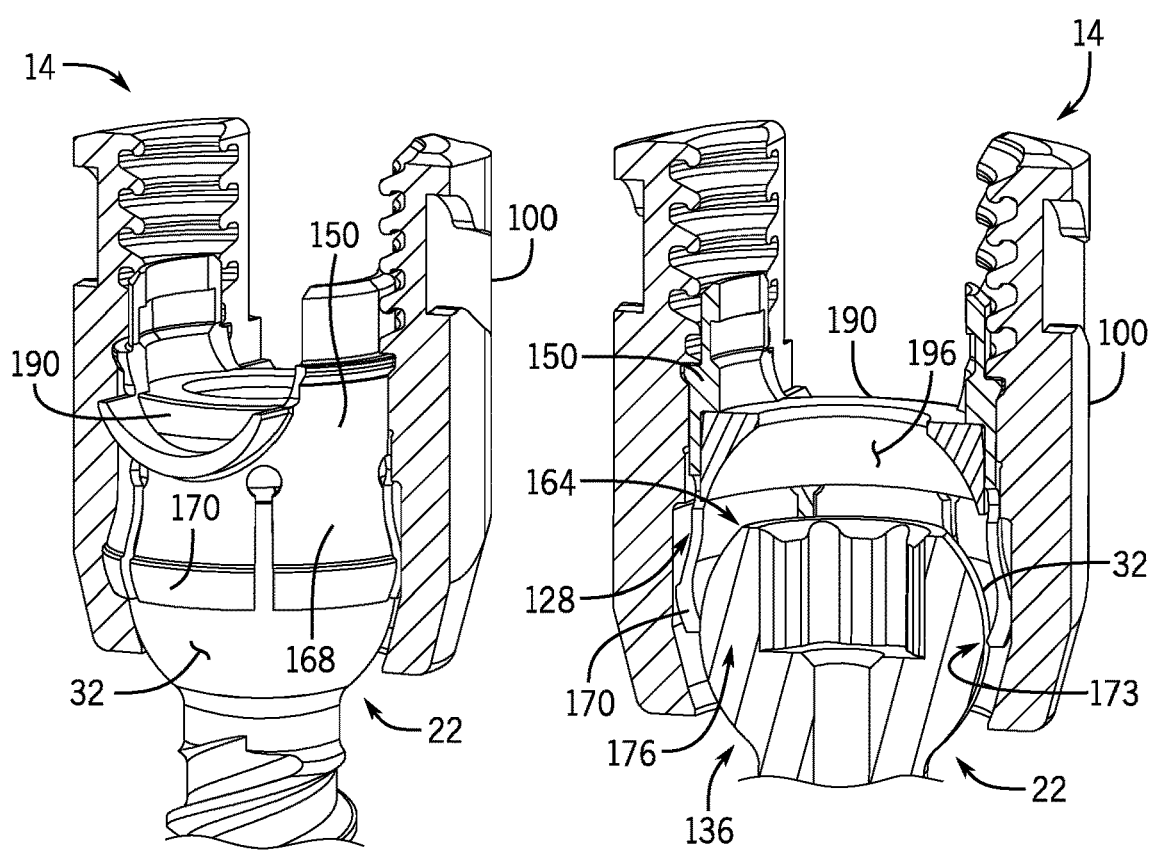
FIG. 32
FIG. 33
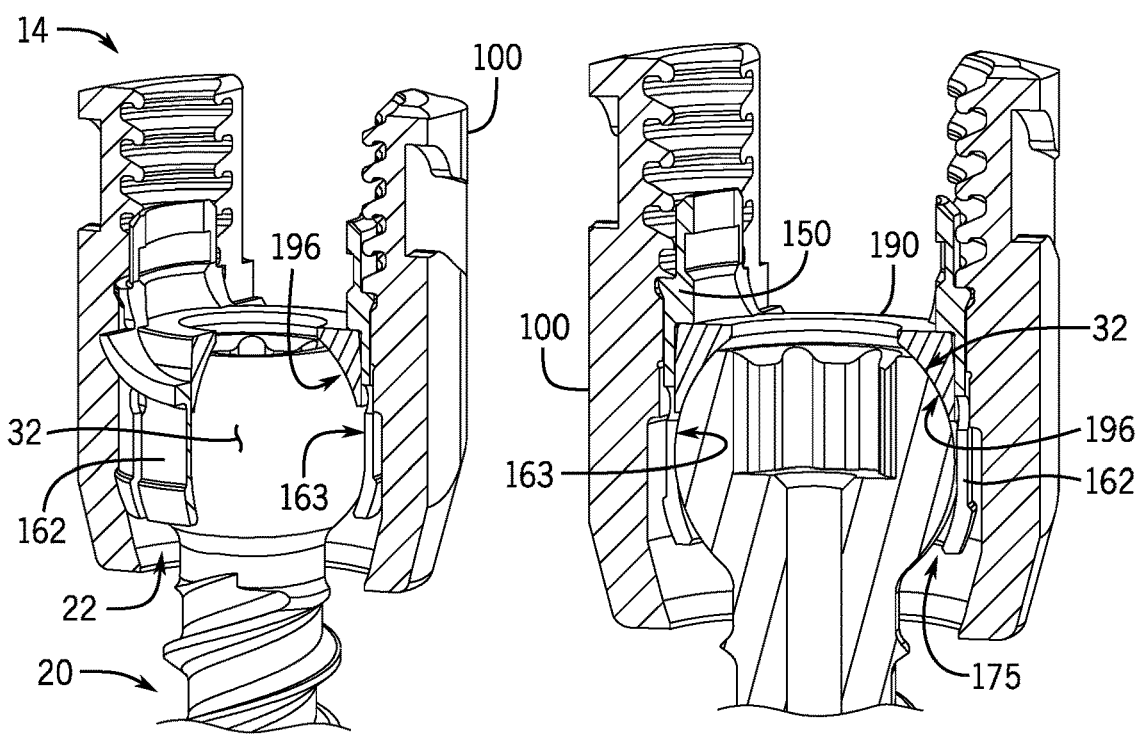
FIG. 34
FIG. 35

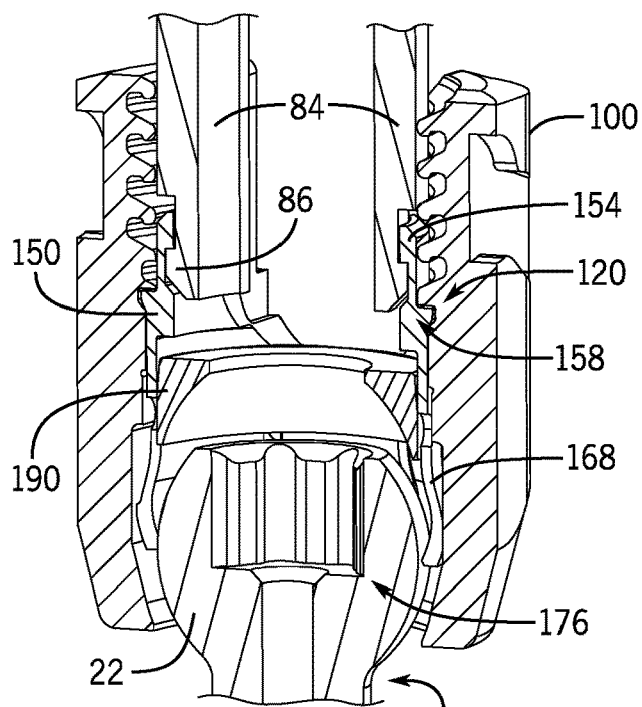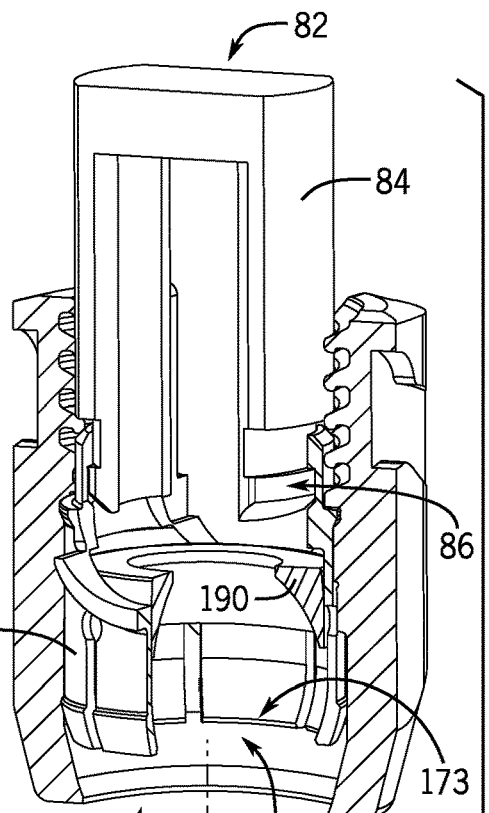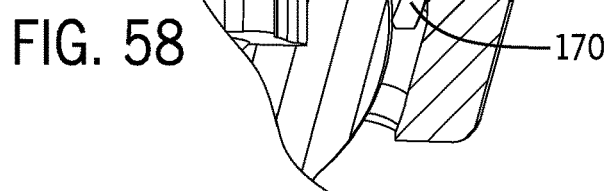

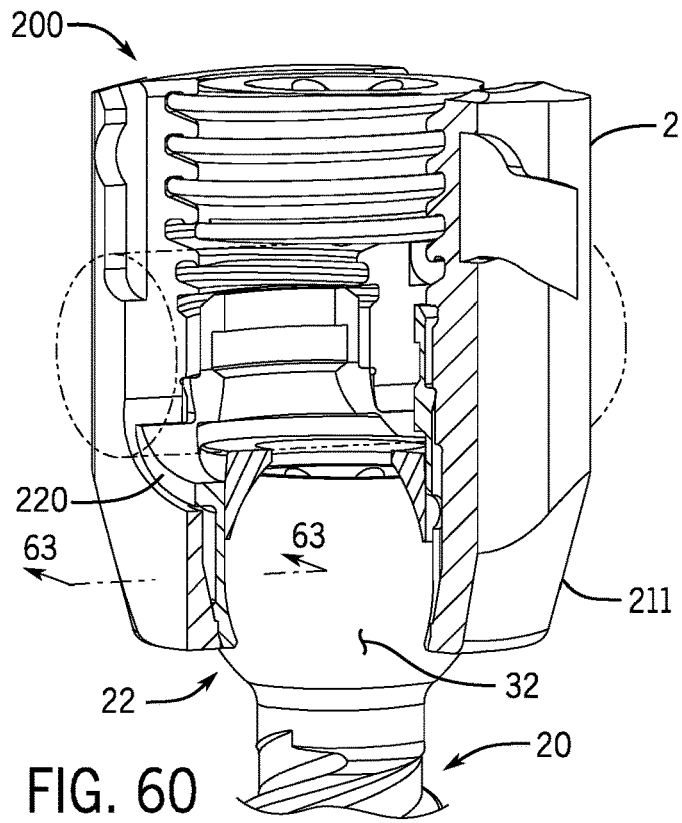
FIG. 60
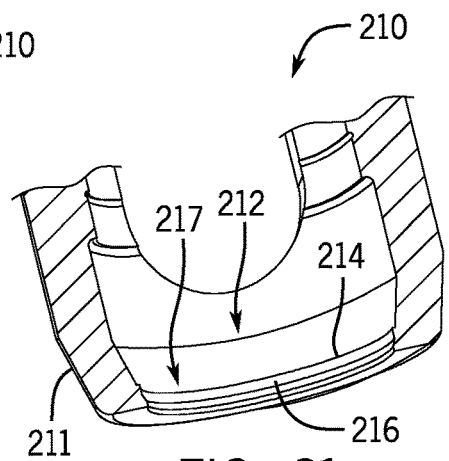
FIG. 61
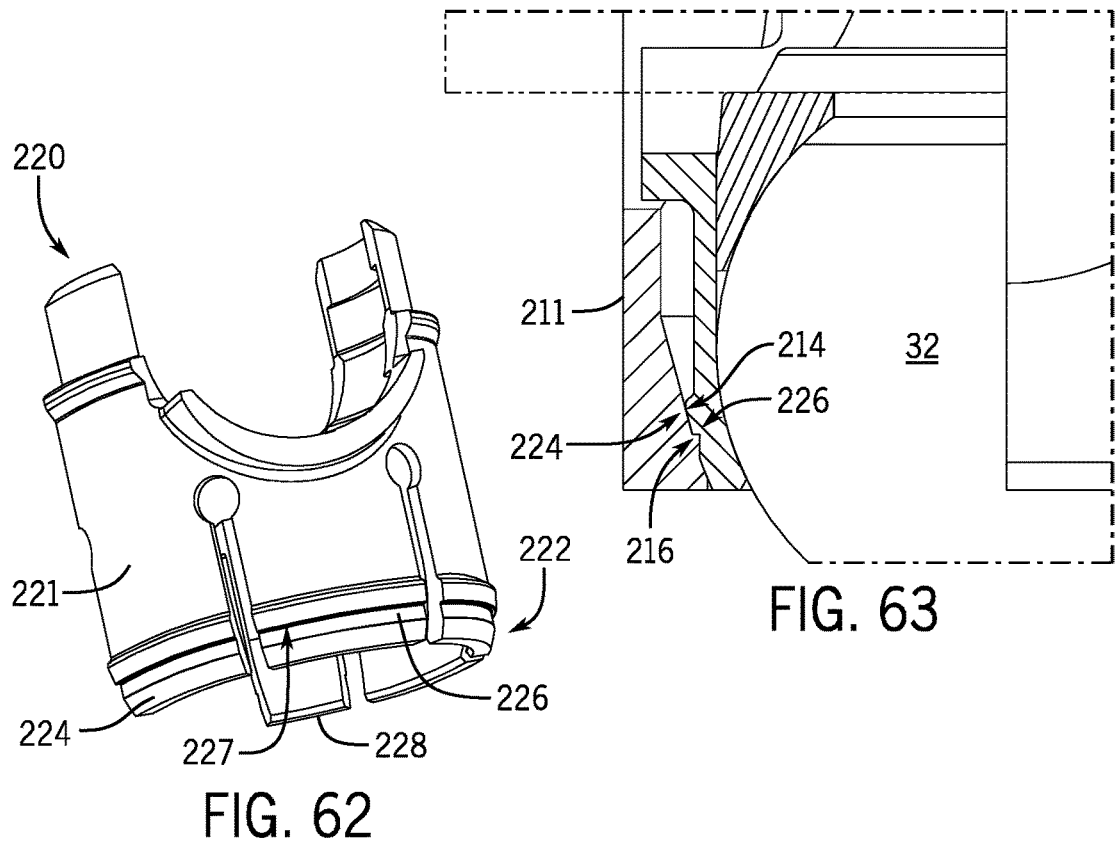
FIG. 62
FIG. 63

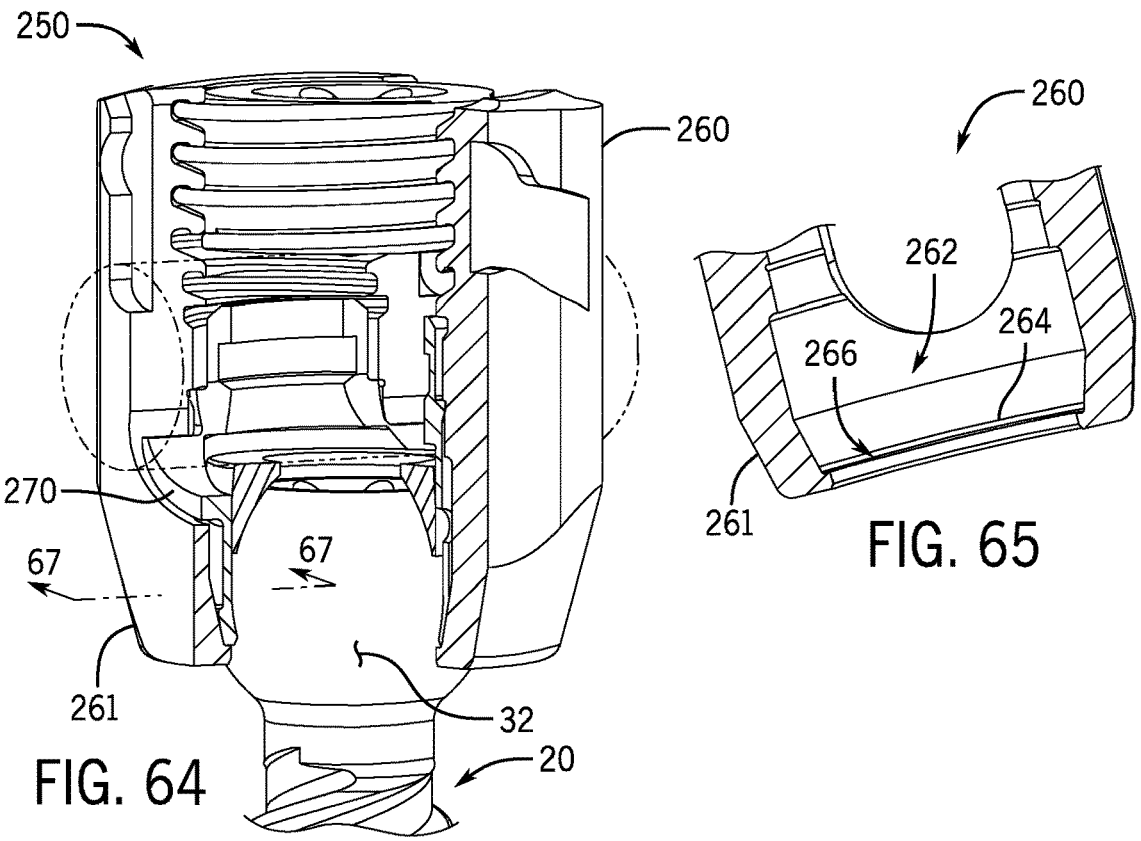
FIG. 64
FIG. 65
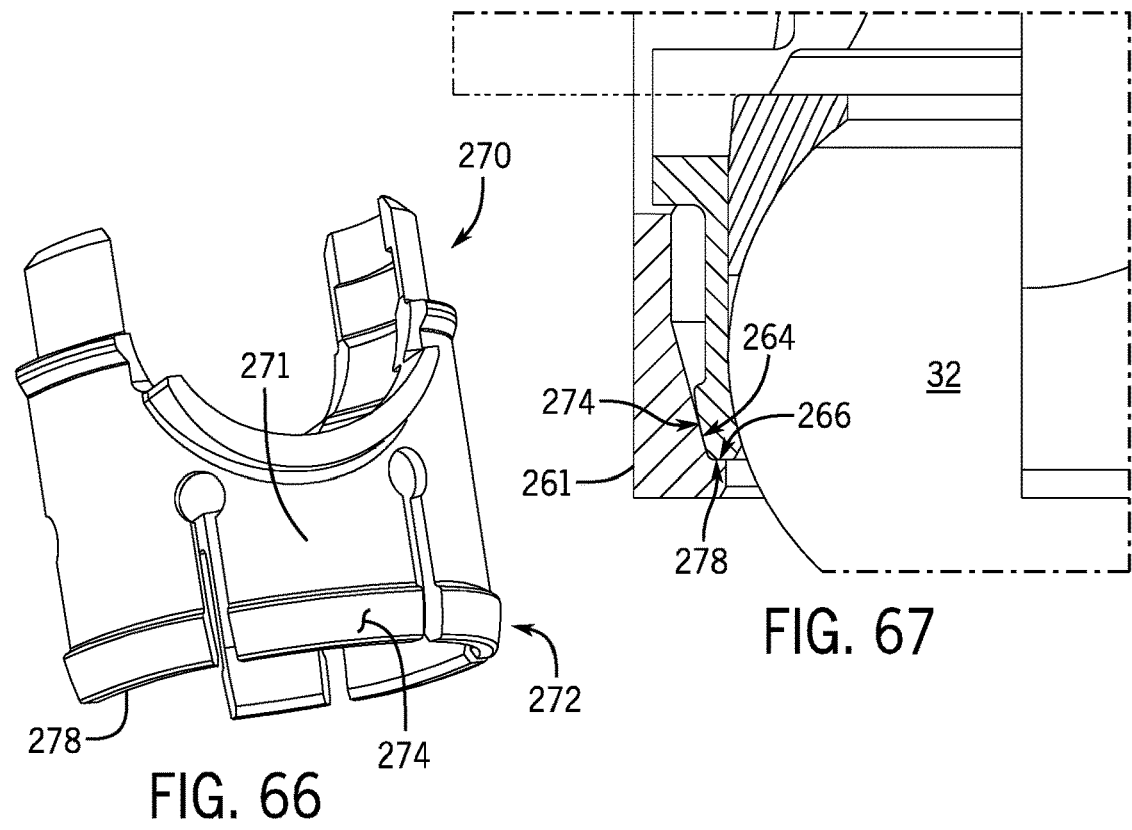
FIG. 66
FIG. 67

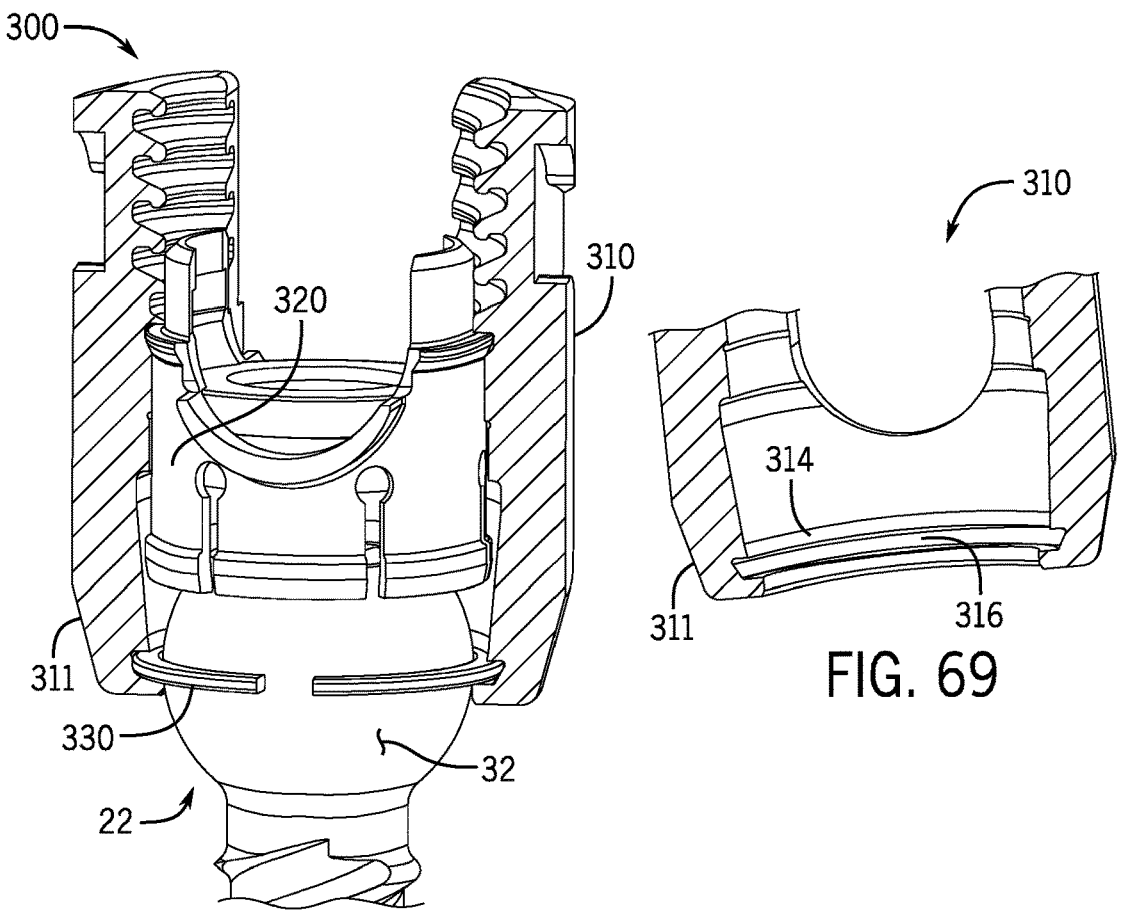
FIG. 68
FIG. 69
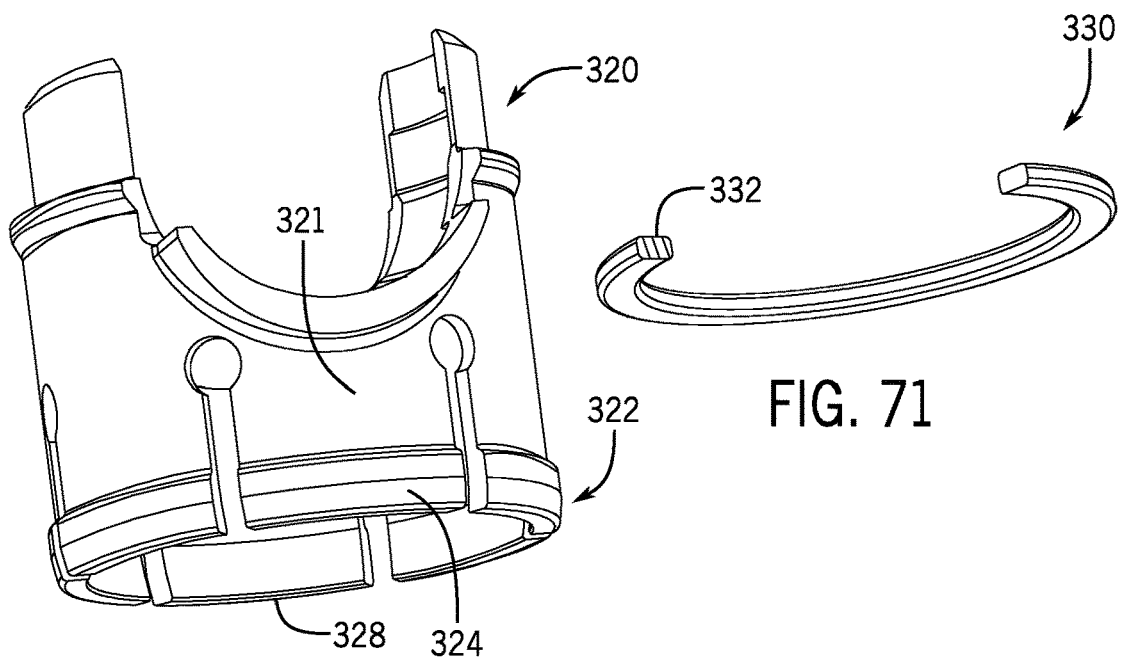
FIG. 70
FIG. 71

BONE ANCHOR ASSEMBLY HAVING A TOOL DEPLOYABLE INSERT IN COMPRESSIVE OVERLAPPING ENGAGEMENT WITH A RETAINER

CROSS-REFERENCE TO RELATED APPLICATIONS

This application is a continuation of U.S. patent application Ser. No. 17/564,784, filed Dec. 29, 2021, now U.S. Pat. No. 11,497,533, which is a continuation of U.S. patent application Ser. No. 16/686,122, filed Nov. 16, 2019, now U.S. Pat. No. 11,234,738 which claims the benefit of U.S. Provisional Application No. 62/768,732, filed Nov. 16, 2018, and U.S. Provisional Application No. 62/811,250, filed Feb. 27, 2019, each of which is incorporated by reference in its entirety herein, and for all purposes.

FIELD OF THE INVENTION

The present invention generally relates to pivotal bone anchor assemblies for use in bone surgery, particularly spinal surgery.

BACKGROUND

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw.

Typical open-ended bone screws include a threaded shank with a pair of parallel projecting branches or arms which form a yoke defining slot or channel having different shapes, such as U-shaped and square shaped, for example, to receive a rod. Hooks and other types of connectors, as are used in spinal fixation techniques, may also include open ends for receiving rods or portions of other structure.

A common mechanism for providing vertebral support is to implant bone screws into certain bones which then in turn support a longitudinal structure such as an elongate rod, or are supported by such a rod. Bone screws of this type may have a fixed head or receiver relative to a shank thereof. In the fixed bone screws, the rod receiver head cannot be moved relative to the shank and the rod must be favorably positioned in order for it to be placed within the receiver head. This is sometimes very difficult or impossible to do. Therefore, pivotal or polyaxial bone screws are commonly preferred. Open-ended polyaxial bone screws typically allow for pivoting and rotation of the separate receiver about the shank in one or more planes until a desired rotational position of the receiver is achieved by fixing such position relative to the shank during a final stage of a medical procedure when an elongate rod or other longitudinal connecting member is inserted into the receiver, followed by a locking set screw or other closure.

SUMMARY

Briefly described, one embodiment of the present disclosure comprises a pivotal bone anchor assembly for securing an elongate rod to patient bone. The pivotal bone anchor system generally includes a shank having a head and an anchor portion, a receiver having an axial bore and an open channel for receiving the elongate rod, and a collet insert that is top loadable into a first upper position within the axial bore of the receiver. The collet insert includes a lower collet-type chamber or pocket for receiving the shank head. The bone anchor assembly also includes a pressure ring that is uploadable into the collet pocket prior to the shank head, and having an upper surface for engaging the elongate rod. After receiving the shank head within the collet pocket below the pressure ring, the collet insert and pressure ring are downwardly deployable together with the shank head into a second position within the axial bore to capture the shank head within the bone anchor assembly. With the collet insert in the second position, the pressure ring is operable to transfer an applied pressure from the elongate rod positioned in the open channel to the shank head to lock an angular position of the shank relative to the receiver.

The invention will be better understood upon review of the detailed description set forth below taken in conjunction with the accompanying drawing figures, which are briefly described as follows.

BRIEF DESCRIPTION OF THE DRAWINGS

FIG. 1 is an exploded perspective view of a pivotal bone anchor assembly, in accordance with a representative embodiment of the present disclosure.

FIG. 2 is an exploded perspective view of the bone anchor of the pivotal bone anchor assembly of FIG. 1.

FIG. 3 is a cross-sectional perspective view of the shank head of the bone anchor of FIG. 2.

FIG. 4. is a perspective of the receiver of the pivotal bone anchor assembly of FIG. 1.

FIG. 5 is a cross-sectional side view of the receiver of FIG. 4.

FIG. 6 is a cross-sectional perspective view of the receiver of FIG. 4.

FIG. 7 is another cross-sectional perspective view of the receiver of FIG. 4.

FIG. 19 is an exploded perspective view of the receiver, collet insert, and internal pressure ring components of the receiver sub-assembly prior to their pre-assembly into a shipping state configuration.

FIG. 20 is a partially cut-away perspective view of the receiver of FIG. 19 with the collet insert being installed therein.

FIG. 21 is a partially cut-away perspective view of the receiver of FIG. 19 with the collet insert preassembled into its shipping state position.

FIG. 32 is a partially cut-away perspective view of the receiver sub-assembly moving further downward onto the shank head, causing the collet fingers to flex outward and the distal pocket opening to expand within the upper expansion chamber portion of the receiver cavity until the distal pocket opening reaches maximum expansion.

FIG. 33 is a sectioned perspective view of the receiver sub-assembly and shank head of FIG. 32.

FIG. 34 is a partially cut-away perspective view of the receiver sub-assembly moving further downward until the shank head reaches maximum push through within the collet pocket and the upper portion of the shank head spherical outer surface abuts the concave bottom surface of the pressure ring.

FIG. 35 is a sectioned perspective view of the receiver sub-assembly and shank head of FIG. 34.

FIG. 57 is sectioned perspective view of the receiver sub-assembly, shank head, and disassembly tool with the receiver sub-assembly being partially removed from the shank head.

FIG. 58 is close-up sectioned perspective view of the receiver sub-assembly, shank head, and disassembly tool of FIG. 57.

FIG. 59 is sectioned perspective view of the receiver sub-assembly, shank head, and disassembly tool with the receiver sub-assembly being entirely removed from the shank head.

FIG. 60 is a partially cut-away perspective view of a receiver sub-assembly, shank head, elongate rod, and closure in the fully locked configuration, in accordance with another representative embodiment of the present disclosure.

FIG. 61 is a cross-sectional perspective view of the receiver of FIG. 60.

FIG. 62 is a perspective view of the collet insert of FIG. 60.

FIG. 63 is a close-up partially cut-away side view of the receiver sub-assembly, shank head, and elongate rod of FIG. 60.

FIG. 64 is a partially cut-away perspective view of a receiver sub-assembly, shank head, elongate rod, and closure in the fully locked configuration, in accordance with yet another representative embodiment of the present disclosure.

FIG. 65 is a cross-sectional perspective view of the receiver of FIG. 64.

FIG. 66 is a perspective view of the collet insert of FIG. 64.

FIG. 67 is a close-up partially cut-away side view of the receiver sub-assembly, shank head, and elongate rod of FIG. 64.

FIG. 68 is a partially cut-away perspective view of a receiver sub-assembly, including an expansion ring, during assembly with a shank head, in accordance with yet another representative embodiment of the present disclosure.

FIG. 69 is a cross-sectional perspective view of the receiver of FIG. 68.

FIG. 70 is a perspective view of the collet insert of FIG. 68.

FIG. 71 is a perspective view of the expansion ring of FIG. 68.

Figure 8:
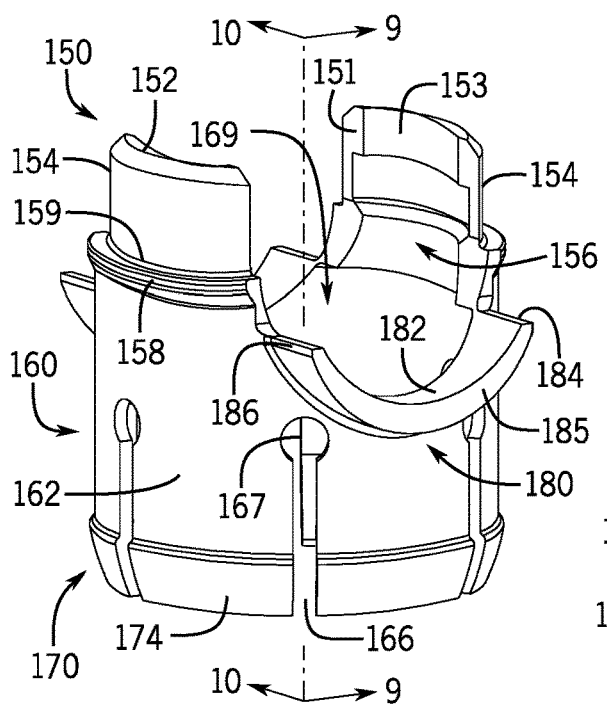
FIG. 8 is a perspective view of the collet insert of the pivotal bone anchor assembly of FIG. 1.
Figure 10:
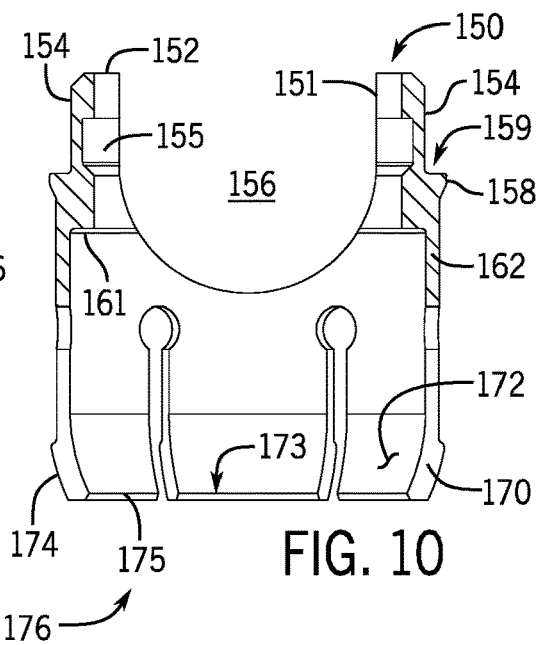
FIG. 10 is a cross-sectional side view of the collet insert of FIG. 8.
Figure 11:
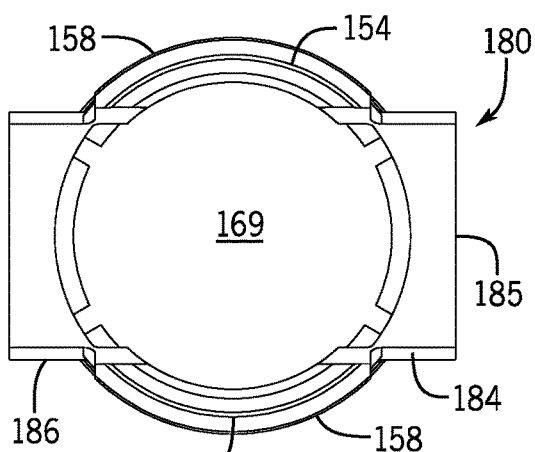
FIG. 11 is a top view of the collet insert of FIG. 8.
Figure 9:
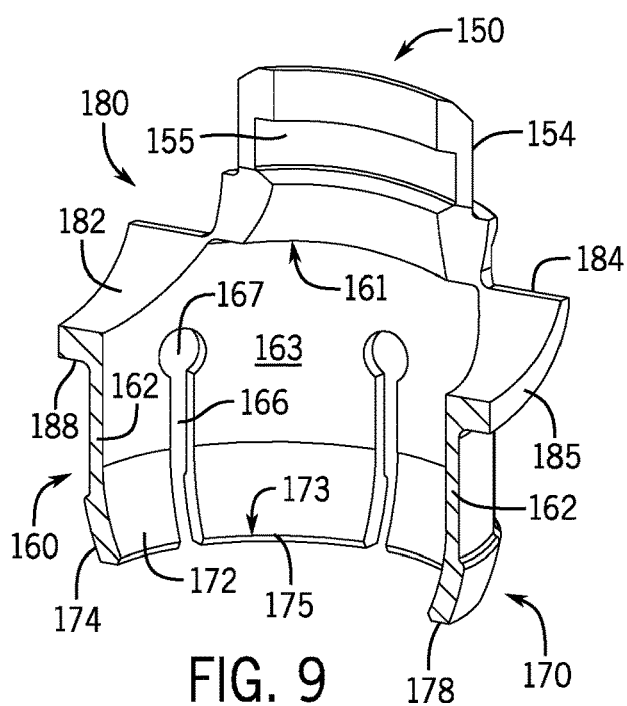
FIG. 9 is a cross-sectional perspective view of the collet insert of FIG. 8.
Figure 12:
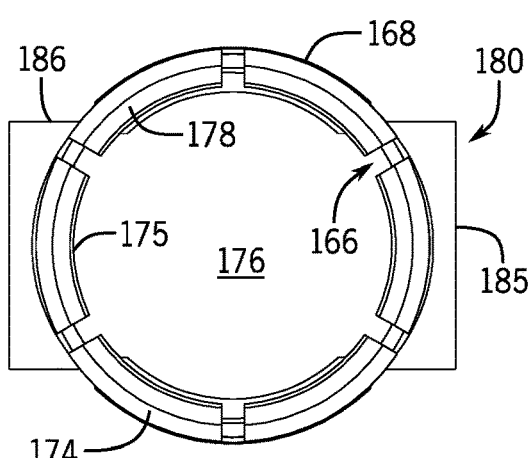
FIG. 12 is a bottom view of the collet insert of FIG. 8.

Those skilled in the art will appreciate and understand that, according to common practice, various features and elements of the drawings described above are not necessarily drawn to scale, and that the dimensions and relative positions between the features or elements may be expanded, reduced or otherwise altered to more clearly illustrate the various embodiments of the present disclosure depicted therein.

DETAILED DESCRIPTION

The following description, in conjunction with the accompanying drawings described above, is provided as an enabling teaching of exemplary embodiments of a pivotal bone anchor apparatus or assembly, together with methods for assembling and using the pivotal bone anchor apparatus or assembly. As described below, the apparatuses, assemblies, and/or methods of the present disclosure can provide several significant advantages and benefits over other pivotal bone anchors known in the art. However, the recited advantages are not meant to be limiting in any way, as one skilled in the art will appreciate that other advantages may also be realized upon practicing the present disclosure.

Furthermore, those skilled in the relevant art will recognize that changes can be made to the described embodiments while still obtaining the beneficial results. It will also be apparent that some of the advantages and benefits of the described embodiments can be obtained by selecting some of the features of the embodiments without utilizing other features, and that features from one embodiment may be interchanged or combined with features from other embodiments in any appropriate combination. For example, any individual or collective features of method embodiments may be applied to apparatus, product or system embodiments, and vice versa. Accordingly, those who work in the art will recognize that many modifications and adaptations to the embodiments described are possible and may even be desirable in certain circumstances, and are a part of the disclosure. Thus, the present disclosure is provided as an illustration of the principles of the embodiments and not in limitation thereof, since the scope of the invention is to be defined by the claims.

Referring now in more detail to the drawing figures, wherein like parts are identified with like reference numerals throughout the several views, FIG. 1 illustrates a representative embodiment of a pivotal bone anchor apparatus or assembly 10 (hereinafter referenced to as "the assembly 10") for securing an elongate rod to patient bone in spinal surgery. The assembly 10 generally includes a bone anchor, such as shank 20, having a capture portion, such as shank head 22, at a proximal end 23, and an anchor portion or shank body 40 extending distally from the shank head 22 for securement to patient bone. The assembly also generally includes a receiver 100 having an internal cavity 126 in a base portion 134 and two upright arms 104 extending upwardly from the base portion to define a rod channel 106 for receiving an elongate rod 70. The receiver 100 can be initially pivotably secured to the shank head 22 with a number of separate internal components that have been pre-assembled into the internal cavity 126 and the rod channel 106 to form a receiver sub-assembly 14. These components generally include a collet insert 150 and a pressure ring 190. After an elongate rod 70 has been positioned within a lower portion of the rod channel 106, a closure 50 can be threadably or otherwise secured into an upper portion of the rod channel 106 to apply pressure to an upper surface of the elongate rod 70, which in turn applies pressure to the upper surface of the pressure ring 190, thereby locking both the elongate rod 70 and the pivotal bone anchor assembly 10 into a final locked position. As discussed in more detail below, the shank head 22 is configured to provide a multi-planar pivotable connection between the shank 20 and the receiver sub-assembly 14 prior to fixing the shank 20 in a desired position with respect to the receiver sub-assembly 14.

With reference to FIGS. 2-3, the bone anchor or shank 20 generally comprises the capture portion or shank head 22 at a proximal end 23, and an anchor portion or shank body 40 extending distally from the shank head 22 toward a tip 48 at a distal end 49. The shank 20 is elongate, with the shank body 40 having a helically wound bone implantable thread 44 (single, dual, or multiple-lead thread form) extending from near a neck 42 located adjacent to the shank head 22, to a distal tip 48 of the body 40 and extending radially outwardly therefrom. During use, the shank body 40 utilizing the thread 44 for gripping and advancement is implanted into the vertebra (not shown) of a patient leading with the tip 48 and driven down into the vertebra with an installation or driving tool (also not shown), so as to be implanted in the vertebra to near the neck 42 of the shank 20, as more fully described in the paragraphs below. The shank 20 has a longitudinal axis, or axis of rotation, that is generally identified by the reference numeral 21.

The non-threaded neck 42 extends axially upward from the shank body 40. The neck 42 may be of the same or is typically of a slightly reduced radius as compared to an adjacent upper end of the shank body 40 where the thread 44 terminates, with the reduced radius providing for increased angulation of the receiver sub-assembly 14 relative to the shank. In one aspect the threaded shank body 44 and the non-threaded neck 42 can together define an anchor portion of the shank 20.

Extending further axially upwardly and outwardly from the neck 42 is the shank head 22 that provides a connective or capture structure disposed at a distance from the shank body 40, and thus at a distance from the vertebra when the shank body 40 is implanted in such vertebra. The shank head 22 of the pivotal bone anchor assembly 10 generally has a partial spherical shape defining a hemisphere plane 30 at a maximum width perpendicular to the longitudinal axis, and a partial spherical outer surface 32 extending above and below the hemisphere plane. As shown in the drawings, the partial spherical outer surface 32 may have a single common radius as it extends above the hemisphere plane 30 to an annular planar top surface 24 and an internal driving tool engagement structure 26 formed into the top of the shank head 22, and as it extends below the hemisphere plane 30 to the neck 42. It is foreseen, however, that other shapes and/or configurations for the shank head 22 are also possible and considered to fall within the scope of the present disclosure.

Located adjacent to the partial spherical outer surface 28 is an annular planar top surface 24 that surrounds an internal drive feature 26 or drive socket. The illustrated internal drive feature 26 is an aperture formed in the top surface 24, and in one aspect can be a multi-lobular or star-shaped aperture, such as those sold under the trademark TORX, or the like, having internal faces 28 designed to receive a multi-lobular or star-shaped tool for rotating and driving the shank body 40. It is foreseen that such an internal tool engagement structure 26 may take a variety of tool-engaging forms and may include one or more apertures of various shapes, such as a pair of spaced apart apertures or a hex shape designed to receive a hex tool (not shown) of an Allen wrench type. The seat or base surface 27 of the drive feature 26 can be disposed perpendicular to the shank axis 21, with the drive feature 26 otherwise being coaxial with the axis 21. In operation, a driving tool is received in the internal drive feature 26, being seated at the base surface 27 and engaging the internal faces 28 of the drive feature 26 for both driving and rotating the shank body 40 into the vertebra, either before or after the shank 20 is attached to the receiver sub-assembly 14, with the shank body 40 being driven into the vertebra with the driving tool extending into the receiver 100.

In one aspect the shank 20 can be cannulated, with a bore 46 extending through the entire length thereof, and centered about the longitudinal axis 21 of the shank 20. The bore 46 is defined by an inner cylindrical wall 47 of the shank 20 and has a circular opening at the shank tip 48 and an upper opening communicating with the internal drive 26 at the seat surface 27. The bore 46 is coaxial with the threaded shank body 40 and the shank head 22. The bore 46 provides a passage through the shank 20 interior for a length of wire (not shown) inserted into the vertebra prior to the collet insertion of the shank body 40, the wire providing a guide for insertion of the shank body 40 into the vertebra. The bore can also provide for a pin to extend therethrough and beyond the shank tip, the pin being associated with a tool to facilitate insertion of the shank body into the vertebra.

To provide a biologically active interface with the bone, the threaded shank body 40 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_9)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Figure 47:
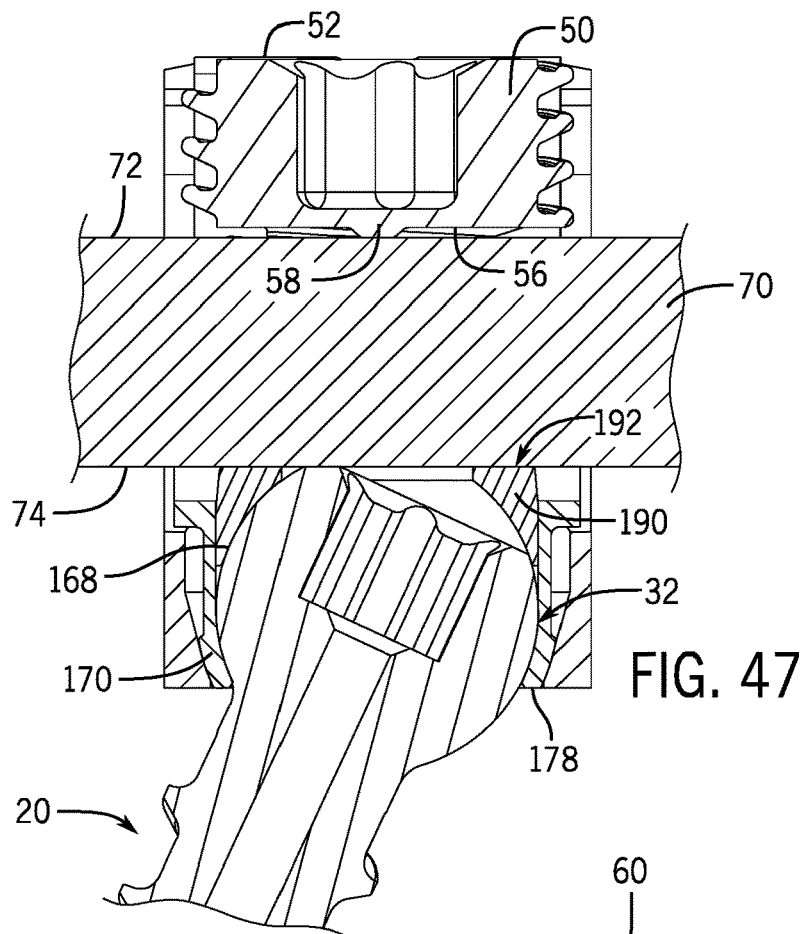
FIG. 47 is a sectioned side view of the receiver sub-assembly, shank head, elongate rod, and closure in the fully locked configuration of FIG. 44, with the bone anchor being pivoted relative to the receiver.
Figure 48:
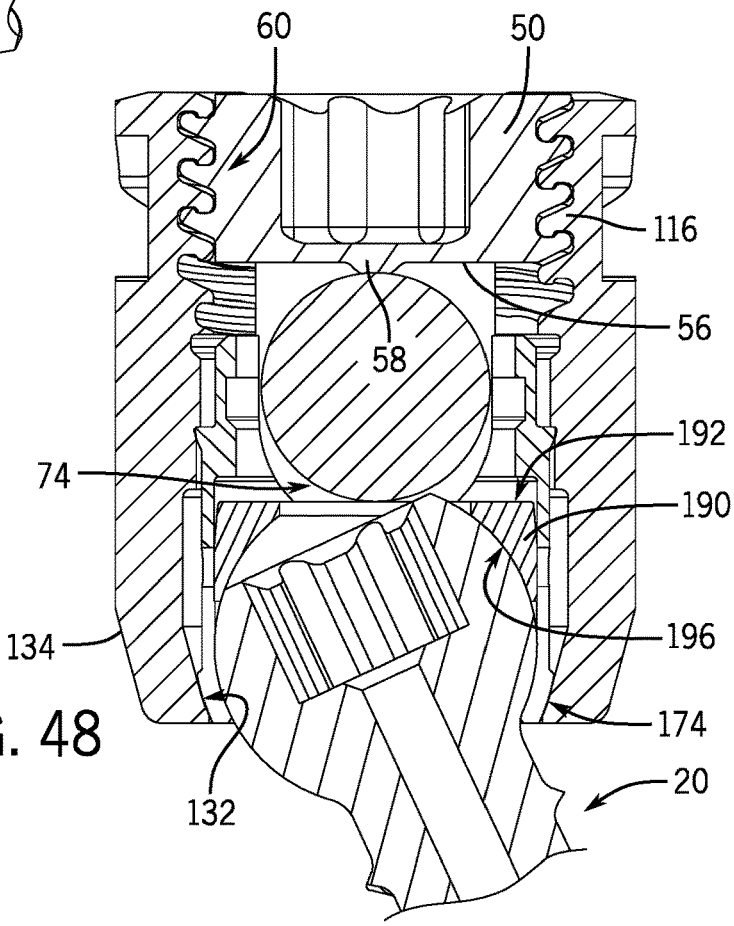
FIG. 48 is another sectioned side view, orthogonal to FIG. 47, of the receiver sub-assembly, shank head, elongate rod, and closure in the fully locked configuration of FIG. 44, with the bone anchor being pivoted relative to the receiver.

Illustrated in FIGS. 4-7 is the receiver 100 of the pivotal bone anchor assembly 10 having a generally U-shaped appearance with a partially discontinuous substantially cylindrical inner profile and a partially-cylindrical and partially-faceted outer profile, although other profiles are contemplated. The receiver 100 also has a longitudinal axis 101, or axis of rotation, that is shown in FIG. 1 as being aligned with the longitudinal axis 21 of the shank 20, such orientation being desirable, but not required during assembly of the receiver 100 with the shank 20. After the receiver 100 is pivotally attached to the shank head 22, either before or after the shank 20 is implanted in a vertebra, the receiver axis 101 is typically disposed at an angle with respect to the shank axis 21 as shown, for example, in FIGS. 47-48.

The receiver 100 includes a substantially cylindrical base 134 integral with a pair of opposed upright arms 104 forming an upwardly open channel 106 between the arms 104 for receiving the elongate rod 70. Each of the receiver arms 104 has an interior face 110 that includes a discontinuous upper portion of a generally cylindrical axial or central bore 114 that extends from the top surfaces 102 of the upright arms 104 at the proximal end 103 of the receiver 100, downwardly through the open channel 106 and the base 134 to a bottom opening 136 at the distal end 139 of the receiver 100. The channel portion or upper discontinuous portion of the central bore 114 is bounded on either side by opposing parallel planar surfaces 112 that curve downwardly into U-shaped lower saddle surfaces 113, with the upper opposing planar surfaces 112 and lower saddle surface 113 defining the front and back ends of the upwardly open U-shaped channel 106. In one aspect of the present disclosure the receiver can include breakoff extensions (not shown) extending upwardly from the top surfaces 102 of the upright arms 104, and which can be threaded for threadable engagement with the outer threads of the closure 50 (FIGS. 15-18).

The upper discontinuous portion of the cylindrical central bore 114 further includes a partial helically wound guide and advancement structure 116 extending radially inwardly from the interior face 110 of the channel 106 and located adjacent the top surfaces 102 of the arms 104. In the illustrated embodiment, the guide and advancement structure 116 is a partial helically wound interlocking flangeform configured to mate under rotation with a similar structure on the closure 50 (FIGS. 15-18), as described more fully below. However, it is foreseen that the guide and advancement structure 116 could alternatively be a square-shaped thread, a buttress thread, a modified buttress thread, a reverse angle thread or other thread-like or non-thread-like helically wound discontinuous advancement structure for operably guiding under rotation and advancing the closure 50 downward between the arms 104, as well as eventual torqueing when the closure 50 abuts against the elongate rod 70. Additionally, the various structures and surfaces forming the guide and advancement structure 116 can be configured to resist, to inhibit, to limit, or to preferentially control the splay of the upright arms 104 under the rotation and advancing the closure 50 downward between the arms 104.

The upper discontinuous portion of the cylindrical central bore 114 immediately below the guide and advancement structure 116 is defined by a discontinuous cylindrical surface 118 that extends downward from the guide and advancement structure 116 to an expansion chamber portion 128 of the receiver cavity 126. Formed into the discontinuous cylindrical surface 118 is an upper "shipping state" groove 120 spaced below the guide and advancement structure 116, and a lower "capture/locking state" groove 122 located between the upper groove 120 and the receiver cavity 126. In one aspect the upper groove 120 may be deeper and wider than the lower groove 122.

Communicating with and located beneath the channel 106 of the receiver 100 at the base portion 134 thereof is the cavity 126 having an upper expansion chamber portion 128 and a lower seating surface portion 132 located proximate the bottom opening 136. The expansion chamber 128 is generally defined by an upper discontinuous downwardly-facing annular step surface 125 demarking the bottom of the discontinuous cylindrical surface 118, a lower transition surface 130, and a substantially cylindrical sidewall surface 127 extending between the upper step surface 125 or the U-shaped saddle surfaces 113 of the channel 106 and the lower transition surface 130. The diameter of the cylindrical sidewall surface 127 is generally greater than the diameter of the discontinuous cylindrical surface 118 immediately above the upper expansion chamber portion 128. Furthermore, the lower transition surface 130 may have a downwardly and inwardly tapered, or frusto-conical, profile, or an inwardly curved profile, or similar. The lower transition surface 130 is generally not intended to be engaged by the collet insert during assembly and use, and serves primarily as a transition structure between the upper expansion chamber portion 128 and the partial spherical interior seating surface 132 while providing material strength for supporting the partial spherical interior seating surface 132 relative to the upper portion of the receiver base 134.

The lower seating surface portion 132 of the cavity 126 is spaced below the expansion chamber 128 by the frusto-conical transition surface 13, and can be a continuous partial spherical seating surface extending 360 degrees around the lower circumference of the receiver cavity 126. As described in detail below, the partial spherical seating surface 132 of the receiver 100 is configured for frictional engagement with a plurality of outer partial spherical surfaces of the distal tip sections 170 of a collet insert 150 (FIGS. 8-12) when a downwardly directed pressure is applied to a shank head that is captured within the collet insert 150, as well as for releasing the engagement with the distal tip sections 170 when the pressure is removed.

Immediately below the seating surface 132 is a lowermost cylindrical surface 135 that generally defines the bottom opening 136 that communicates with both the internal cavity 126 and a receiver lower exterior or bottom 138 of the base 134. The cylindrical surface 135 is substantially coaxially aligned with respect to the longitudinal axis 101 of the receiver 100, and is also sized and shaped to be smaller than the distal tip sections of the collet insert 150 when the shank head 22 is captured within the collet insert 150, so as to form a restriction to prevent the shank head 22 from passing downward through the cavity 126 and out the bottom opening 136 of the receiver 100 during the use of the pivotal bone anchor assembly.

As noted above, the outer surface 108 of the receiver 100 can have a partially-cylindrical and partially-faceted outer profile. In the embodiment of the receiver 100 illustrated in FIGS. 3-7, the faceted or planar portions can include front and back outer planar faces 140 on the receiver base 134 below the open channel 106 and extending upward along the side edges of the upright arms 104 to the top surfaces 102 of the arms. In addition, a pair of tool receiving and engaging recesses 142 can be formed into the side outer faces 107 between each top surface 102 and the receiver base 134, and can have recessed surfaces that are perpendicular with the front and back outer planar faces 140. In one aspect additional front and back tool receiving and engaging recesses 144 can be formed into the upper arm portions of the front and back outer planar faces 140. The faceted or planar portions 140 of the outer surface 108 of the receiver 100 and the tool receiving and engaging recesses 142, 144 can serve together as outer tool engagement surfaces that allow for tooling to securely engage and hold the receiver 100 during an initial pre-assembly with the separate collet insert 150 and pressure ring 190 into the receiver 100 to form the receiver sub-assembly 14, as well as during coupling of the receiver sub-assembly 14 to the shank 20 after or before the implantation of the shank body 40 into a vertebra, and during further assembly of the assembly 10 with the elongate rod 70 and the closure 50.

Although the rod channel 106 is shown as being an upwardly-open channel in the embodiment of the bone anchor receiver 100 shown in FIGS. 1 and 4-7, it will be appreciated by one of skill in the art that in other embodiments the receiver may be a closed top receiver, with the rod channel becoming a rod aperture, and in which the elongate rod is introduced into the receiver from the side rather than from the top. This feature may be especially useful when implanting a long series of pivotal bone anchor assemblies along a patient's spine, and it is determined that it would be beneficial to use a closed top receiver at one end to better secure the elongate rod at the beginning of the series.

It is foreseen, moreover, that other shapes and configurations for the interior and exterior surfaces of the receiver 100, different from those shown in the drawings while providing for similar interaction and functionality of the various components of the pivotal bone anchor assembly, are also possible and considered to fall within the scope of the present disclosure. For example, the tool receiving and engaging recesses 142, 144 may be replaced by horizontally-extending "top notch" type tool receiving grooves formed around the upper periphery of the receiver arms 104, or additional planar faces formed into the side outer surfaces 107 of the receiver 100 (which may or may not be orthogonal to the front and back outer planar faces 140 on the receiver base 134) are also possible. Additional tool engaging structures or recesses can also be formed on the outer faces of breakoff extensions described above.

Illustrated in FIGS. 8-12 is the collet insert 150 having a lower, generally tubular collet portion 160 that defines an expandable internal chamber or collet pocket 164, with integral insert arms 154 projecting upwardly or proximally from the collet portion 160 to define an insert channel 156 that is alignable with the receiver channel 106 upon installation of the collet insert 150 into the receiver 100. The interior surfaces of the insert arms 154 include opposed parallel planar surfaces 151 that curve downwardly into U-shaped upper surfaces 182 of opposed radial extensions 180 that project radially outward from the tubular collet portion 160 between the insert upright arms 154. The opposed parallel planar surfaces 151 are located on either side of a discontinuous upper cylindrical surface 153 formed into the interior center portion of the insert arms 154 to define a central tool receiving aperture 169. The central tool receiving aperture 169 extends vertically downward through the collet insert channel 156 and the upper end of the collet portion 160 (and through the central aperture of the pressure ring (FIGS. 13-14)) to allow passage for a driving tool to engage the internal drive feature 24 or drive socket formed into the top of a shank head 22 that is captured within the collet pocket 164. As illustrated in the drawings, the central tool receiving aperture 169 can be smooth and non-threaded.

Figure 44:
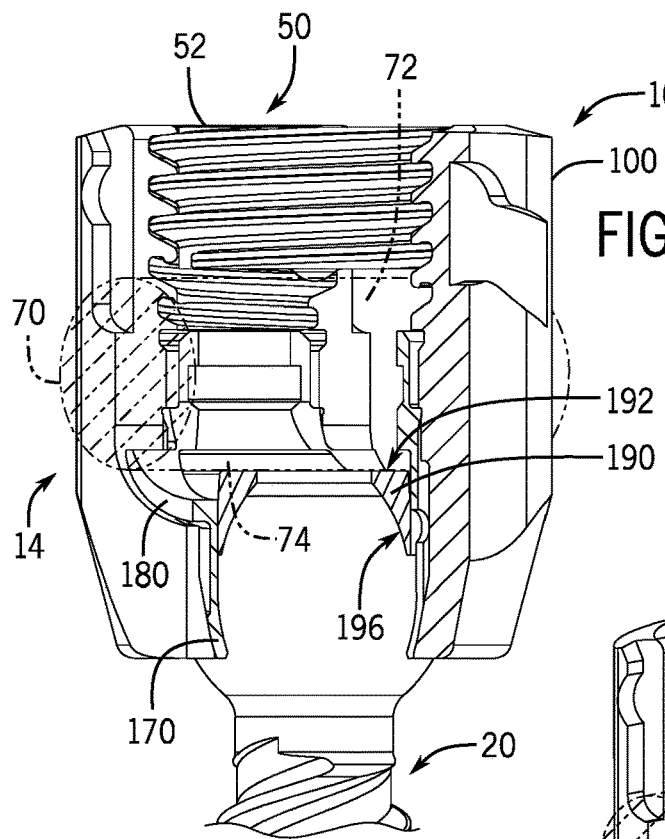
FIG. 44 is a partially cut-away perspective view of the receiver sub-assembly and coupled shank head, and further with an elongate rod and closure, in a fully locked configuration.
Figure 45:
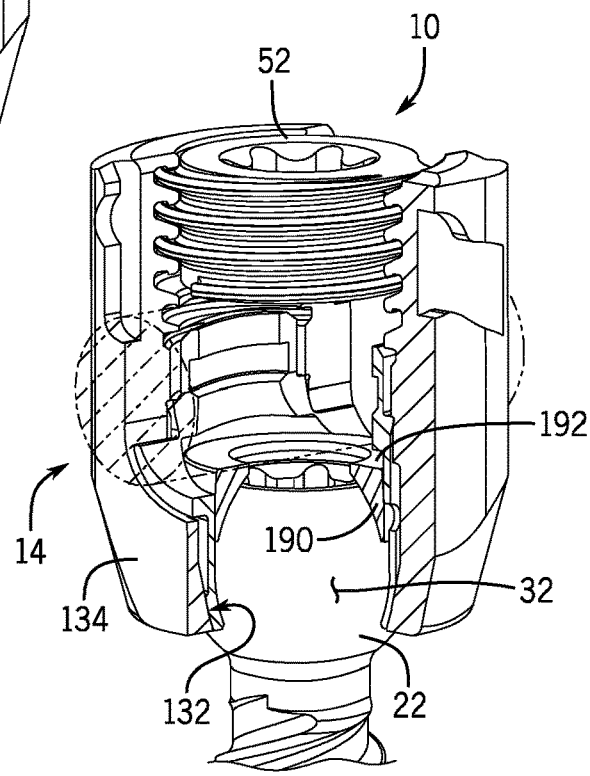
FIG. 45 is a sectioned perspective view of the receiver sub-assembly, shank head, elongate rod, and closure in the fully locked configuration of FIG. 44.

The insert arms 154 have a width between the opposed parallel planar surfaces 151 for operably snugly receiving the elongate rod 70. Furthermore, the insert arms 154 extend upwardly from the collet portion 160 to top surfaces 152 that, in one aspect, are spaced below a top surface of an elongate rod 70 when the rod is positioned in the insert and receiver channels 156, 106 (see FIGS. 44-45). The discontinuous upper cylindrical surface 153 of the insert arms 154 further includes an internal tool engagement structure or recesses 155 formed therein that are spaced below the top surfaces 152 of the insert arms 154. For purposes described in more detail below, the internal tool engagement structure 155 is configured for engagement with tooling, such as an extraction tool or a deployment tool (not shown). Although shown as a recess 155 with smooth surfaces, in other embodiments the upper tool engagement structure could be threaded, with the tooling also being threaded at a distal end thereof Protruding radially outwardly from the outer side surfaces 157 of the insert arms 155 are opposed lateral ridges 158 that are configured for "snap-in" engagement with the upper grooves 120 and with the lower grooves 122 formed into the interior faces 110 of the receiver upright arms 104 when the receiver sub-assembly is in a pre-assembled shipping state position or the capture/locking state position, respectively. The protruding lateral ridges are non-threaded, and in one aspect a small rounded relief groove 159 can be formed at the junction between the vertical outer side surfaces 157 of the collet insert arms 152 and the top surfaces of the opposed lateral ridges 158, for reasons described in more detail below. It is foreseen that the arrangement of protruding ridges and recesses on the collet insert 150 and the receiver 100, respectively, can be reversed, with the shipping and locking recesses being formed into the exterior or outer surface of the collet insert 150 and the internal ridges protruding inwardly from the receiver central bore 114. Other combinations of ridges and grooves, or entirely different structures, including but not limited to ratchets, a separate snap ring, and the like, are also possible.

In the embodiment of the collet insert 150 illustrated in FIGS. 8-12, the opposed radial extensions 180 project radially outward from the tubular collet portion 160 between the insert upright arms 154 to end surfaces 185, and can serve to perform a number of useful functions. For example, the radial extensions 180 can include substantially planar side edge surfaces 186 that are configured to slidably engage with the upper opposing planar surfaces 112 of the receiver upright arms 104, so as to align the open insert channel 156 with the open receiver channel 106. The radial extensions 180 can also include top edge surfaces 186 that are substantially planar or flat, and which can be configured to at least partially receive the deployment tooling (not shown) used to drive the collet insert 150 downward within the receiver central bore 114 during deployment from the pre-assembled shipping state position to the capture/locking state position, as described below.

The upper surfaces 182 of the radial extensions 180 can also be curved to match the underside of the elongate rod 70. However, it will be appreciated that the underside surfaces 92 of the elongate rod 70 generally do not contact the upper surfaces 182 of the radial extensions 180, in order to restrict or prevent the creation of an alternative load path from the elongate rod 70 down into the receiver body 100 other than the load path defined by the pressure ring 190. Thus, the upper surfaces 182 of the radial extensions 180 may be shaped to match the curvature of the elongate rod so as to provide increased and uniform spacing between the two curved surfaces, so as to better avoid accidental contact during assembly and use.

Similarly, the lower or underside surfaces 188 of the radial extensions 180 can also be curved to match with the curved saddle surfaces 113 extending between the receiver upright arms 104, thereby allowing for an increased range of vertical movement between the two surfaces. Generally, the curved underside surfaces 188 of the radial extensions 180 are maintained in a position that is spaced above the curved saddle surfaces 113, in order to restrict or prevent the creation of an alternative load path between the collet insert 150 and the receiver body 100 other than the load path defined by the opposed lateral ridges 158 and the distal tips sections 170, as described in detail below. Alternatively, it is contemplated that the curved underside surfaces 188 can be configured to engage with the curved saddle surface 113 as an indexing surface, so as to align the distal tip sections 170 with the partial spherical seating surface 132 of the receiver cavity 126, and/or to provide additional support for the radial extensions 180.

As noted above, the collet portion 160 has a generally tubular construction with substantially cylindrical sidewalls 162 having inner surfaces 163 defining an expandable internal chamber or collet pocket 164 for receiving and engaging both the pressure ring 190 and the shank head 22. The proximal or upper portion of the collet pocket 164 is defined by a discontinuous, downward-facing stop surface or shelf surface 161 that extends radially outward below the discontinuous upper cylindrical surface 153, and which serves as the internal bottom surface of the upright insert arms 154. Moving downward from the downwardly-facing stop surface 161, a plurality of longitudinal slots 166 are formed through the sidewalls 162 of the collet portion 160 that sub-divide the collet portion into a plurality of resilient collet fingers 168. The upper ends of the slots 166 can terminate in rounded stress-relieving apertures 167, including but not limited to circular and oval shapes. The resilient collet fingers 168 are configured to maintain their downward orientation except when deflected outwardly by the passage of the shank head 22 or pressure ring 190, as described in detail below.

Distal tip sections 170 curve inwardly at the lower ends of the resilient collet fingers 168 to partially close the distal end 179 of the expandable collet pocket 164 and to define an expandable distal pocket opening 176 that returns to its nominal shape after deflection by the passage of the shank head 22 or pressure ring 190. The inner portions of the distal tip sections 170 define a plurality of inner partial spherical surfaces 172 that engage the spherical outer surface 32 of the shank head 22 below the hemisphere plane 30. The outer portions of the distal tip sections 170 define a plurality of outer partial spherical surfaces 174 that are configured to engage the partial spherical interior seating surface 132 of the receiver cavity 126, generally without contraction or inward displacement of the collet fingers 168, when the collet insert 150 is in the capture/locking state position. Extending between the inner partial spherical surfaces 172 and the bottom surfaces 178 of the distal tip sections 170 are chamfered surfaces 175 that can engage the upper outer edge of the pressure ring or the spherical outer surface of the shank head to facilitate the uploading of the pressure ring and shank head, respectively, into the expandable collet pocket 164. In addition, the junction between the inner partial spherical surfaces 172 and the chamfered surfaces 175 form a plurality of innermost edges 173 that together define the size of the distal pocket opening 176. If desired, the innermost edges 173 and chamfered surface 173 can be rounded together to form rounded innermost edges that are continuously curved between the inner partial spherical surfaces 172 and the bottom surfaces 178 of the distal tip sections 170.

As can be seen in the drawings, the distal tip sections 170 can have a thickness that is greater than the thickness of the tubular sidewalls 162 of the collet portion 160, so that each of the distal tip sections has a bulbous profile. In one aspect the thickness of the distal tip sections 170 can be varied or controlled so as to better position their outer partial spherical surfaces 174 relative to the partial spherical interior seating surface 132, as well as to provide increased metallic material to support against pullout of the shank head 22 during assembly and use.

It is foreseen that other shapes and configurations for the interior and exterior surfaces of the collet insert, different from those shown in the drawings while providing for similar interaction and functionality of the various components of the pivotal bone anchor assembly, are also possible and considered to fall within the scope of the present disclosure. For example, the collet insert can be positioned within the receiver in different ways, such as being rotated in place, crimped in place, or snapped in place using different structures other than those shown in the drawings of the present disclosure, etc.

In particular, it is contemplated that the opposed radial extensions may be removed or eliminated from the collet insert, and that the collet insert can be configured for downloading into the receiver open channel with the protruding lateral ridges aligned with the receiver channel, and then rotated or twisted into position with the protruding lateral ridges engaged within the upper shipping state groove and the open insert channel coming into alignment with the open receiver channel. The amount of rotation can be about 90 degrees. In some embodiments the collet insert can be prevented from further rotation within the receiver by using crimps, a blocking tab or stop structure, and the like. It will be appreciated that the "Twist-In-Place" embodiment of the collet insert can still include downward tool deployment of the collet insert to the capture/locking state position, with the opposed lateral ridges 158 being snapped into the lower capture/locking state groove 122 following a sliding biased engagement between the opposed lateral ridges 158 of the collet insert 150 and the discontinuous cylindrical surfaces 118 of the receiver central bore 114.

Additional details and disclosure regarding deployment tools or tooling for preparing, assembling, and/or deploying bone screws and pivotal bone anchor assemblies or components thereof during spinal surgery, including a receiver sub-assembly having an insert with "Twist-In-Place" and downward tool deployment features similar to those described in the alternative above, can be found in co-pending Patent Cooperation Treaty (PCT) Application PCT/US2019/51190, filed Sep. 13, 2019, and claiming the benefit of U.S. Provisional Application No. 62/731,059, filed Sep. 13, 2018, with each of the above-referenced applications being incorporated by reference in its entirety herein and for all purposes.

Figure 13:
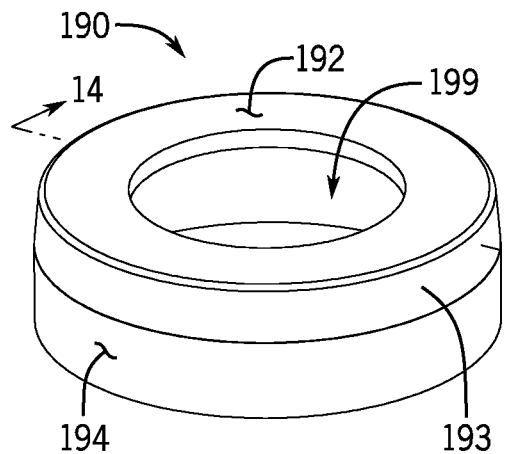
FIG. 13 is a perspective view of the internal pressure ring of the pivotal bone anchor assembly of FIG. 1.
Figure 14:
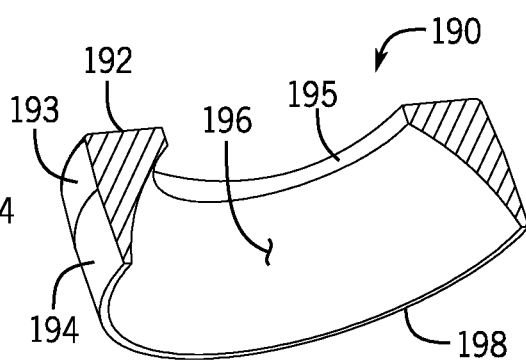
FIG. 14 is a cross-sectional perspective view of the internal pressure ring of FIG. 13.
Figure 15:
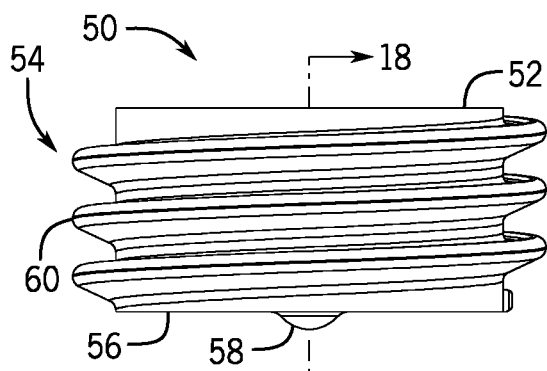
FIG. 15 is a side view of the closure of the pivotal bone anchor assembly of FIG. 1.
Figure 16:
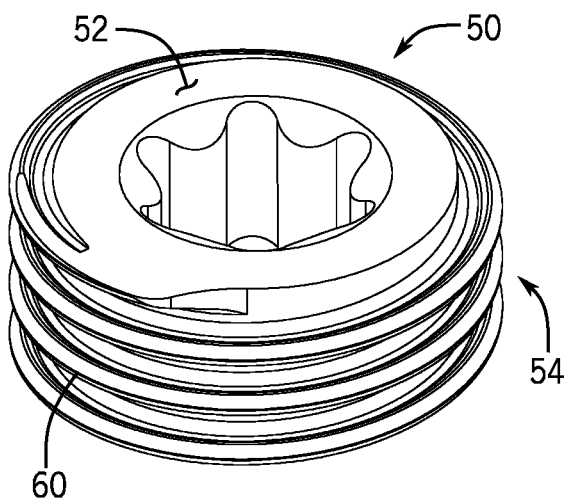
FIG. 16 is an upper perspective view of the closure of FIG. 15.
Figure 17:
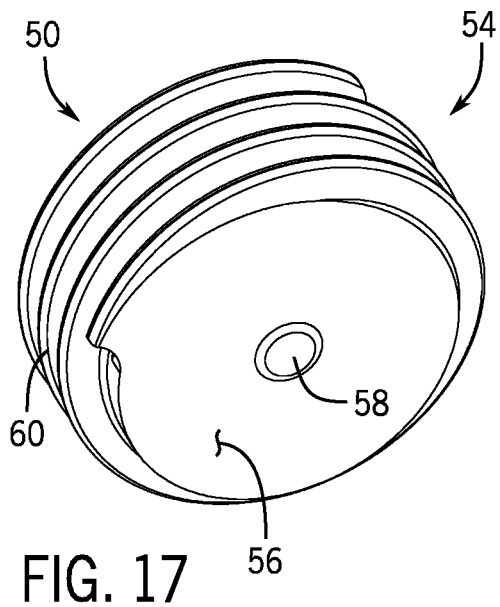
FIG. 17 is a lower perspective view of the closure of FIG. 15.
Figure 18:
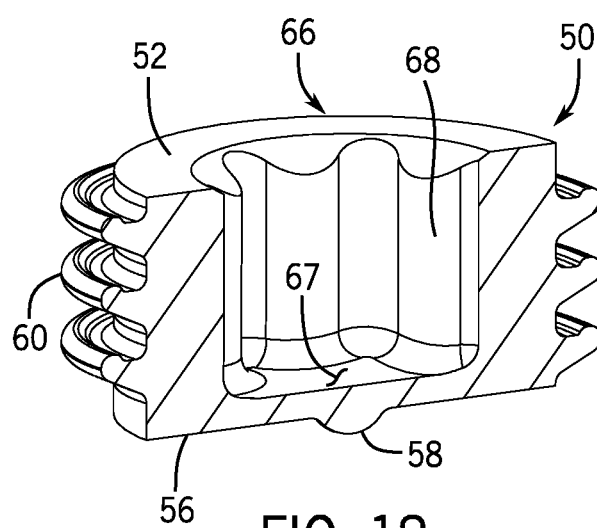
FIG. 18 is a cross-sectional perspective view of the closure of FIG. 15.

Illustrated in FIGS. 13-14 is the pressure ring 190 that is configured to transfer a downwardly-directed force from the elongate rod 70 to the spherical outer surface 32 of the shank head 22. The pressure ring 190 generally has a ring shaped body with an annular top surface 192, an annular bottom edge surface 198, and a substantially-cylindrical outer surface 194 that can be sized and shaped for slidable interference engagement with the interior sidewall surfaces of the collet pocket 164. For example, the diameter of the cylindrical outer surface 194 can be equal to or slightly greater than the inner diameter of the tubular sidewalls 162 and resilient collet fingers 168 that define the collet pocket 164, so as to provide a slight interference engagement when the pressure ring 190 is positioned in the upper portion of the collet pocket 164, with the slight interference engagement being sufficient to hold or maintain the pressure ring 190 within the collet pocket 164 in the shipping state position. In one aspect the outer surface may further include an upper tapered or relief portion 195 above the cylindrical outer surface portion 194 that limits the interference engagement to a narrow cylindrical interference region spaced below the top surface 192 of the pressure ring 190, and which can further facilitate the uploading and positioning of the pressure ring into the collet portion 160 of the collet insert 150.

The top surface 192 of the pressure ring 190 is configured to engage the bottom or lowermost or underside surface 74 of the elongate rod 70 when the elongate rod is positioned within the collet insert channel 156. As shown in the drawings, the top surface 192 can be a symmetrical substantially-planar annular surface, having a symmetrical shape that allows for uploading the pressure ring 190 into the collet pocket 164 in any rotational orientation. A central tool receiving aperture 199 is formed through the top surface 192 to allow passage of a driving tool to engage the shank head tool engagement structure 24 or drive socket that is captured within the collet pocket 164, and which central aperture 199, in one aspect, can be defined by a cylindrical inner surface 195 that is smooth and non-threaded. As discussed below, outer edge portions of the top surface 192 can abut the discontinuous downwardly-facing stop surface 161 of the collet insert 150 when the pressure ring 190 is uploaded into the shipping state configuration within the collet insert 150.

Extending between the cylindrical inner surface 195 and the annular bottom edge surface 198 of the pressure ring 190 is an inner or lower, downwardly-opening concave surface 196 that is configured to receive and mate with the spherical outer surface 32 of the shank head 22. The lower concave surface 196 can be textured, ridged, coated, and the like, to improve the frictional engagement with the spherical outer surface 32.

It is foreseen that other shapes and configurations for the pressure ring 190, different from those shown in the drawings while providing for similar interaction and functionality, are also possible and considered to fall within the scope of the present disclosure. For example, it is contemplated that alternative embodiments of the pressure ring can be slotted, can have a snap fitment with the collet insert, can have outer threads that mate with the collet insert, can include an alignment feature or structure that engages with a complementary structure in the collet insert, or can have a curved or channeled top surface that is alignable with the insert channel, and the like.

As described in more detail below, the pressure ring 190 is generally uploaded into the expandable collet pocket 164 after the collet insert 150 has been downloaded into its shipping state position, with the opposed lateral ridges 158 of the collet insert 150 engaged within the upper grooves 120 of the receiver 100. It is nevertheless foreseen that the pressure ring may be uploaded into the collet pocket prior to pre-assembly, and then downloaded together with the collet insert into the shipping state position.

With particular reference to FIGS. 15-18, the closure 50 comprises a generally cylindrical closure body having a top surface 52, a bottom surface 56, and an outer continuous guide and advancement structure 60 formed into the outer side surface 54 of the closure body that operably joins with the guide and advancement structure 116 formed into the interior face 110 of the receiver arms 104. In one aspect the guide and advancement structures 60, 116 can be helically wound flanges with splay-resisting or splay-controlling flange profiles for operably guiding under rotation and advancing the closure structure 50 downward between the arms 104 and having such a nature as to resist or control the splaying of the arms 104 when the closure structure 50 is advanced into the receiver channel 106. In other aspects the guide and advancement structures 60, 116 may take on a variety of alternative forms, including but not limited to a buttress thread, a square thread, a reverse angle thread, or other thread like or non-thread like helically wound advancement structure.

As shown in the drawings, in one aspect the bottom surface 56 of the closure can include a downwardly-projecting central projection 58 for engaging and securing the elongate rod, and for controlling the closure torque to thrust ratio. In other embodiments the bottom surface can include an annular projection, a point ring (i.e. an annular ring surrounding a central point or projection), a recessed surface surrounded by a low outer ridge, and the like. In yet other embodiments the bottom surface 56 can be substantially planar across the extent thereof.

The top surface 52 of the closure 50 can further include a driving tool engagement structure, such as internal drive socket 66, which extends downward or inward into the body of the closure 50. The internal drive socket 66 can be used for closure installation or removal. Similar to the internal drive socket formed into the shank head, the internal socket 66 of the illustrated closure 50 is an aperture formed in the top surface 52, and in one aspect can be a multi-lobular or star-shaped aperture, such as those sold under the trademark TORX, or the like, having internal faces 68 designed to receiver to a multi-lobular or star-shaped tool for rotating and driving the closure 50. It is foreseen that such an internal tool engagement structure 66 may take a variety of tool-engaging forms and may include one or more apertures of various shapes, such as a pair of spaced apart apertures or a hex shape designed to receive a hex tool (not shown) of an Allen wrench type. The seat or base surface 67 of the drive feature 66 is disposed perpendicular to a closure axis, with the drive feature 66 otherwise being coaxial with the axis.

In another aspect of the present disclosure, a break-off extension (not shown) can be attached the upper end or top surface of the closure, and extend upwardly away therefrom to provide an external tool engagement structure that can be used for rotatably advancing the closure downward between the arms 104 of the receiver 100. In one aspect the break-off extension can be designed to allow the extension to break from the closure at a preselected torque, for example, 60 to 140 inch pounds. It is further foreseen that closures having other shapes, configurations, thread forms or non-threaded engagement alternatives, and the like, that are different from those shown in the drawings while providing for similar interaction and functionality of the various components of the pivotal bone anchor assembly, are also possible and considered to fall within the scope of the present disclosure.

With reference to FIG. 19, the receiver 100, the collet insert 150, and the pressure ring 190 form the components of a receiver sub-assembly 14, and are generally pre-assembled together at a factory setting that includes tooling for holding, alignment and manipulation of the component pieces. In some circumstances, the shank is also assembled with the receiver sub-assembly 14 at the factory. In other instances, it is desirable to first implant the shank, followed by addition of the pre-assembled receiver sub-assembly at the insertion point (see, e.g., FIGS. 29-48). In this way, the surgeon may advantageously and more easily implant and manipulate a number of shanks along the patient's spine, distract or compress the vertebrae with the shanks, and work around the shank upper portions or shank heads without the cooperating receivers being in the way. In other instances, it is desirable for the surgical staff to pre-assemble a shank of a desired size and/or variety (e.g., cannulated shank body, different thread patterns on the shank body, and/or hydroxyapatite on the shank body), with the receiver sub-assembly prior to implantation of the shank into a patient's vertebra. Allowing the surgeon to choose the appropriately sized, type, or treated shank advantageously reduces inventory requirements, thus reducing overall cost.

Figure 24:
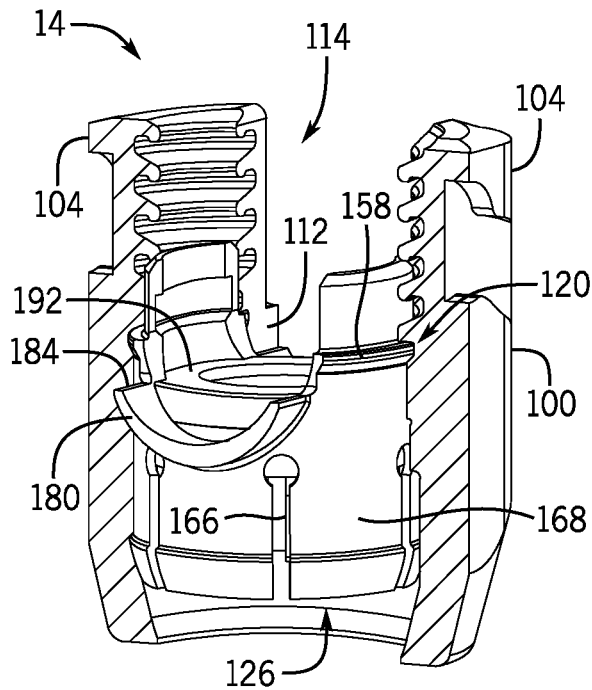
FIG. 24 is a partially cut-away perspective view of the receiver sub-assembly, with the collet insert and internal pressure ring pre-assembled into their shipping state positions within the receiver.
Figure 25:
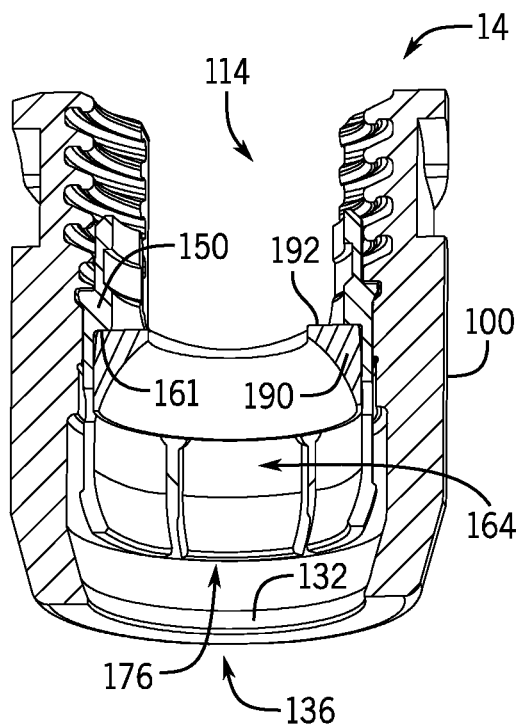
FIG. 25 is a sectioned perspective view of the receiver sub-assembly of FIG. 24.
Figure 26:
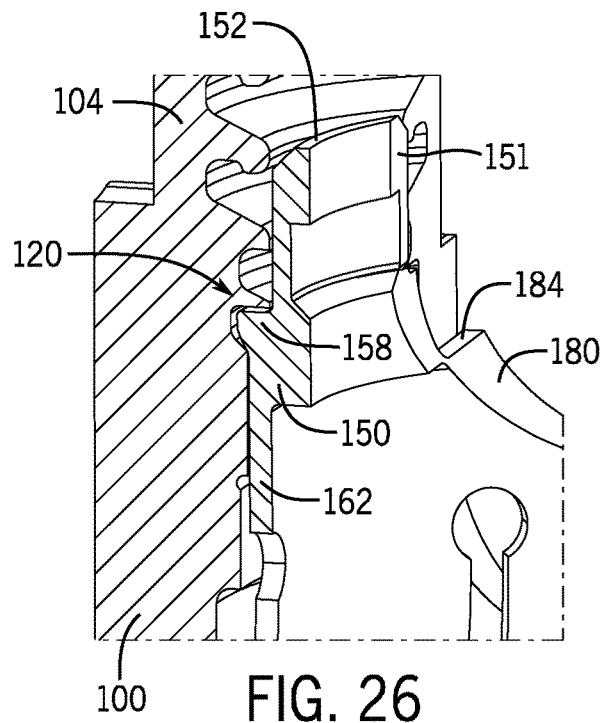
FIG. 26 is a close-up sectioned perspective view of the upper end of the collet insert in the pre-assembled configuration of FIG. 21.

The pre-assembly of the receiver 100, the collet insert 150, and the pressure ring 190 components of FIG. 19 into a receiver sub-assembly 14 is shown in FIGS. 20-28. With particular reference to FIGS. 20-21 and 26, first the opposed radial extensions 180 of the collet insert 150 are aligned with the rod channel 106 of the receiver, and then the collet insert 150 is dropped or driven downward into the central bore 114 of the receiver 100 (FIG. 20) until the opposed lateral ridges 158 or projections become engaged within the receiver upper shipping state grooves 120 (FIGS. 21, 26). In one aspect tooling (not shown) may be used to pinch inward the insert upright arms 154 as the collet insert 150 is dropped downwardly into position, so as to allow the collet insert lateral ridges 158 to pass downward through the guide and advancement structure 116 of the receiver 100 without significant interference between the parts. Alternatively, tooling (not shown) may be used to press open the receiver arms 104 and expand the receiver channel 106 as the collet insert 150 is dropped downwardly into position, also to allow the insert lateral ridges to pass downward through the receiver guide and advancement structure.

With continued reference to FIG. 21, during the downloading of the collet insert 150 to the shipping state position, the insert opposed radial extensions 180 can become slidably engaged by the upper opposing planar surfaces 112 of the receiver upright arms 104 to prevent the collet insert from rotating within the receiver axial bore 114. In addition, with the exterior projecting ridges 158 becoming engaged within the receiver upper shipping state grooves 120, the distal tip sections 170 of the resilient collet fingers 168 are suspended and centralized within the upper expansion chamber portion 128 of the receiver cavity 126.

Figure 22:
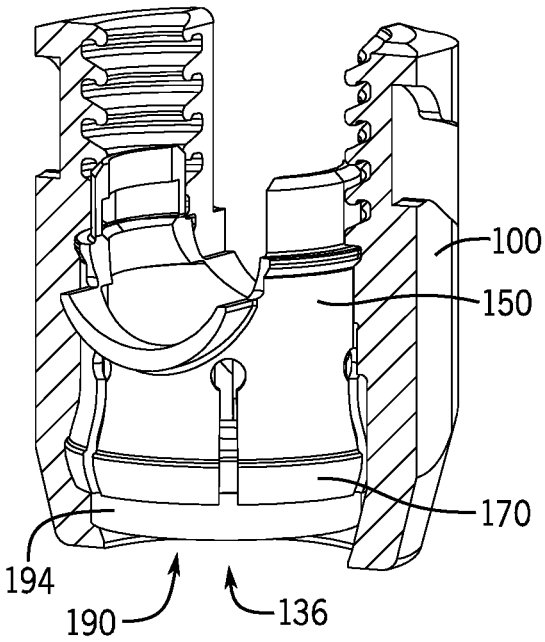
FIG. 22 is a partially cut-away perspective view of the pre-assembled receiver and collet insert of FIG. 21, with the internal pressure ring being installed therein.
Figure 23:
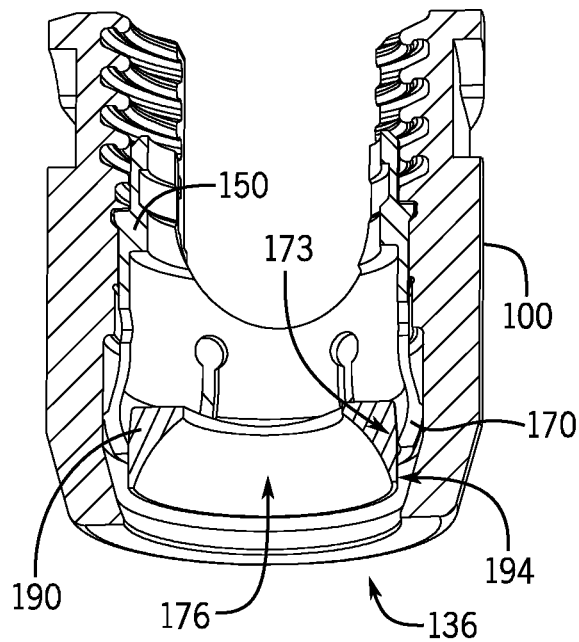
FIG. 23 is a sectioned perspective view of the receiver, collet insert, and internal pressure ring of FIG. 22.

With reference to FIGS. 22-23, the pressure ring 190 can now be uploaded through the receiver bottom opening 136 and into the collet insert distal pocket opening 176, causing the collet fingers 168 to flex outwardly and the distal pocket opening 176 to expand within the expansion chamber 128 while the innermost edges 173 of the distal tip sections 170 slide against the cylindrical outer surface 194 of the pressure ring 190.

With reference to FIGS. 24-25, the pressure ring 190 can continue upward through the collet pocket 164 until it reaches the shipping state configuration, in which the annular top surface 192 of the pressure ring 190 abuts the discontinuous downwardly-facing stop surface 161 of the collet insert 150. In this position the top surface 192 of the pressure ring 190 can also be substantially flush with the planar top edge surfaces 184 of the radial extensions 180. In one aspect the enclosed pressure ring 150 can be pressed into a slight interference engagement with its position within the upper portion of the collet pocket 164, in a location that is at least partially above the longitudinal slots 166 and/or relief apertures 167 that define the resilient collet fingers 168. With the top surface 192 of the pressure ring abutting the downwardly-facing stop surface 161, the pre-assembly of the receiver sub-assembly 14 is complete.

Figure 27:
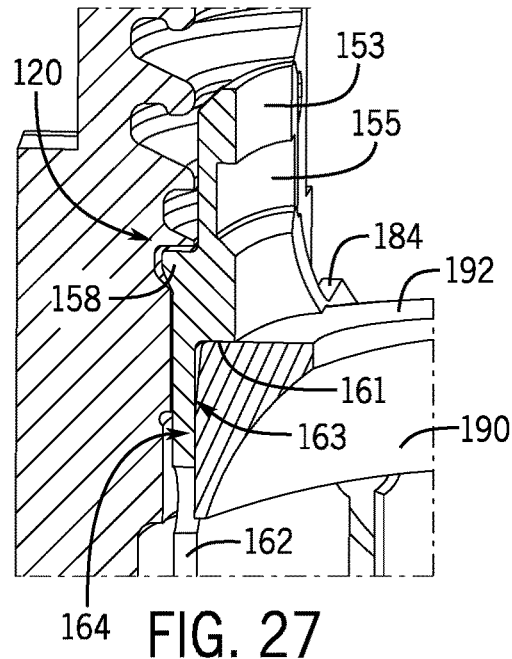
FIG. 27 is a close-up sectioned perspective view of the upper end of the collet insert and internal pressure ring in the pre-assembled configuration of FIGS. 24-25.

As shown in FIGS. 24-25 and 27, the receiver sub-assembly 14 is in a shipping state configuration in which the collet insert 150 is held in a vertical position within the receiver central axial bore 114 and inhibited from vertical movement due to the overlapped (or overlapping) engagement of the opposed lateral ridges 158 being received within the upper shipping state grooves 120. Furthermore, the upper shipping state grooves 120 are sized and shaped to prevent any upward movement of the collet insert 150 relative to the receiver 100, while allowing for downward movement or deployment of the collet insert 150 only with considerable direct force that may be provided by the appropriate tooling. As shown in FIG. 24, the collet insert is also held or 'clocked' in angular position by the opposed radial extensions 180 that are positioned between the upper opposing planar surfaces 112 of the receiver upright arms 104. As noted above, the pressure insert 190 may also be held or secured within the upper continuous cylindrical portion of the collet pocket 164 with a slight interference engagement, or some other type of engagement, between the cylindrical outer surface 194 of the pressure ring 190 and the inner surface 163 of the tubular sidewall 162. In one aspect the shipping state configuration shown in FIGS. 24-25 and 27 may also be known as the collet insert/pressure ring pre-deployment configuration.

Figure 28:
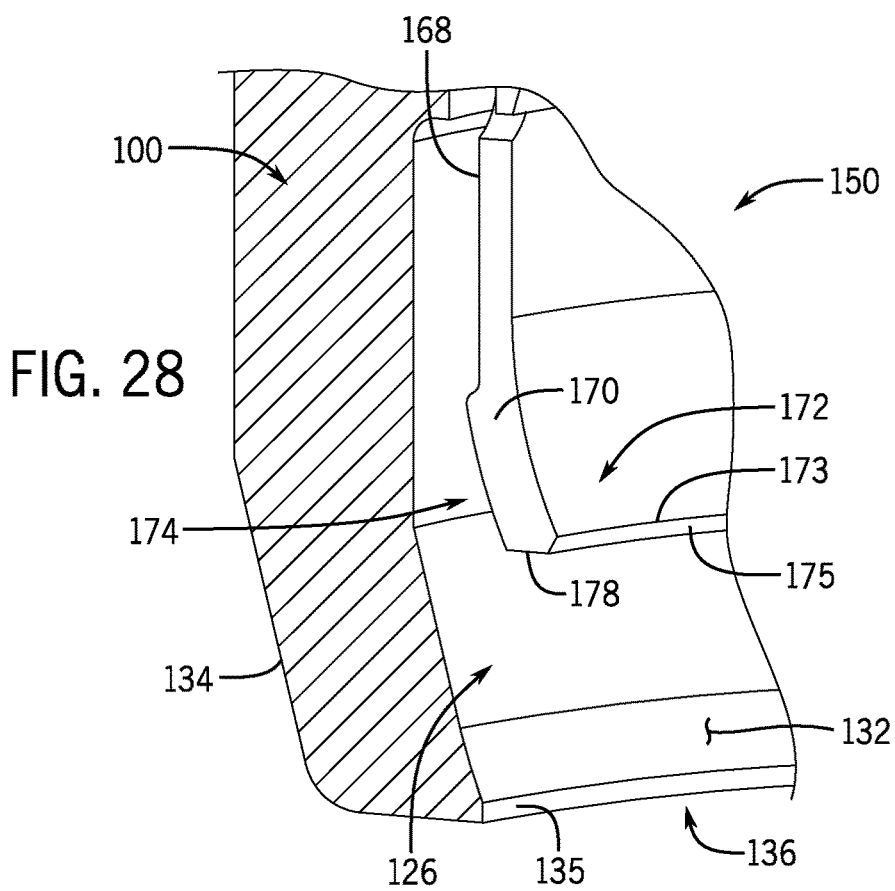
FIG. 28 is a close-up sectioned perspective view of the lower end of the collet insert in the pre-assembled configuration of FIGS. 21-25.

Furthermore, and with additional reference to FIG. 28, the distal tip sections 170 of the resilient collet fingers 168, acting as a retainer, will be suspended and centralized within the upper expansion chamber portion 128 of the receiver cavity 126 and spaced above the receiver bottom opening 136, in preparation for receiving the spherical head of the bone anchor. The outer partial spherical surfaces 174 of the distal tip sections 170 are also positioned vertically above the partial spherical interior seating surface 132 that is located just above the receiver bottom opening 136. As discussed below, the inner diameter of the partial spherical interior seating surface 132 can be equal to or greater than the outer diameter of the outer partial spherical surfaces 174 of the distal tip sections 170, so that the distal tip sections (and resilient collet fingers 168) can be maintained in a neutral position or in a slightly expanded position when the collet insert 150 is in a lower "capture/locking state" position.

Figure 29:
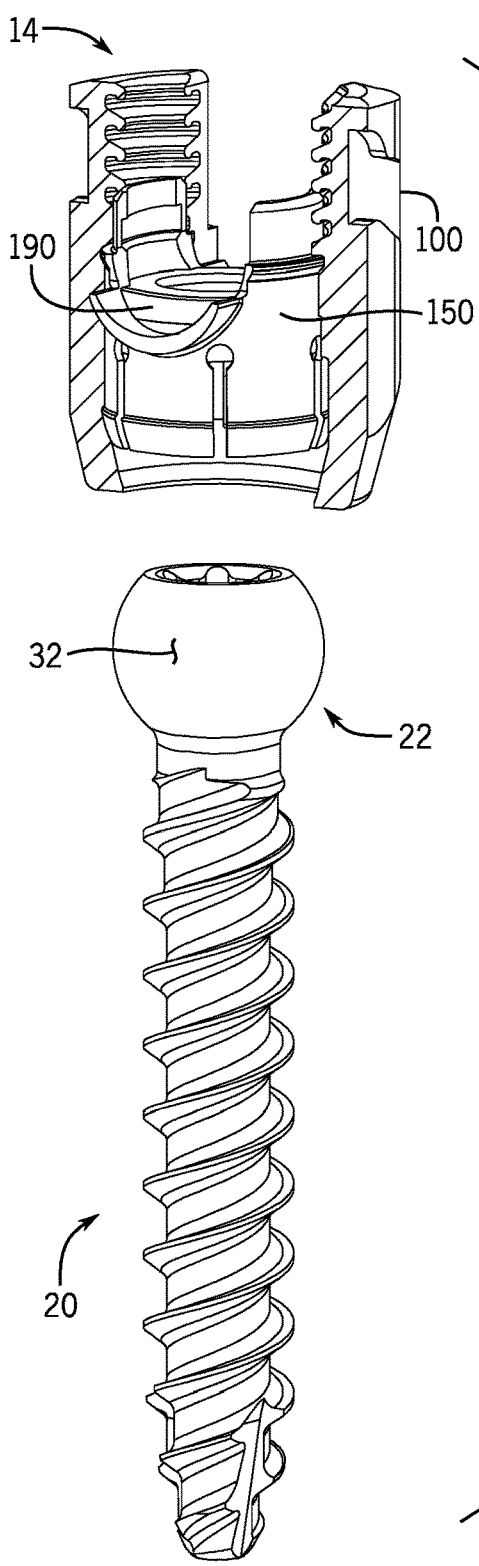
FIG. 29 is a partially cut-away perspective view of the receiver sub-assembly positioned above the shank head of a bone anchor.

Illustrated in FIGS. 29-43 is the assembly or coupling of the pre-assembled receiver sub-assembly 14 of the pivotal bone anchor assembly 10 of the present disclosure to the head 22 of a shank or bone anchor 20. As shown in FIG. 29, the receiver sub-assembly 14 is first positioned above the shank head 22 with the receiver bottom opening 136 generally aligned with the spherical outer surface 32 of the shank head 22.

Figure 30:
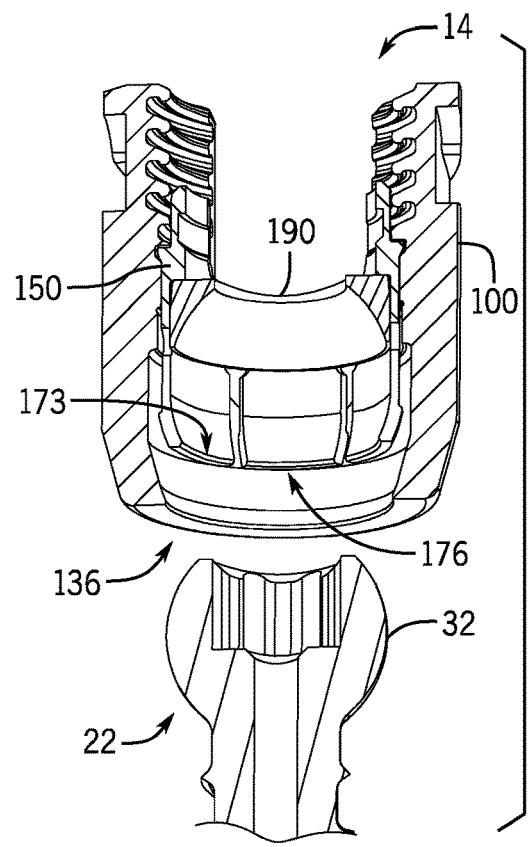
FIG. 30 is a sectioned perspective view of the receiver sub-assembly and bone anchor of FIG. 29.
Figure 31:
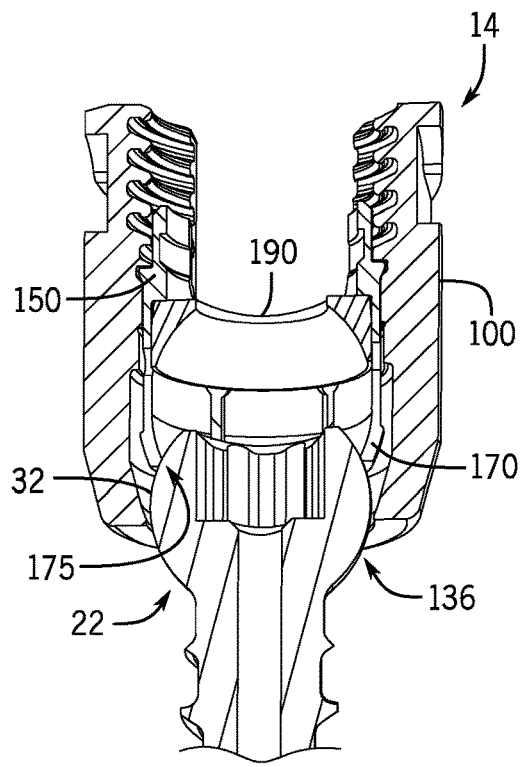
FIG. 31 is a sectioned perspective view of the receiver sub-assembly moving downward until the shank head enters the bottom opening and the upper portion of the shank head spherical outer surface contacts the innermost edges of the distal tip sections.

With reference to FIGS. 30-31, the receiver sub-assembly 14 is then dropped downward (or the shank 20 is moved upward, depending on the frame of reference of the reader) until the shank head 22 enters the bottom opening 136 and the upper portion of the spherical outer surface 32 contacts the innermost edges 173 of the distal tip sections 170. As previously described, the innermost edges 173 or chamfered surface 175 of the distal tip sections 170 can be rounded or chamfered to facilitate slidable engagement with the spherical outer surface 32.

With reference to FIGS. 32-33, the receiver sub-assembly 14 continues to move downward (or the shank 20 moves upward) as the upper portion of the shank head spherical outer surface 22 bears against the innermost edges 173 of the distal tip sections 170, causing the collet fingers 168 to flex outward and the distal pocket opening 176 to expand within the upper expansion chamber portion 128 of the receiver cavity 126, until the distal pocket opening reaches maximum expansion.

With reference to FIGS. 34-35, the receiver sub-assembly 14 continues to move downward (or the shank 20 moves upward) until the shank head 22 reaches max push-through, in which the upper portion of the spherical outer surface 32 abuts the lower concave surface 196 of the pressure ring 190 and a center portion of the spherical outer surface 32 bears against the inner surfaces 163 of the substantially cylindrical sidewalls 163 that define the collet pocket 164.

Figure 36:
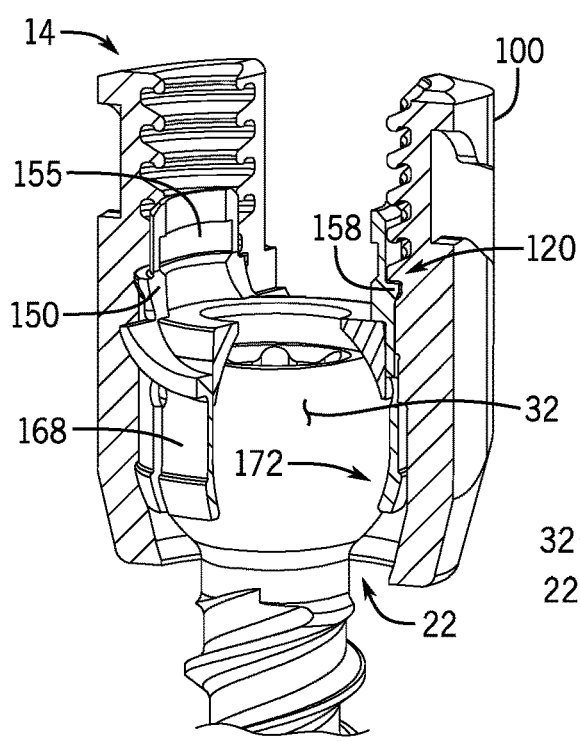
FIG. 36 is a partially cut-away perspective view of the receiver sub-assembly moving back upward until the lower portion of the shank head spherical outer surface contacts the plurality of inner partial spherical surfaces of the distal tip sections.
Figure 37:
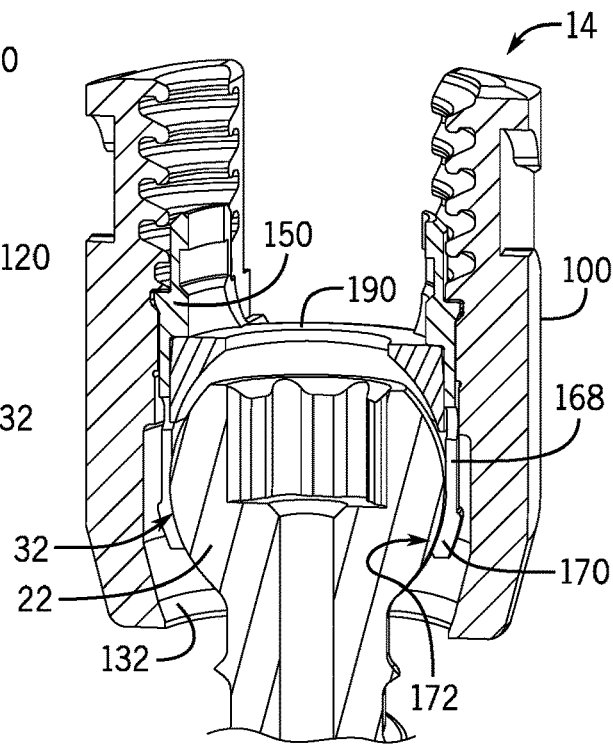
FIG. 37 is a sectioned perspective view of the receiver sub-assembly and shank head of FIG. 36.

With reference to FIGS. 36-37, the receiver sub-assembly 14 is moved or pulled back upward (or the shank 20 downward) until the lower portion of the spherical outer surface 32 of the shank head 22 contacts the plurality of inner partial spherical surfaces 172 of the distal tip sections 170. In one aspect the collet fingers 168 can be slightly expanded compared to their nominal state so as to provide a light friction fit or head drag between the shank 20 and receiver 100, prior to the collet insert 150 being downwardly deployed within the receiver 100. The shank head 22 is now lightly captured within the pocket 164 of the collet insert 150, but could still be removed from the receiver sub-assembly 14 if the shank 20 were to be pulled forcefully downward, causing the resilient collet fingers 166 to expand and release the shank head 22 from the collet pocket 164.

Figure 38:
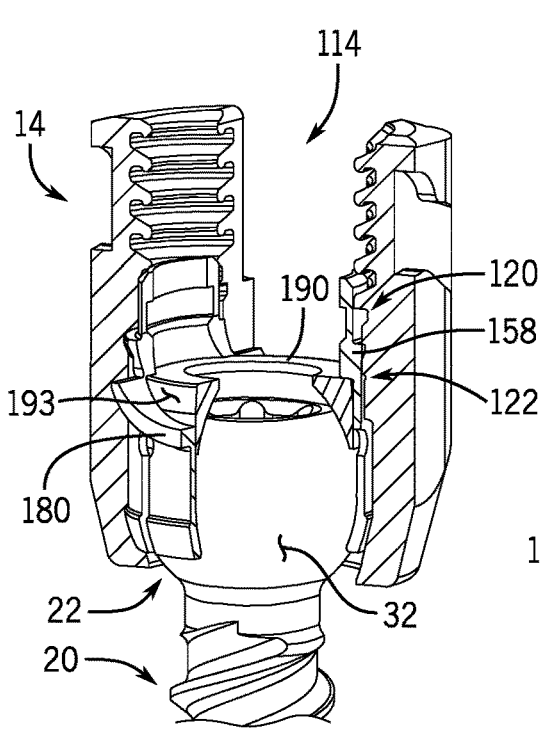
FIG. 38 is a partially cut-away perspective view of the receiver sub-assembly and coupled shank head, with the collet insert pushed downwardly into a partially deployed position.
Figure 39:
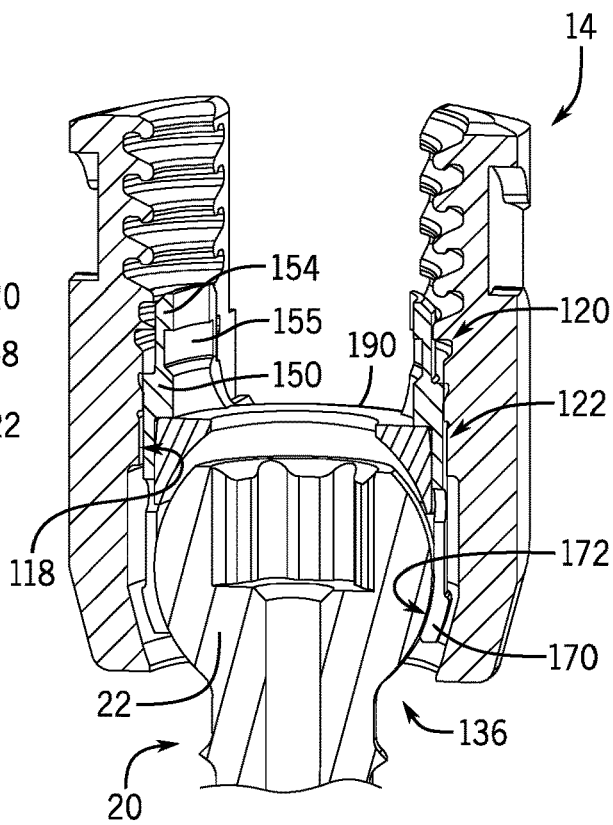
FIG. 39 is a sectioned perspective view of the receiver sub-assembly and shank head of FIG. 38.

With reference to FIGS. 38-39, the collet insert 150, together with the enclosed pressure ring 190 and lightly captured shank head 22, can then be pushed downward with deployment tooling (not shown) that engages the planar top edge surfaces 184 of the opposed radial extensions 180. The pushing or deployment can include the application of considerable force to the top of the collet insert tool engagement surfaces 184, so as to push the opposed lateral ridges 158 of the collet insert 150 downward out of the upper shipping state grooves 20 of the receiver 100 and onto the discontinuous cylindrical surface 118 of the central bore 114, where the lateral ridges 158 encounter an interference fit that resists the downward motion. The force required to overcome this interference fit can be about 200 pounds-force or greater, and is generally provided by the deployment tooling. This action can temporarily cause the upwardly-projecting arms 154 of the collet insert 150 to flex inwardly, temporarily reducing the gap at the top of the collet insert channel 156. With the collet insert 150 in this position, the elongate rod 70 would not necessarily fit within the collet insert channel 156. As described above, the outer surface of the pressure ring 190 can have an upper tapered relief portion 193 that is tapered inwardly to provide room for this inward flexing of the upright arms 154 of the collet insert 150, so as to allow the lateral ridges 158 to become disengaged from the upper shipping state grooves 120 of the receiver 100. In an alternative embodiment, the deployment tooling (not shown) can also or preferably engage the upper tool engagement structure (e.g. recess 155) formed into the discontinuous upper cylindrical surface 153 of the integral upright arms 154 extending above the collet portion of the collet insert 150.

Figures 40, 41:
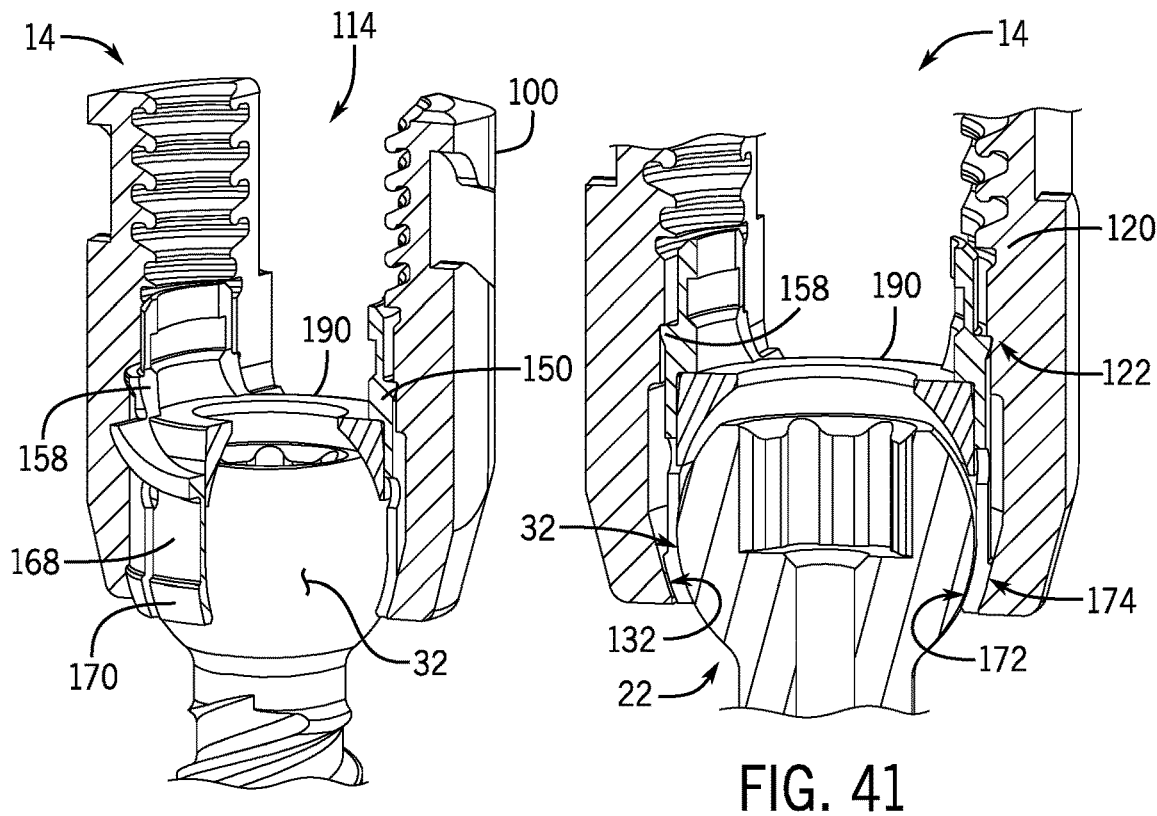
FIG. 40 is a partially cut-away perspective view of the receiver sub-assembly and coupled shank head, with the collet insert pushed further downwardly into a fully deployed position.
FIG. 41 is a sectioned perspective view of the receiver sub-assembly and shank head of FIG. 40.

With reference to FIGS. 40-41, the collet insert 150 with the enclosed pressure ring 190 can continue to be pushed or deployed downward with the deployment tooling until (a) the opposed lateral ridges 158 snap into the lower "capture/locking state" grooves 122 of the receiver central bore 114, (b) the partial spherical interior seating surface 132 engages the plurality of outer partial spherical surfaces 174 of the distal tip sections 170 to restrain further outward movement or flexing of the distal tip sections 170, and (c) the plurality of inner partial spherical surfaces 172 of the distal tip sections 170 more forcefully engage the lower portion of the spherical outer surface 32 of the shank head 22 to prevent the shank head 22 from exiting downward through the receiver bottom opening 136. The shank head 22 is now fully captured within the receiver sub-assembly 114 with the collet insert in the capture/locking state position.

During the downward deployment of the collet insert 150 to the capture/locking state position shown in FIGS. 40-41, the outer partial spherical surfaces 174 of the distal tip sections 170 may descend vertically through the receiver internal cavity 126 until engaging with and seating upon the partial spherical interior seating surface 132. As noted above, the inner diameter of the partial spherical interior seating surface 132 can be equal to or slightly greater than the outer diameter of the outer partial spherical surfaces 174 of the distal tip sections, so that distal tip sections 170 (and the resilient collet fingers 168) can be maintained in a neutral position or in a slightly expanded position when the collet insert 150 is in the lower capture/locking state position.

In addition, it will be appreciated that the partial spherical interior seating surface 132 of the receiver cavity 126, the outer partial spherical surfaces 174 of the distal tip sections 170, the inner partial spherical surfaces 172 of the distal tip sections 170, and the spherical outer surface 32 of the shank head 20 can, in one aspect, define four substantially-concentric spherical surfaces (i.e. when their geometric centers are located at substantially the same location along the receiver longitudinal axis). Alternatively, it is also contemplated that the geometric centers of one or more of the spherical surfaces (e.g. the receiver partial spherical seating surface) can be vertically offset from the other geometric centers to facilitate the separation of the surfaces during remobilization, as described in more detail below. It is further foreseen that other diameters and/or configurations for the partial spherical surfaces and their geometric centers are also possible.

Figures 42, 43:
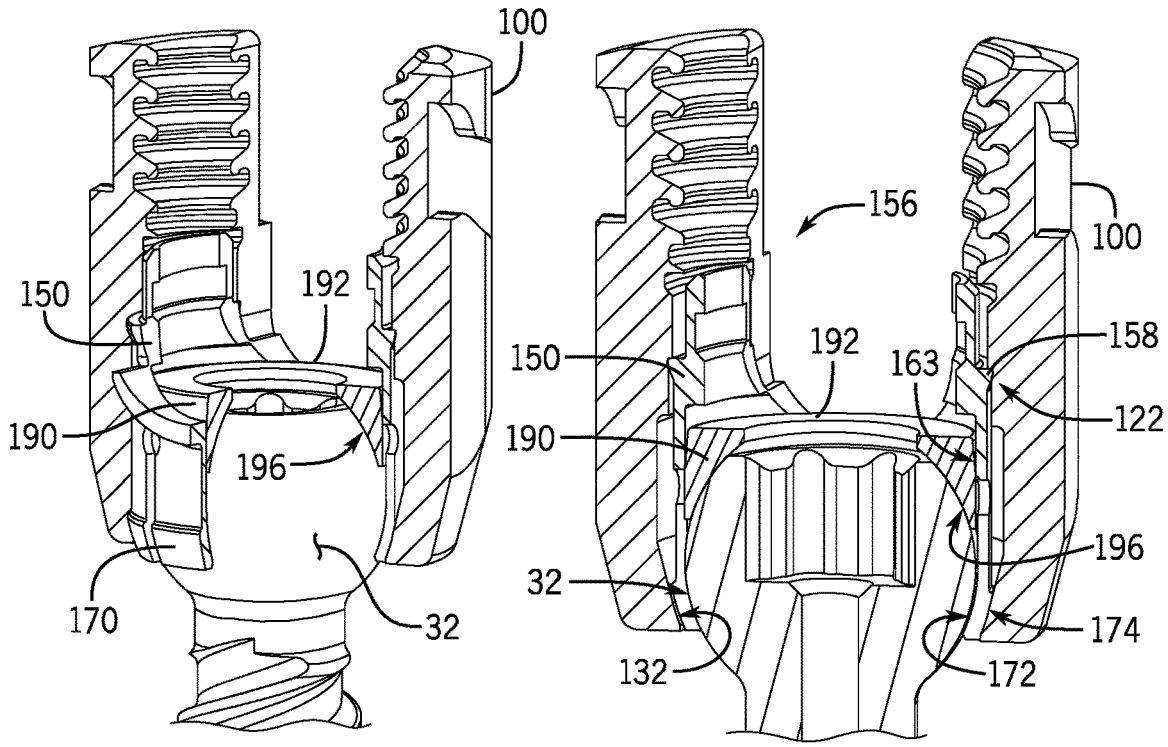
FIG. 42 is a partially cut-away perspective view of the receiver sub-assembly and coupled shank head, with the pressure ring pushed downwardly from its position in the upper portion of the collet pocket until the concave partial spherical bottom surface of the pressure ring engages the upper portion of the shank head spherical surface.
FIG. 43 is a sectioned perspective view of the receiver sub-assembly and shank head of FIG. 42.
Figure 46:
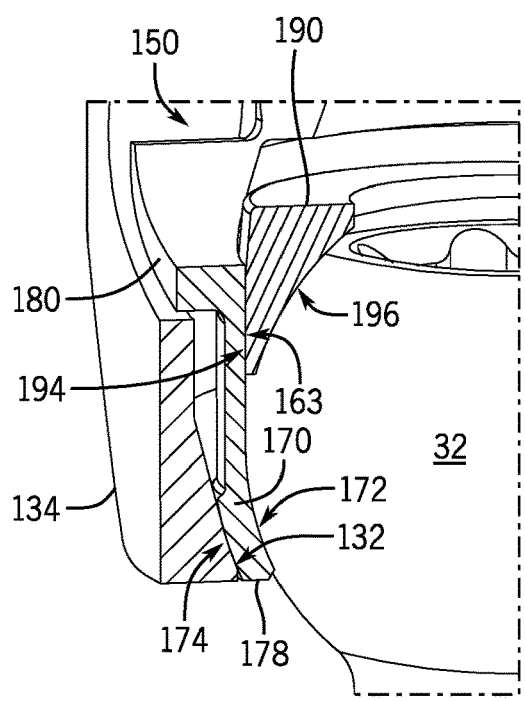
FIG. 46 is a close-up partially cut-away perspective view of the lower end of the collet insert, shank head, and pressure ring in the fully locked configuration of FIG. 44.

With reference to FIGS. 42-43 and 46, the enclosed pressure ring 190 can now be individually pushed or deployed downwardly from its position in the upper portion of the collet pocket 164 until the lower, downwardly-opening concave surface 196 of the pressure ring engages the upper portion of the spherical outer surface 32 of the shank head 22. A downwardly-directed force sufficient to overcome the slight interference engagement between the cylindrical outer surface 194 of the pressure ring 190 and the tubular sidewall inner surfaces 163 of the collet pocket 64 may be required. The downwardly-directed force can be directly applied with a tool or by the elongate rod positioned in the receiver and insert channels 106, 156 prior to deployment. In one aspect the capture/locking state configuration shown in 42-43 and 46 may also be known as the collet insert/pressure ring post-deployment configuration.

Optionally, once engaged with the shank head 22, the pressure ring 190 may be further compressed downward onto the shank head 22 by a deployment tool, so as to apply an initial loading onto the spherical outer surface 32 that is transferred downward to the partial spherical seating surface 132 of the receiver cavity 126. This initial compressive loading may be maintained by a frictional interference fit between the cylindrical outer surface 194 of the pressure ring 190 and the sidewall inner surfaces 163 of the collet pocket 164. In one aspect the compressive loading may also be sufficient to establish, or further assure, a non-floppy friction fit that holds the position of the receiver sub-assembly 14 relative to the shank head 22, while still allowing for movement of the receiver sub-assembly 14 relative to the bone anchor 20 with an applied force. For example, the friction fit can allow for rotation of the receiver 100 around the shank head 22, with an applied twisting force, so as to align the receiver channel 106 with the receiver channels of one or more adjacent bone anchor assemblies. The friction fit can also allow for angulation of the receiver 100 relative the shank head 22, with an applied moment force, also to align the receiver channel 106 with the receiver channels of an adjacent bone anchor assembly.

Illustrated in FIGS. 44-45 and 47-48 is the pivotal bone anchor assembly 10 as fully assembled and locked with the elongate rod 70 and closure 50. For instance, after a desired alignment of the receiver sub-assembly 14 to the bone anchor 20 has been achieved, the elongate rod 70 can be installed (i.e. reduced) into the collet insert channel 156 until the lowermost or underside surface 74 of the elongate rod 70 engages the top surface 192 of the pressure ring 150. The closure 50 can then be installed into the upper portion of the receiver axial bore 114, in which the continuous guide and advancement structure 60 of the closure body engages the discontinuous guide and advancement structure 116 formed into the interior face 110 of the receiver upright arms 104. The closure 50 can be threaded downwardly until the bottom surface 56 or the protrusion 58 of the closure 50 engages the top surface 72 of the elongate rod 70. Further rotation/torqueing of the closure 50 can then be used to drive the elongate rod 70 downward onto the pressure ring 190, which in turn drives the shank head 22 and the distal tip sections 170 of the collet insert 150 further downward into the partial spherical seating surface 132 to achieve a final locking of the bone anchor assembly 10, in which the receiver sub-assembly 14 can no longer move relative to the bone anchor 20.

In one aspect the elongate rod 70 does not push directly on the collet insert 150 after downloading into the collet insert channel 156, as the top surface 192 of the pressure ring 190 remains above the upper curved surfaces 182 of the opposed insert extensions 180 to establish a single load path from the elongate rod 70 down into the receiver body 100 via the pressure ring 190. Thus, the final locked state of the shank head 22 can be provided from above by frictional engagement between the downwardly-opening concave surface 196 of the pressure ring 190 and the upper portion of the spherical outer surface 32 of the shank head 22, and from below by frictional engagement between the plurality of inner partial spherical surfaces 172 of the distal tip sections 170 and the lower portion of the spherical outer surface 32.

In yet another aspect of the disclosure, a closure break-off extension (not shown) can be configured to shear away from the top surface or end 52 of the closure body at a pre-determined torque value, thereby ensuring that the pivotal bone anchor assembly 10 is fully locked at a consistent pre-determined torque value.

Furthermore, it will be appreciated by one of skill in the art that the interface between the receiver cavity partial spherical seating surface 132 and the plurality of outer partial spherical surfaces 174 of the distal tip sections 170 can determine the strength, or pull-out resistance, of the fully locked pivotal bone anchor assembly 10. For example, and with reference back to FIG. 46, the distal tip sections 170 of the collet insert 150 are generally configured to transfer load from the shank head 22 to the receiver base 134. Relative motion between the distal tip sections 170 and the receiver base 134 is limited by friction and interference between the outer surfaces 174 of the distal tip sections 170 and the partial spherical seating surface 132 of the receiver cavity 126. Assuming that relative motion between the distal tip sections 170 and the receiver base 134 is restricted or substantially prevented, pull-out resistance of the shank or bone anchor 20 is provided by a plurality of shear walls in the collet fingers 168/distal tip sections 170 that start at the major diameter of the shank head 22 and terminate at the bottom surface 178 of the distal tip sections 170.

Figure 49:
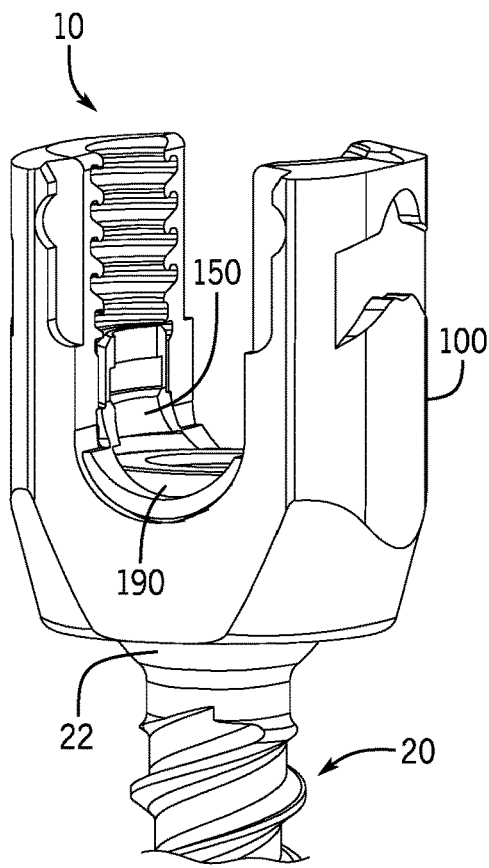
FIG. 49 is a perspective view of the receiver sub-assembly and shank head after removal of the closure and elongate rod and remobilization of the receiver sub-assembly.
Figure 50:
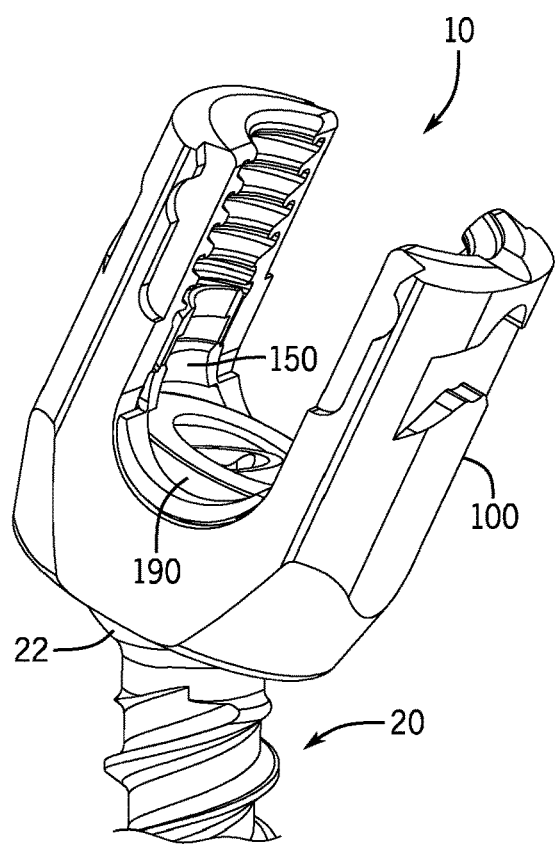
FIG. 50 is another perspective view of the receiver sub-assembly and shank head of FIG. 49, with the receiver sub-assembly being pivoted relative to the shank head.
Figure 51:
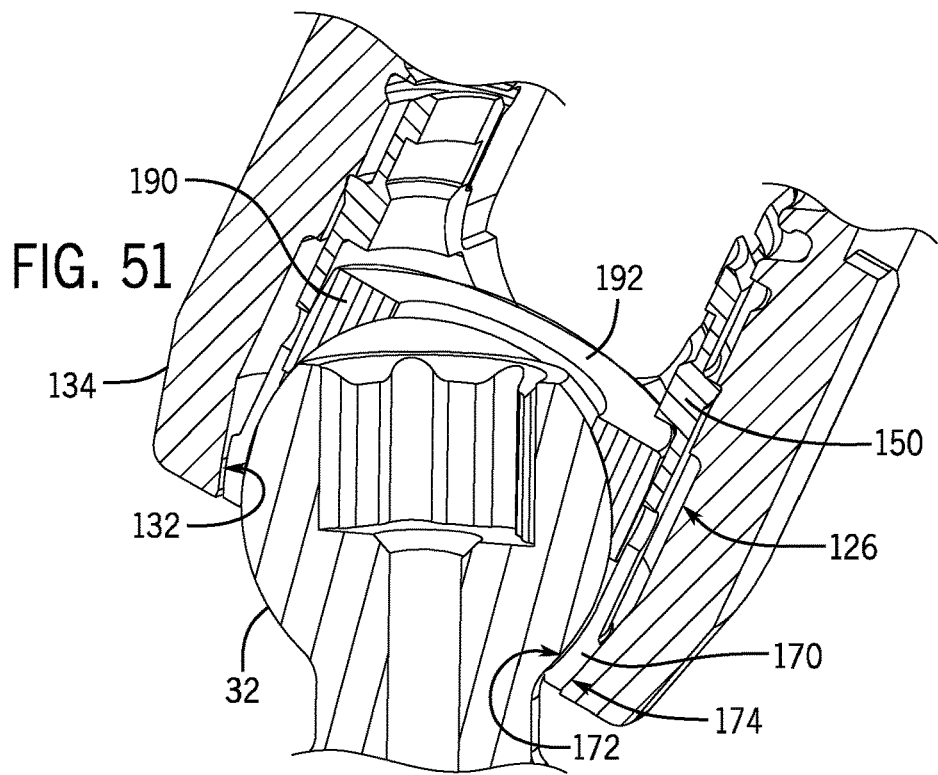
FIG. 51 is close-up sectioned perspective view of the receiver sub-assembly and shank head of FIG. 50.
Figure 52:
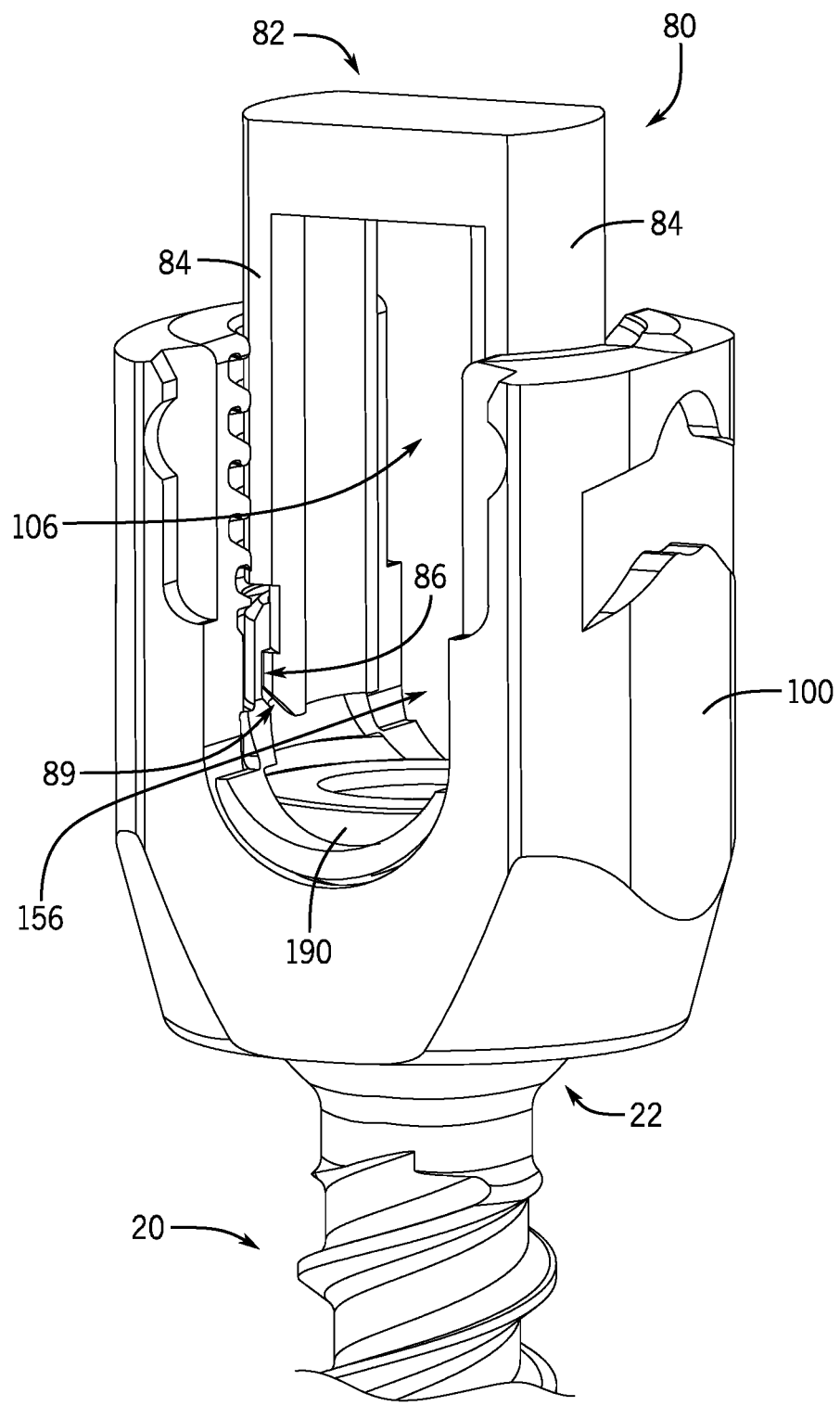
FIG. 52 is a perspective view of the receiver sub-assembly and shank head after insertion of a disassembly tool into engagement with the upper tool engagement recesses of the collet insert.

Among others, one useful aspect of the fully-assembled pivotal bone anchor assembly 10 disclosed above is that bone anchor assembly 10 can be re-mobilized relative to the head 22 of the bone anchor 20 simply by removing or loosening the closure. For example, and with reference to FIGS. 49-51, the closure and elongate can be removed so as to remobilize the pivotal bone anchor assembly 10 relative to the shank head 22. Although the bone anchor assembly 10 is shown in the drawings with the closure and elongate rod being completely removed, remobilization can be accomplished simply by loosening the closure while leaving both the closure and elongate rod in place. Loosening the closure removes the downward force applied to the pressure ring 190 through the elongate rod, thereby reducing the frictional engagement on the upper and lower portions of the spherical outer surface 32 of the shank head 22. With the reduction of the frictional engagement on the upper and lower portions of the spherical outer surface, the receiver sub-assembly 14 becomes free again to rotate relative to the shank head 22.

As previously described, the partial spherical profile of the receiver cavity seating surface 132 can be substantially concentric with each of the partial spherical profiles of the outer surfaces 174 and inner surfaces 172 of the distal tip sections 170, and with the spherical profile of the shank head 22. This design reduces the likelihood for inadvertently creating a permanently locked engagement between the distal tip sections 170 of the collet insert 150 and the receiver cavity seating surface 132 when fully locking the pivotal bone anchor assembly 10, as described and illustrated above. For example, using a partial spherical profile for the seating surface 132 of the receiver cavity 126, rather than a conical or tapered profile, better distributes the friction forces across the seating surface 132, better centers the collet fingers 168 around the circumference of the receiver cavity seating surface 132 to avoid cocking/misalignment of the collet insert 150 within the receiver cavity 126, avoids creating a concentrated line of contact that may cause localized deformation and bonding between the two surfaces 132, 174; and avoids a tapered locking engagement between the collet insert 150 and the receiver 100. As noted above, the geometric center of the partial spherical profile of the receiver cavity seating surface 132 can also be vertically offset or displaced slightly from the geometric centers of the other three spherical profiles. It is contemplated that this vertical displacement can operate to re-direct the normal force to twist the upper portions of the distal tip sections 170 toward or away from the partial spherical seating surface 132 of the receiver cavity 126.

Figure 53:
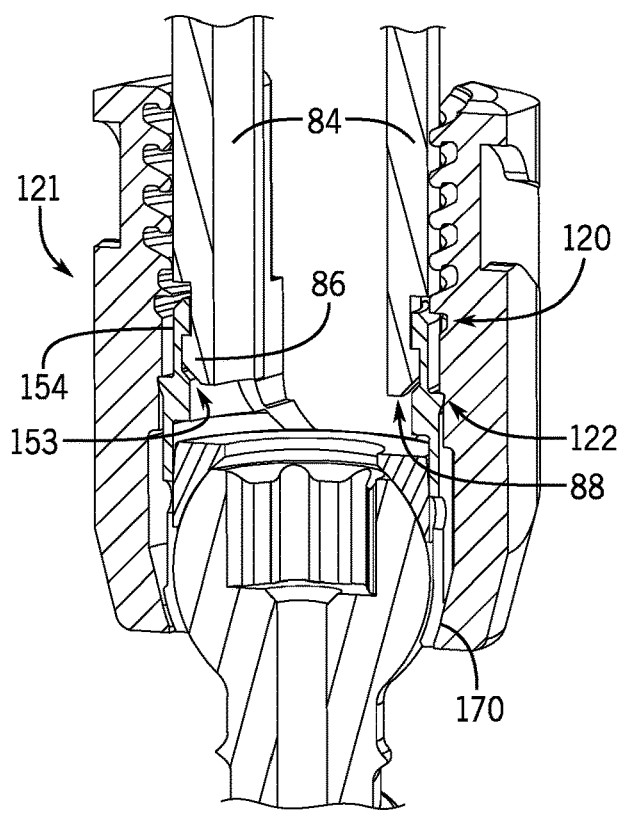
FIG. 53 is sectioned perspective view of the receiver sub-assembly, shank head, and disassembly tool of FIG. 52.
Figure 54:
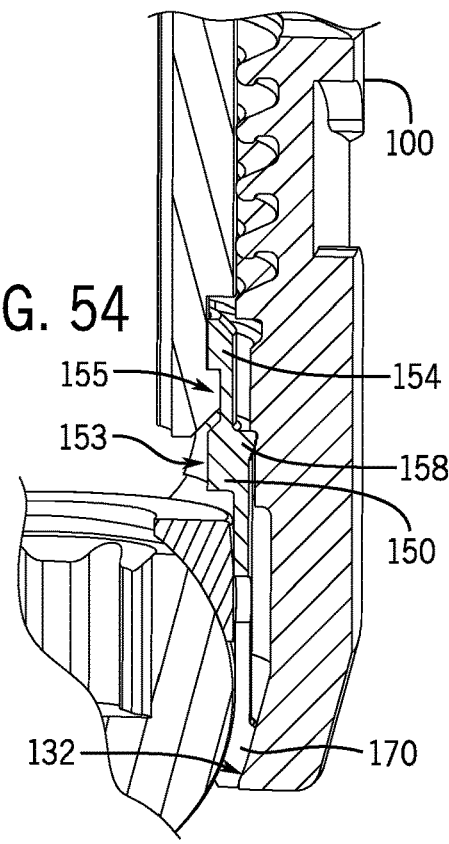
FIG. 54 is close-up sectioned perspective view of the receiver sub-assembly, shank head, and disassembly tool of FIG. 53.

Illustrated in FIGS. 52-59 is the disassembly and removal of the receiver sub-assembly 14 of the pivotal bone anchor assembly 10 from the head 22 of the shank or bone anchor 20. As shown first in FIG. 52, after the removal of the closure and the elongate rod from the receiver sub-assembly 14, a disassembly tool 80 can be downwardly introduced into the open channel 106 of the receiver 100 and engaged with the collet insert 150. The disassembly tool 80 includes a center portion 82 comprising two downwardly-extending prongs 84, with each prong having an outwardly-facing hook portion 86 that is sized and shaped to engage with the upper tool engagement structures or recesses 155 formed into the discontinuous upper cylindrical surface 153 of the insert arms 154 of the collet insert 150. The prongs 84 may be configured to flex inwardly toward each other, with the lower tip 88 of each prong 84 including a tapered surface 89 that first contacts the top edge of an insert upright arm 154 when introduced into the open channel 106 of the receiver 100. This initial contact can cause the prongs 84 to flex inwardly toward each other, after which the outwardly-facing hook portions 86 ride downwardly along the discontinuous cylindrical surfaces 153 of the insert arms 154 until they snap into the upper tool engagement recesses 155 (FIGS. 53-54). Alternatively, the prongs 84 of the disassembly tool 80 may be orientated to align with the open channel 106 of the receiver 100 and the open channel 156 of the collet insert 150 before being positioned downwardly within the insert channel 156, and then rotated about the receiver longitudinal axis until the hook portions 86 engage with the upper tool engagement recesses 153.

Figure 55:
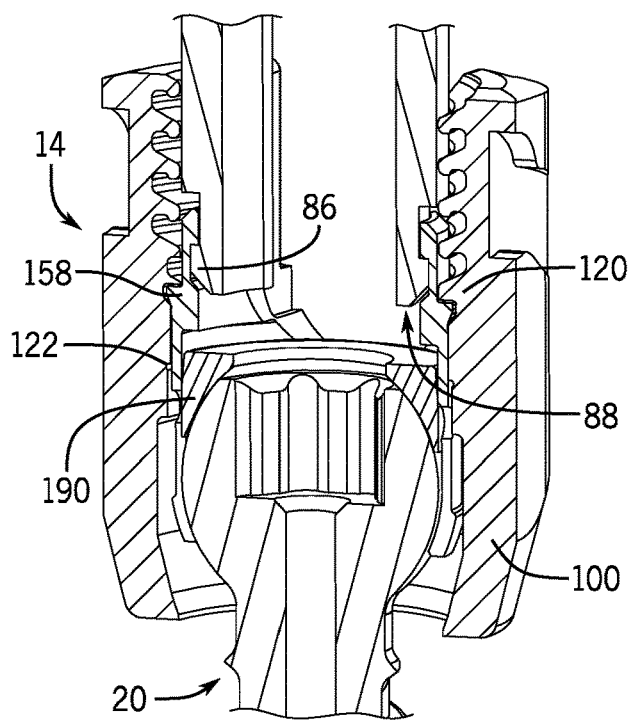
FIG. 55 is sectioned perspective view of the receiver sub-assembly, shank head, and disassembly tool after the withdrawal of the collet insert back up to the upper shipping state configuration.
Figure 56:
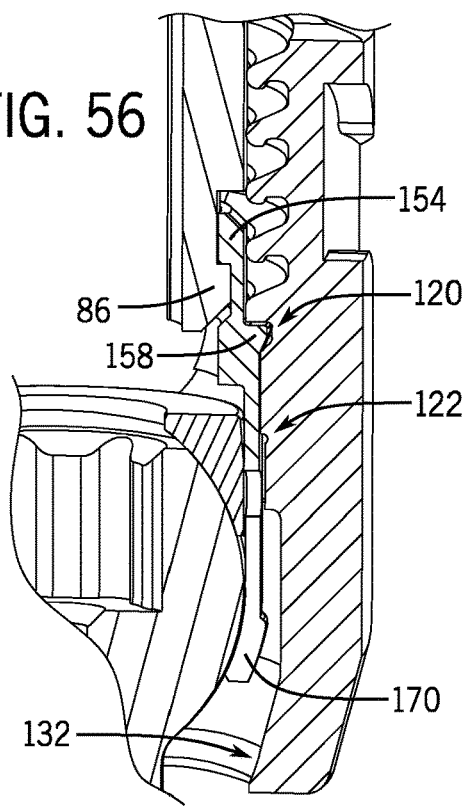
FIG. 56 is close-up sectioned perspective view of the receiver sub-assembly, shank head, and disassembly tool of FIG. 55.
Figure 72:
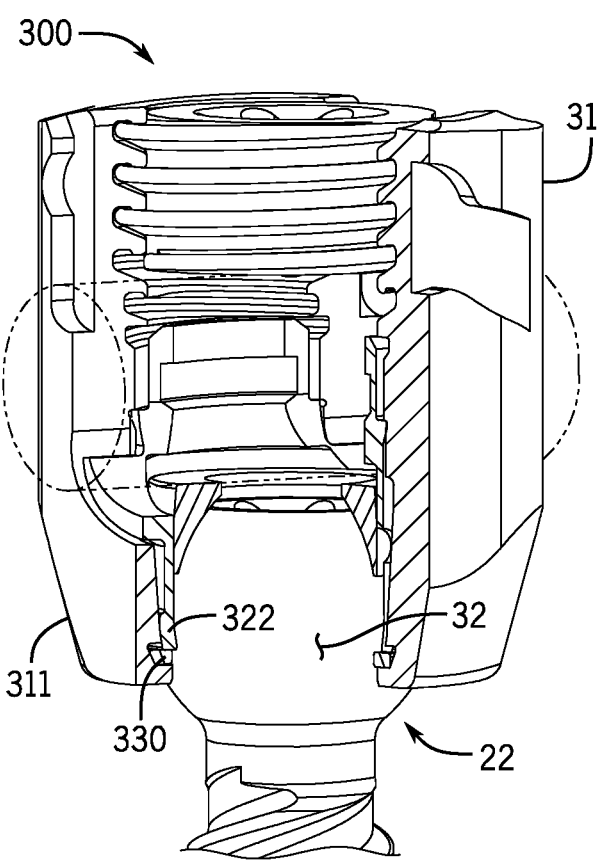
FIG. 72 is a partially cut-away perspective view of the receiver sub-assembly and shank head of FIG. 68, together with an elongate rod and closure, in the fully locked configuration.
Figure 73:
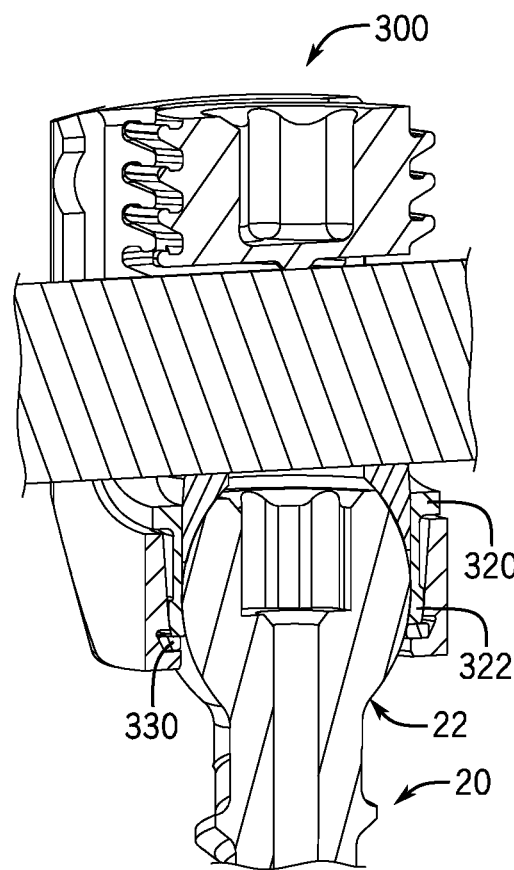
FIG. 73 is a sectioned perspective view of the receiver sub-assembly, shank head, elongate rod, and closure in the fully locked configuration of FIG. 72.
Figure 74:
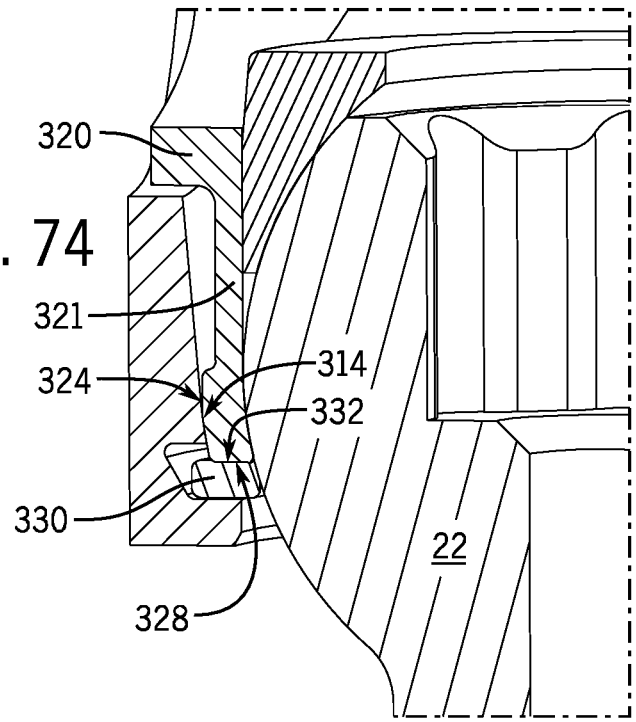
FIG. 74 is a cross-sectional side view of the receiver sub-assembly and shank head in the fully locked configuration of FIG. 72.
Figure 75:
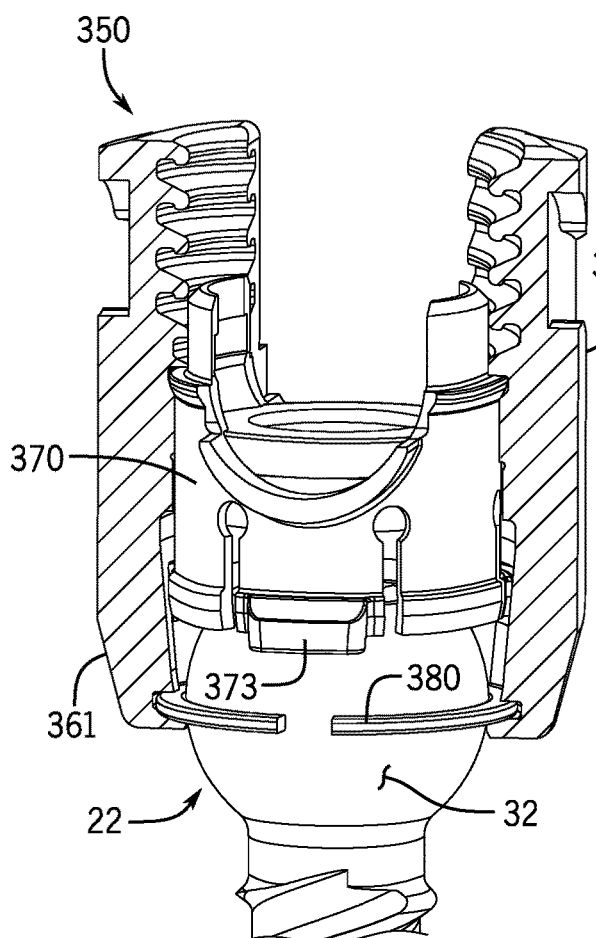
FIG. 75 is a partially cut-away perspective view of a receiver sub-assembly, including an expansion ring, during assembly with a shank head, in accordance with yet another representative embodiment of the present disclosure.
Figure 76:
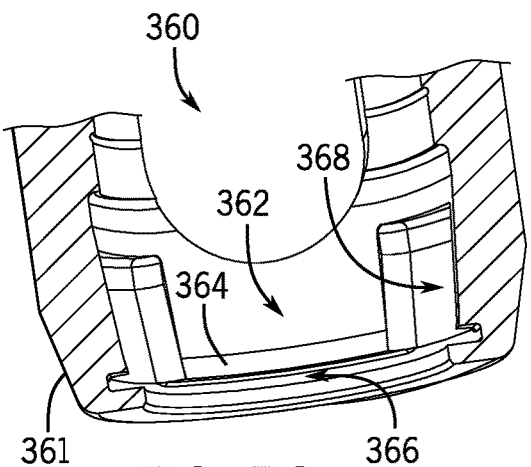
FIG. 76 is a cross-sectional perspective view of the receiver of FIG. 75.
Figure 77:
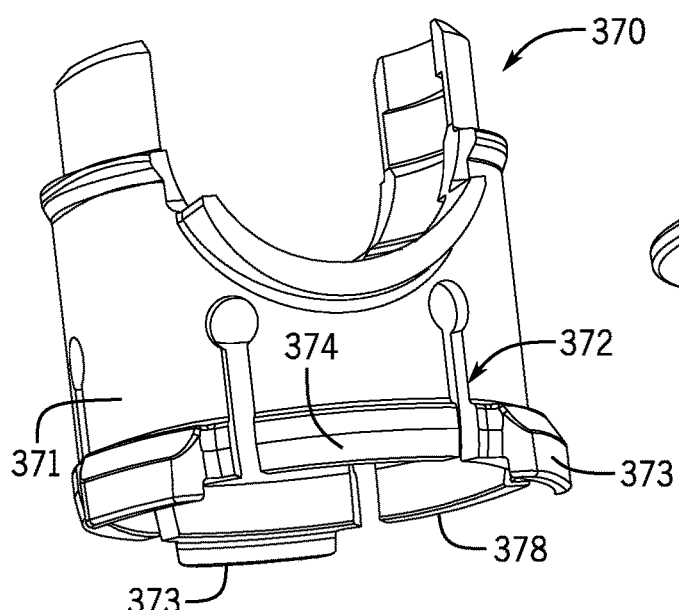
FIG. 77 is a perspective view of the collet insert of FIG. 75.
Figure 78:
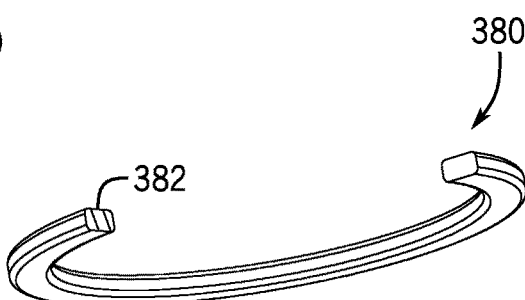
FIG. 78 is a perspective view of the expansion ring of FIG. 75.
Figure 79:
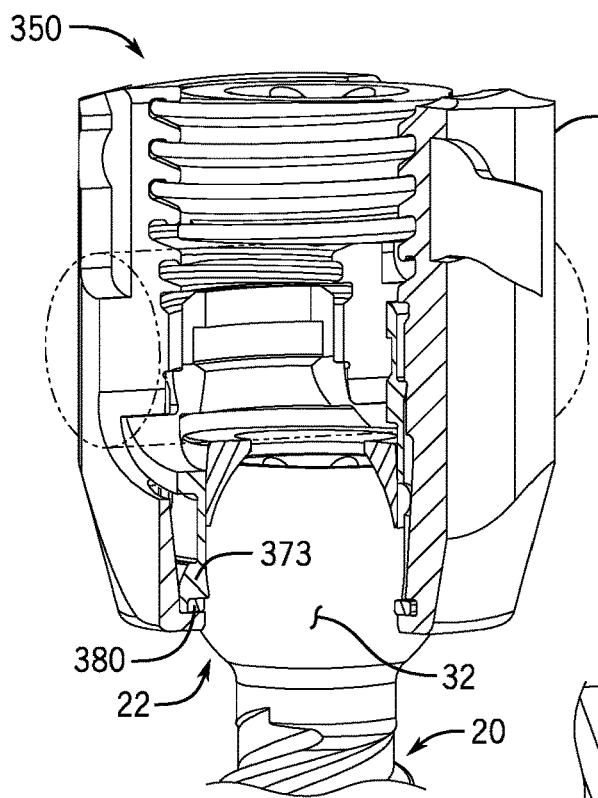
FIG. 79 is a partially cut-away perspective view of the receiver sub-assembly and shank head of FIG. 75, together with an elongate rod and closure, in the fully locked configuration.
Figure 80:
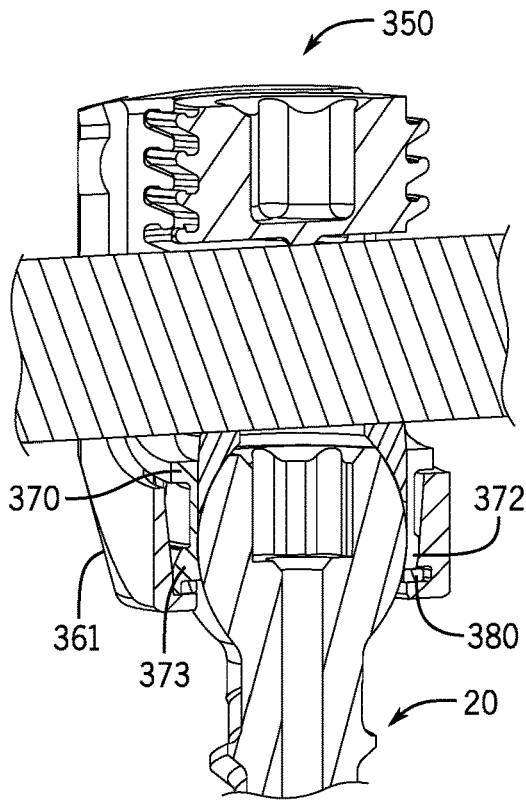
FIG. 80 is a sectioned perspective view of the receiver sub-assembly, shank head, elongate rod, and closure in the fully locked configuration of FIG. 79.
Figure 81:
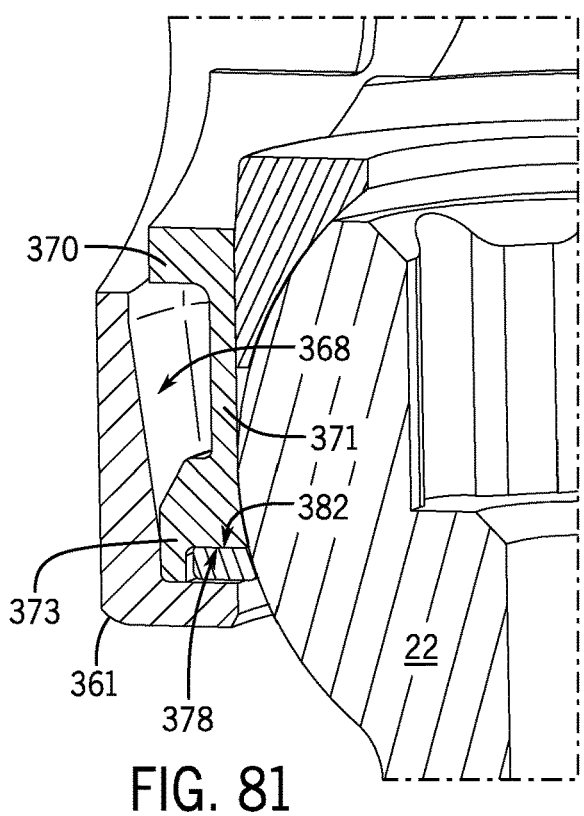
FIG. 81 is a cross-sectional side view of the receiver sub-assembly and shank head in the fully locked configuration of FIG. 79.

Once the hook portions 86 of the disassembly tool 80 are engaged within the upper tool engagement recesses 153, as shown in FIGS. 53-54, the center portion 82 of the disassembly tool 80 is withdrawn upward to pull the opposed lateral ridges 158 of the collet insert 150 from the lower capture/locking state grooves 122 to the upper shipping state grooves 120, as shown in FIGS. 55-56. In practice, the disassembly tool 80 can further include an outer portion (not shown) that engages with and pushes downwardly on the receiver 100 while the center portion 82 is withdrawn upwardly. This can include the application of considerable force between the disassembly tool 80 and the receiver 100 to pull the opposed lateral ridges 158 upward out of the lower grooves 122 and onto the discontinuous cylindrical surface 118 of the receiver central bore 114. For example, in one aspect the force required to overcome this engagement can be about 400 pounds-force or greater, generally provided by the counter-directional movement between the center portion 82 and outer portion of the disassembly tool 80. In situations where the position of an implanted bone anchor 20 is fixed, this causes the receiver 100 with its lower capture/locking state grooves 122 and upper shipping state grooves 120 to displace downwardly relative to the shank head 22, rather than the collet insert 150 to displace upwardly. It will be appreciated that the application of force between the disassembly tool 80 and the receiver 100, provided by the counter-directional movement between the center portion 82 and outer portion (not shown) of the disassembly tool 80, can substantially balance the load across the receiver 100 so as to reduce or substantially eliminate the transfer of any disassembly loads or forces to the shank head 22.

With reference to FIGS. 57-58, once the opposed lateral ridges 158 of the collet insert 150 are positioned within the upper shipping state grooves 120, the entire receiver sub-assembly 14 can then be pulled upward off the bone anchor or shank 20 by the disassembly tool 80 having hook portions 86 that are still engaged within the tool engagement recesses 155 of the collet insert 150, causing the collet fingers 168 to flex outward and the distal pocket opening 176 to expand within the upper expansion chamber 128 of the receiver cavity 126, until the distal pocket opening 176 expands sufficiently to allow passage of the shank head. The disassembly tool 80 can be used to continue pulling the receiver sub-assembly 14 upward off the bone anchor 20 until the shank head 22 exits the bottom opening 136 of the receiver 100, as shown in FIG. 59. After removal of the receiver sub-assembly 14 from the shank head 22, in one aspect the disassembly tool 80 can be disengaged from the receiver sub-assembly 14 by rotating the disassembly tool 80 about the receiver longitudinal axis until the hook portions 86 slide out from the tool engagement recesses 155 (see FIG. 59).

It is foreseen that other shapes and configurations for the disassembly tool 80, the receiver 100 and the collet insert 150, different from those shown in the drawings while providing for similar interaction and functionality for disassembling the pivotal bone anchor assembly, are also possible and considered to fall within the scope of the present disclosure. For example, it is contemplated that the disassembly tool 80 can access the collet insert 150 by other routes, such as through apertures in the upright arms 104 of the receiver 100, and the like.

With reference to FIGS. 60-63, illustrated therein is another representative embodiment 200 of the pivotal bone anchor assembly that is substantially similar to the pivotal bone anchor assembly 10 described above, except for modifications to the interface between the partial spherical seating surface 214 of the receiver cavity 212, and to the outer partial spherical surfaces 224 of the distal tip sections 222. In particular, the partial spherical seating surface 214 of the receiver 210 can be modified to include an inwardly-projecting ridge 216 having a horizontal top surface 217. In addition, the outer partial spherical surfaces 224 of the distal tip sections 222 can be modified to include a complementary notch 226 that is sized and shaped to receive the ridge 216 in the capture/locking state position, as shown in FIG. 63.

It is contemplated that the above-referenced modifications, which serve to establish a seating interface with a ridged surface, may modify or improve the resistance to pull-out of the shank head 22 from the receiver sub-assembly 204 during assembly, loading, and use. For instance, and similar to the pull-out analysis described above, the interface between the receiver partial spherical seating surface 214 with the inwardly-projecting ridge 216 and the plurality of outer partial spherical surfaces 224 of the distal tip sections 222 can determine the strength, or pull-out resistance, of the fully locked pivotal bone anchor assembly 100. The distal tip sections 222 of the collet insert 220 are configured to transfer load from the shank head 22 to the receiver base 211. Relative motion between the distal tip sections 222 and the receiver base 211 is limited by friction and/or interference between the notched outer surfaces 224 of the distal tip sections 222 and the ridged partial spherical seating surface 214 of the receiver cavity 212. In addition, the downward-facing horizontal surface 227 of the notch 226 engages with the mating upward-facing horizontal surface 217 of the ridge 216 to provide a positive stop for distal tip pull out relative to the receiver 210, as well as an indexed single location for the collet insert 220 relative to the receiver 210. Assuming that relative motion between the distal tip sections 222 and the receiver base 211 is restricted or substantially prevented, pull-out resistance of the shank 20 is provided by a plurality of shear walls in the collet fingers 221 and distal tip sections 222 that start at the major diameter of the shank head 222 and terminate at the bottom surface 228 of the distal tip sections 222.

With reference to FIGS. 64-67, illustrated therein is yet another representative embodiment 250 of the pivotal bone anchor assembly that is also substantially similar to the pivotal bone anchor assembly 10 described above, except for modifications to the interface between the partial spherical seating surface 264 of the receiver cavity 262, and to the outer partial spherical surfaces 274 of the distal tip sections 272. In particular, the partial spherical seating surface 264 of the receiver 260 can be modified to include a horizontal, upwardly-facing stepped surface 266 at the lower end thereof. In addition, the distal tip sections 272 of the collet insert 270 can be shortened so that, when the collet insert 270 is downwardly deployed into the capture/locking state position, the bottom surfaces 278 of the distal tip sections 272 simultaneously engage the upwardly-facing stepped surface 266 while the outer partial spherical surfaces 274 of the distal tip sections 222 engage the partial spherical seating surface 264 of the receiver cavity 262.

It is contemplated that the above-referenced modifications, which serve to establish a seating interface with a stepped surface, may improve the resistance to pull-out of the shank head 22 from the receiver sub-assembly 254 during assembly, loading, and use. For instance, and similar to the pull-out analyses described above, the interface between the partial spherical seating surface 264 with the upwardly-facing stepped surface 266 of the receiver 260 and the plurality of outer partial spherical surfaces 274 and bottom surfaces 278 of the shortened distal tip sections 270 can determine the strength, or pull-out resistance, of the fully locked pivotal bone anchor assembly 250. The distal tip sections 272 of the collet insert 270 are configured to transfer load from the shank head 22 to the receiver base 261. Relative motion between the distal tip sections 272 and the receiver base 261 is limited by friction and/or interference between the outer surfaces 274 and bottom surfaces 278 of the distal tip sections 272 and the partial spherical seating surface 264 and stepped surfaces 266 of the receiver cavity 262. In addition, the horizontal downward-facing bottom surfaces 278 of the shortened distal tip sections 272 engage with the mating horizontal upward-facing stepped surface 266 to provide a positive stop for distal tip pull out relative to the receiver 260, as well as an indexed single location for the collet insert 270 relative to the receiver 260. Assuming that relative motion between the distal tip sections 272 and the receiver base 261 is restricted or substantially prevented, pull-out resistance of the shank 20 is provided by a plurality of shear walls in the collet fingers 271 and distal tip sections 272 that start at the major diameter of the shank head 222 and terminate at the bottom surface 278 of the distal tip sections 272.

With reference to FIGS. 68-74, illustrated therein is yet another representative embodiment 300 of the pivotal bone anchor assembly that is also substantially similar to the pivotal bone anchor assembly 10 described above, except for modifications to the interface between the partial spherical seating surface 314 of the receiver cavity 312 and the outer partial spherical surfaces 324 of the distal tip sections 322. In particular, the partial spherical seating surface 314 can be modified to include a circumferential expansion ring slot 316 that is sized and shaped to receive a separate expansion ring 330. The expansion ring 330 can be uploaded separately into the receiver cavity 312 prior to the uploading of the shank head 22. The expansion ring slot 316 is sufficiently deep to allow the expansion ring 330 to expand outward to allow passage of the shank head 22 during uploading, and then to close back around the lower portion of the spherical outer surface 32 below the hemisphere plane. In addition, the distal tip sections 322 of the collet insert 320 can be shortened so that, when the collet insert 320 is downwardly deployed into the capture/locking state position, the bottom surfaces 328 of the distal tip sections 322 simultaneously engage the top surface 332 of the expansion ring 330 while the outer partial spherical surfaces 324 of the distal tip sections 322 engage the partial spherical seating surface 314 that is located above the circumferential expansion ring slot 316.

It is contemplated that the above-referenced modifications, which serve to establish a seating interface with expansion ring support, may improve the resistance to pull-out of the shank head 22 from the receiver sub-assembly 304 during assembly, loading, and use. For instance, and similar to the pull-out analyses described above, the interface between the partial spherical seating surface 314 and the expansion ring 330 and the plurality of outer partial spherical surfaces 324 of the distal tip sections 322 can determine the strength, or pull-out resistance of the fully locked pivotal bone anchor assembly 300. The distal tip sections 322 of the collet insert 320 are configured to transfer load from the shank head 22 to the receiver base 311. Relative motion between the distal tip sections 322 and the receiver base 311 is limited by friction and interference between the outer and bottom surfaces of the distal tip sections 322 and the partial spherical seating surface 314 of the receiver cavity 312 and the expansion ring 300. In addition, the horizontal downward-facing bottom surfaces 328 of the shortened distal tip sections 322 engage with the mating horizontal upward-facing top surface 332 of the expansion ring 330 to provide a positive stop for distal tip pull out relative to the receiver 310, as well as an indexed single location for the collet insert 320 relative to the receiver 310. Assuming that relative motion between the distal tip sections 322 and the receiver base 311/expansion ring 330 is restricted or substantially prevented, pull-out resistance of the shank 22 is provided by a plurality of shear walls in the collet fingers 321 and distal tip sections 322 that start at the major diameter of the shank head 22 and terminate at the bottom surface 328 of the distal tip sections 322.

With reference to FIGS. 75-81, illustrated therein is yet another representative embodiment 350 of the pivotal bone anchor assembly that is also substantially similar to the pivotal bone anchor assembly 10 described above, except for modifications to the interface between the partial spherical seating surface 364 of the receiver cavity 362 and the outer partial spherical surfaces 374 of the distal tip sections 372. In particular, the partial spherical seating surface 364 can be modified to include a circumferential expansion ring slot 366 that is sized and shaped to receive a separate expansion ring 380, which is subsequently restrained by tab extensions 373 projecting from the collet insert 370. The expansion ring 380 can be uploaded separately into the receiver cavity 362 prior to the uploading of the shank head 22. The expansion ring slot 366 is sufficiently deep to allow the expansion ring 380 to expand outward to allow passage of the shank head 22. The distal tip sections 372 of the collet insert 370 can be shorted so that, when the collet insert 370 is downwardly deployed into the capture/locking state position, the bottom surfaces 378 of the distal tip sections 372 simultaneously engage the top surface 382 of the expansion ring 380 while the outer partial spherical surfaces 374 of the distal tip sections 372 engage the receiver partial spherical seating surface 364.

As can be seen in the drawings, the distal tip sections 372 of the collet insert 370 can be further modified to include tab extensions 373 that project radially outward from distal tip sections 372 of a plurality of collet fingers 371. In one embodiment, three of six collet fingers 371 can include tab extensions 373 while the remaining three can have outer partial spherical surfaces 374. The upper expansion chamber and the conical transition surface portions of the receiver cavity 362 can also be further modified to include a plurality of vertical recesses 368 that are sized and shaped to receive the plurality of tab extensions 373 projecting radially from the distal tip sections 372 of the collet insert 370. When the collet insert 370 is downwardly deployed into the capture/locking state position, the tab extensions 373 can slide behind the expansion ring 380 to prevent the outward deflection of the expansion ring 380 into the expansion ring slot 366 during loading of the pivotal bone anchor 350. The tab extensions 373 can prevent outward expansion of the expansion ring 380 back into its expansion ring slot 366 to better restrict the relative motion between the distal tip sections 370 and the receiver base 361 and expansion ring 380.

It is contemplated that the above-referenced modifications, which serve to establish a seating interface with constrained expansion ring support, may improve the resistance to pull-out of the shank head 22 from the receiver sub-assembly 354 during assembly, loading, and use. For instance, and similar to the pull-out analyses described above, the interface between the partial spherical seating surface 364 and the expansion ring 380 and the plurality of outer partial spherical surfaces 374 of the distal tip sections 372 can determine the strength, or pull-out resistance, of the fully locked pivotal bone anchor assembly 350. The distal tip sections 372 of the collet insert 370 are configured to transfer load from the shank head 22 to the receiver base 361. Relative motion between the distal tip sections 372 and the receiver base 361 is limited by friction and interference between the outer surfaces 374 and bottom surfaces 378 of the distal tip sections 372 and the partial spherical seating surface 364 of the receiver cavity 362 and expansion ring 380. In addition, the horizontal downward-facing bottom surfaces 378 of the shortened distal tip sections 372 engage with the mating horizontal upward-facing top surface 382 of the expansion ring 380 to provide a positive stop for distal tip pull out relative to the receiver 360, as well as an indexed single location for the collet insert 370 relative to the receiver 360. Assuming that relative motion between the distal tip sections 372 and the receiver base 361 and the expansion ring 380 is restricted or substantially prevented, pull-out resistance of the shank 20 is provided by a plurality of shear walls in the collet fingers 371 and distal tip sections 372 that start at the major diameter of the shank head 22 and terminate at the bottom surface 378 of the distal tip sections 372.

Figure 82:
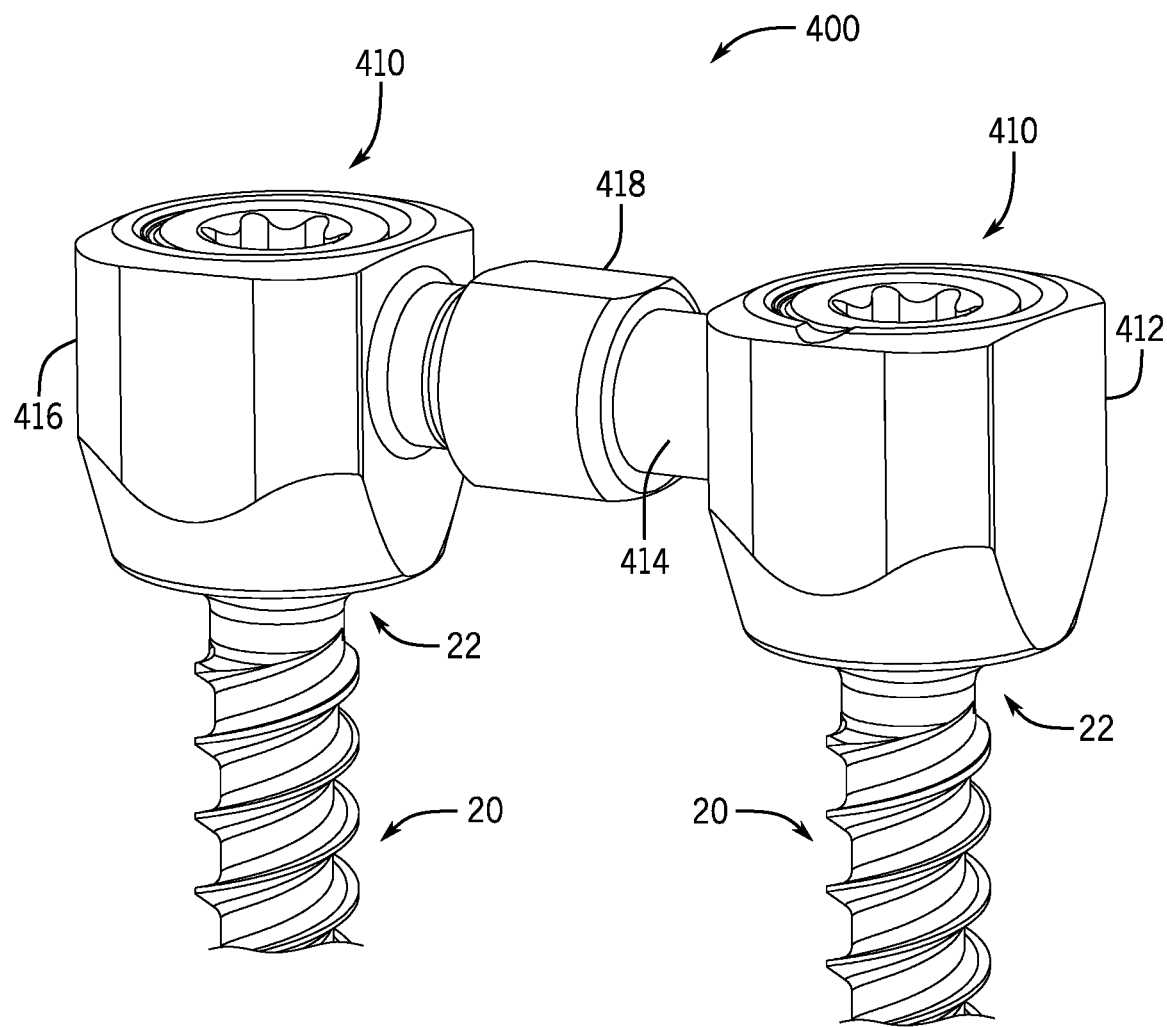
FIG. 82 is a perspective view of a pair of pivotal bone anchor assemblies coupled to shank heads, each with housings configured for adjacent level connection, in accordance with yet another representative embodiment of the present disclosure.
Figure 83:
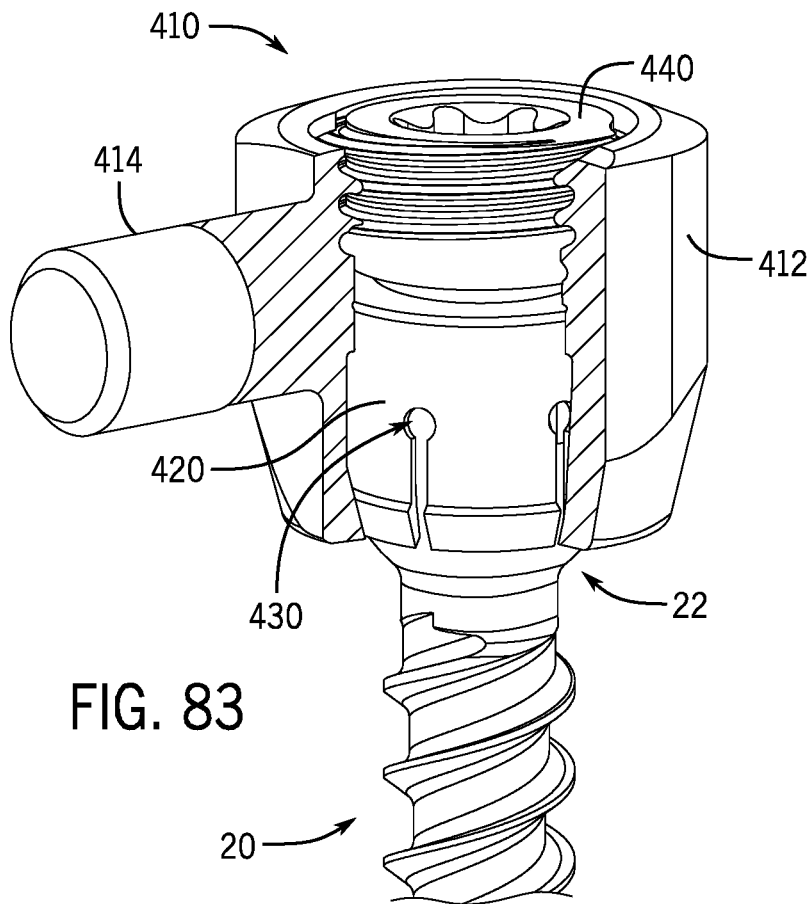
FIG. 83 is a partially cut-away perspective view of one of the pair of pivotal bone anchor assemblies and its coupled shank head of FIG. 82.
Figure 84:
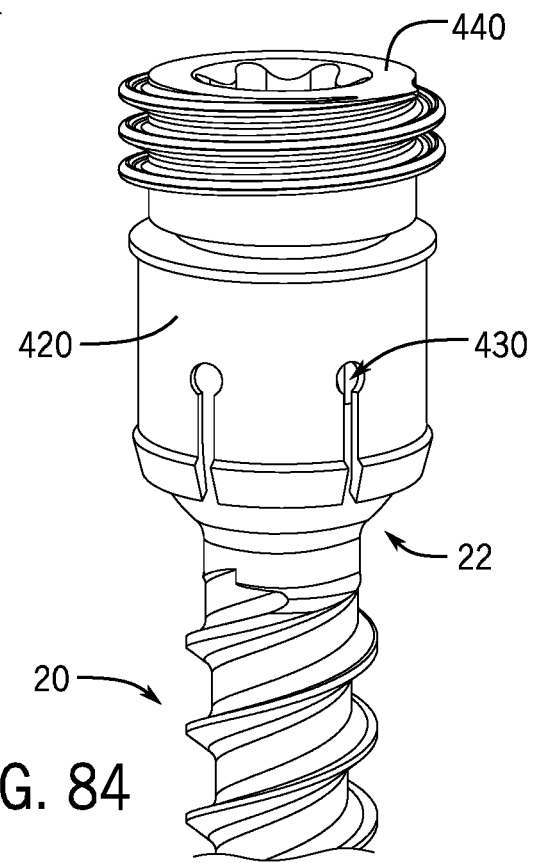
FIG. 84 is an isolated perspective view of the pivotal bone anchor assembly and bone anchor of FIG. 83 upon removal of the housing.

Illustrated in FIGS. 82-84 is yet another representative embodiment 400 of a pivotal bone anchor apparatus or assembly in which the elongate rods and receivers have been replaced with housings 410 that provide for adjacent level connection. For example, the housings 410 of the pivotal bone anchor assemblies 400 can replace the receiver 100 discussed above with respect to FIGS. 1-59, with the housings 410 containing internal components, such as a modified collet insert 420 and an enclosed pressure ring 430, that are similar in function to the collet insert and enclosed pressure ring described above as residing in the receiver 100 shown in FIGS. 1-99.

As shown in FIG. 82, in one aspect the housings 410 of the pivotal bone anchor assembly can be separated into a male housing 412 having a male cord or projection 414 that is received in pivotal arrangement within a female receptacle 418 of a female housing 416 immediately adjacent the male housing 412.

The housing 410 of FIGS. 83-84 further illustrates the separate collet insert 420 that has been modified to remove the upwardly projecting arm structures that define an insert channel, while still including structures that can provide for the downward deployment of the collet insert 420 within the housing 410 to a capture/locking state position around the shank head 22, prior to the installation of the closure 440. For example, the collet insert 420 can include insert ridges that snap into lower capture/locking receiver grooves, the partial spherical seating surface of the receiver cavity can engage the plurality of outer partial spherical surfaces of the distal tip sections to restrain further outward movement for flexing of the distal tip sections, and the plurality of inner partial spherical surfaces of the distal tip sections more forcefully engage the lower portion of the spherical outer surface of the shank head 22 to prevent the shank head from exiting downward through the receiver bottom opening.

Also as described above, the pressure ring 430 is subsequently downwardly deployable from its position in the upper portion of the collet pocket until the upwardly-concave partially spherical bottom surface of the load ring engages the upper portion of the shank head spherical surface. In one aspect the deployment of the pressure ring is sufficient to establish, or further assure, a non-floppy friction fit that holds the position of the receiver sub-assembly relative to the shank head 22, while still allowing for movement of the receiver sub-assembly relative to the bone anchor 20 with an applied force.

With housings 410 so equipped with these internals, each housing 410 is also able to couple with the above-described shank heads 22, as generally outlined above with respect to FIGS. 1-59. The receivers and housings thus may be considered different versions of a structural envelope that contains complimentary versions a collet insert and an enclosed pressure ring.

As indicated above, the invention has been described herein in terms of preferred embodiments and methodologies considered by the inventor to represent the best mode of carrying out the invention. It will be understood by the skilled artisan, however, that a wide range of additions, deletions, and modifications, both subtle and gross, may be made to the illustrated and exemplary embodiments of the pivotal bone anchor assembly without departing from the spirit and scope of the invention. These and other revisions might be made by those of skill in the art without departing from the spirit and scope of the invention that is constrained only by the following claims.

What is claimed is:

1. A bone anchor assembly for securing an elongate rod to a bone of a patient via a closure and with tooling, the bone anchor assembly comprising:
    a shank having a longitudinal axis, a head portion with a partial spherical shape, and an anchor portion opposite the head portion configured for fixation to the bone;
    a receiver comprising a base defining an internal cavity in communication with a bottom of the receiver through a bottom opening configured to allow passage of the head portion of the shank when uploaded into the internal cavity, a pair of upright arms extending upwardly from the base to define a first channel configured to receive the elongate rod, and an axial bore centered around a vertical centerline axis, the axial bore extending upward from the bottom opening through the internal cavity and the channel to top surfaces of the upright arms, the upright arms including an internal thread adjacent the top surfaces and interference abutment surfaces below the internal thread;
    an insert positionable within the axial bore of the receiver in a first position, the insert comprising a central opening, an upward-facing second channel configured to receive the elongate rod when the elongate rod is received in the first channel, and opposite lateral protrusions positioned above the interference abutment surfaces when the insert is in the first position; and
    a unitary and resiliently expandable retainer positionable within the internal cavity through the bottom opening of the receiver before the head portion of the shank and configured to capture and hold the head portion in the internal cavity,
    wherein after the head portion of the shank is uploaded into the internal cavity of the receiver and captured by the retainer, and prior to locking an angular position of the shank relative to the receiver with the closure, the insert is downwardly deployable by the tooling into a second position within the axial bore, with the opposite lateral protrusions being forced below the interference abutment surfaces so as to inhibit the insert from moving back up within the receiver, and with lower portions of the insert entering into direct compressive overlapping engagement with the retainer to hold down the retainer within the internal cavity.

2. The bone anchor assembly of claim 1, wherein the insert further comprises a lower collet portion configured to engage the head portion of the shank while extending downward below a hemisphere plane defined at a maximum width of the head portion.

3. The bone anchor assembly of claim 1, wherein the insert further comprises a pair of opposed radial extensions extending radially outward from the insert to maintain an alignment of the insert between the upright arms.

4. The bone anchor assembly of claim 1, wherein the insert is configured to be downloaded into the axial bore of the receiver with the opposite lateral protrusions positioned adjacent to and above the interference abutment surfaces.

5. The bone anchor assembly of claim 1, wherein the opposite lateral protrusions extend circumferentially around an outer surface of the insert to define a discontinuous annular planar upper surface.

6. The bone anchor assembly of claim 1, wherein the insert includes a vertical slot.

7. The bone anchor assembly of claim 1, further comprising a load bearing structure positionable into the central opening of the insert, the load bearing structure having an upper surface configured to engage the elongate rod and a lower surface configured to engage the head portion of the shank so as to lock the shank relative to the receiver.

8. The bone anchor assembly of claim 1, wherein the retainer is non-pivoting with respect to the receiver.

9. The bone anchor assembly of claim 1 and further comprising the elongate rod and the closure, wherein after the insert is downwardly deployed into the second position, the elongate rod is positionable within the channel of the receiver and the closure is positionable entirely within the axial bore of the receiver above the elongate rod and in engagement with the internal thread of the upright arms so as to apply a downwardly-directed pressure to a top of the elongate rod.

10. A method of assembling a bone anchor assembly for securing an elongate rod to a bone of a patient via a closure with a tool, the method comprising:
   loading an insert into an axial bore of a receiver, the receiver including a base defining an internal cavity in communication with a bottom of the receiver through a bottom opening, a pair of upright arms extending upwardly from the base to define a first channel configured to receive the elongate rod, and the axial bore centered around a vertical centerline axis and extending upward from the bottom opening through the internal cavity and the channel to top surfaces of the upright arms, and the upright arms including an internal thread adjacent the top surfaces and interference abutment surfaces below the internal thread;
   positioning the insert into a first position in the axial bore with opposite lateral protrusions of the insert adjacent to and above the interference abutment surfaces of the axial bore, the insert having a central opening and an upward-facing second channel configured to receive the elongate rod when the elongate rod is received in the first channel;
   positioning a unitary and resiliently expandable retainer within the internal cavity through the bottom opening of the receiver and below the insert, the retainer being configured to capture and hold a partial spherical shaped head portion of a shank in the internal cavity;
   uploading the head portion of the shank into the internal cavity through the bottom opening of the receiver and the retainer, the shank including a longitudinal axis and an anchor portion opposite the head portion configured for fixation to the bone; and
   after the head portion of the shank is uploaded into the internal cavity of the receiver and captured by the retainer, and prior to locking an angular position of the shank relative to the receiver with the closure, downwardly deploying the insert into a second position within the axial bore using the tool, with the opposite lateral protrusions being forced below the interference abutment surfaces so as to inhibit the insert from moving back up within the receiver and with lower portions of the insert entering into direct compressive overlapping engagement with the retainer to hold down the retainer within the internal cavity.

11. The method of claim 10, wherein the insert further comprises a lower collet portion configured to engage the head portion of the shank while extending downward below a hemisphere plane defined at a maximum width of the head portion.

12. The method of claim 10, wherein the insert further comprises a pair of opposed radial extensions extending radially outward from the insert to maintain an alignment of the insert between the upright arms when the insert is downwardly deployed from the first position to the second position.

13. The method of claim 10, wherein the opposite lateral protrusions extend circumferentially around an outer surface of the insert to define a discontinuous annular planar upper surface.

14. The method of claim 10, wherein the insert includes a cylindrical body portion.

15. The method of claim 14, wherein positioning the insert into a first position in the axial bore further comprises rotating the insert about the vertical centerline axis of the receiver until the opposite lateral protrusions rotate into position adjacent to and above the interference abutment surfaces.

16. The method of claim 10, wherein the insert includes a vertical slot.

17. The method of claim 10, wherein the retainer is configured as a single part with a through and through gap.

18. The method of claim 10, further comprising a load bearing structure positionable into the central opening of the insert, the load bearing structure having an upper surface configured to engage the elongate rod and a lower surface configured to engage the head portion of the shank so as to lock the shank relative to the receiver.

* * * * *